US009352046B2

(12) United States Patent
Voigts et al.

(10) Patent No.: US 9,352,046 B2
(45) Date of Patent: May 31, 2016

(54) IMPLANTATION COMPOSITIONS FOR USE IN TISSUE AUGMENTATION

(71) Applicant: MERZ NORTH AMERICA, INC., Greensboro, NC (US)

(72) Inventors: Robert Voigts, Windlake, WI (US); Dale Devore, Chelmsford, MA (US)

(73) Assignee: MERZ NORTH AMERICA, INC., Greensboro, NC (US)

( * ) Notice: Subject to any disclaimer, the term of this patent is extended or adjusted under 35 U.S.C. 154(b) by 0 days.

(21) Appl. No.: 14/269,466

(22) Filed: May 5, 2014

(65) Prior Publication Data

US 2014/0378549 A1  Dec. 25, 2014

Related U.S. Application Data

(60) Continuation of application No. 13/924,240, filed on Jun. 21, 2013, now abandoned, which is a division of application No. 12/521,947, filed as application No. PCT/US2007/017131 on Jul. 31, 2007, now abandoned, which is a continuation-in-part of application No. 11/650,696, filed on Jan. 8, 2007, now abandoned, which is a continuation-in-part of application No. 11/348,028, filed on Feb. 6, 2006, now abandoned.

(51) Int. Cl.
| | |
|---|---|
| *A61F 2/00* | (2006.01) |
| *A61K 31/715* | (2006.01) |
| *A01N 37/18* | (2006.01) |
| *A61K 31/16* | (2006.01) |
| *A61K 31/045* | (2006.01) |
| *A61K 47/38* | (2006.01) |
| *A61L 27/20* | (2006.01) |

(Continued)

(52) U.S. Cl.
CPC ............... *A61K 47/38* (2013.01); *A61K 31/167* (2013.01); *A61K 47/02* (2013.01); *A61K 47/10* (2013.01); *A61L 2/0023* (2013.01); *A61L 27/20* (2013.01); *A61L 27/50* (2013.01); *C08L 1/286* (2013.01); *A61L 2400/06* (2013.01); *A61L 2430/34* (2013.01)

(58) Field of Classification Search
CPC .................................................... A61K 47/38
USPC ....................................................... 523/113
See application file for complete search history.

(56) References Cited

U.S. PATENT DOCUMENTS

| | | | |
|---|---|---|---|
| 3,527,217 | A | 9/1970 | Gettig |
| 3,703,575 | A | 11/1972 | Thiele |

(Continued)

FOREIGN PATENT DOCUMENTS

| | | |
|---|---|---|
| CA | 2029338 | 5/1991 |
| CH | 643732 | 1/1978 |

(Continued)

OTHER PUBLICATIONS

Appell, Rodney A..; (1990) Obstetrics and Gynecology Report, 2(3): 334-342, 1."Artificial Urinary Sphincter & Periurethral Injections".

(Continued)

*Primary Examiner* — David Karst
(74) *Attorney, Agent, or Firm* — Hueschen and Sage

(57) ABSTRACT

A composition of matter and method for preparation of a tissue augmentation material. A polysaccharide gel composition is prepared with rheological properties selected for a particular selected application. The method includes preparing a polymeric polysaccharide in a buffer to create a polymer solution or gel suspending properties in the gel and selecting a rheology profile for the desired tissue region.

12 Claims, 40 Drawing Sheets

(51) Int. Cl.
*A61L 27/50* (2006.01)
*C08L 1/28* (2006.01)
*A61L 2/00* (2006.01)
*A61K 31/167* (2006.01)
*A61K 47/02* (2006.01)
*A61K 47/10* (2006.01)

(56) References Cited

U.S. PATENT DOCUMENTS

| | | | |
|---|---|---|---|
| 4,107,288 A | 8/1978 | Oppenheim et al. | |
| 4,123,091 A | 10/1978 | Cosentino et al. | |
| 4,191,747 A | 3/1980 | Scheicher | |
| 4,197,846 A | 4/1980 | Bucalo | |
| 4,322,398 A | 3/1982 | Reiner et al. | |
| 4,330,514 A | 5/1982 | Nagai et al. | |
| 4,373,217 A | 2/1983 | Draenert | |
| 4,387,240 A | 6/1983 | Berg et al. | |
| 4,440,754 A | 4/1984 | Sorenson | |
| 4,500,658 A | 2/1985 | Fox | |
| 4,618,491 A | 10/1986 | Kanematu | |
| 4,619,655 A | 10/1986 | Hanker et al. | |
| 4,657,548 A | 4/1987 | Nichols | |
| 4,659,700 A | 4/1987 | Jackson | |
| 4,693,986 A | 9/1987 | Vit et al. | |
| 4,776,890 A | 10/1988 | Chu | |
| 4,795,467 A | 1/1989 | Piez et al. | |
| 4,803,075 A | 2/1989 | Wallace et al. | |
| 4,842,603 A | 6/1989 | Draenert | |
| 4,849,285 A | 7/1989 | Dillon | |
| 4,866,050 A | 9/1989 | Ben-Amoz | |
| 4,871,361 A | 10/1989 | Kira | |
| 4,917,702 A | 4/1990 | Scheicher et al. | |
| 5,007,940 A | 4/1991 | Berg | |
| 5,011,495 A | 4/1991 | Hollinger | |
| 5,030,391 A | 7/1991 | Sumita et al. | |
| 5,034,352 A | 7/1991 | Vit et al. | |
| 5,035,711 A | 7/1991 | Aoki et al. | |
| 5,067,965 A | 11/1991 | Ersek et al. | |
| 5,075,360 A | 12/1991 | Fitt et al. | |
| 5,116,387 A | 5/1992 | Berg | |
| 5,126,141 A | 6/1992 | Henry | |
| 5,140,016 A | 8/1992 | Goldberg et al. | |
| 5,141,561 A | 8/1992 | Ledard et al. | |
| 5,143,724 A | 9/1992 | Leshchiner et al. | |
| 5,158,573 A | 10/1992 | Berg | |
| 5,192,802 A | 3/1993 | Rencher | |
| 5,204,382 A | 4/1993 | Wallace et al. | |
| 5,246,698 A | 9/1993 | Leshchiner et al. | |
| 5,258,028 A | 11/1993 | Ersek et al. | |
| 5,266,248 A | 11/1993 | Ohtsuka et al. | |
| 5,271,943 A | 12/1993 | Bogart et al. | |
| 5,282,857 A | 2/1994 | Perry et al. | |
| 5,306,302 A | 4/1994 | Bauer et al. | |
| 5,324,775 A | 6/1994 | Rhee et al. | |
| 5,336,263 A | 8/1994 | Ersek et al. | |
| 5,344,452 A | 9/1994 | Lemperle | |
| 5,352,715 A | 10/1994 | Wallace et al. | |
| 5,399,351 A | 3/1995 | Leshchiner et al. | |
| 5,451,406 A | 9/1995 | Lawin et al. | |
| 5,480,644 A | 1/1996 | Freed | |
| 5,487,897 A * | 1/1996 | Polson | A61K 9/0024 424/425 |
| 5,490,984 A | 2/1996 | Freed | |
| 5,523,291 A | 6/1996 | Janzen et al. | |
| 5,571,182 A | 11/1996 | Ersek et al. | |
| 5,573,771 A | 11/1996 | Geistlich et al. | |
| 5,589,180 A | 12/1996 | Hind | |
| 5,591,453 A | 1/1997 | Ducheyne et al. | |
| 5,591,709 A | 1/1997 | Lindenbaum | |
| 5,626,861 A | 5/1997 | Laurencin et al. | |
| 5,637,101 A | 6/1997 | Shillington | |
| 5,670,169 A | 9/1997 | Cornell | |
| 5,681,873 A | 10/1997 | Norton et al. | |
| 5,700,289 A | 12/1997 | Breitbart et al. | |
| 5,702,677 A | 12/1997 | Shimp et al. | |
| 5,709,875 A | 1/1998 | Lebugle et al. | |
| 5,752,974 A | 5/1998 | Rhee et al. | |
| 5,766,618 A | 6/1998 | Laurencin et al. | |
| 5,792,478 A | 8/1998 | Lawin et al. | |
| 5,827,937 A | 10/1998 | Agerup | |
| 5,837,752 A | 11/1998 | Shastri et al. | |
| 5,853,398 A | 12/1998 | Lal et al. | |
| 5,854,382 A | 12/1998 | Loomis | |
| 5,861,176 A | 1/1999 | Ducheyne et al. | |
| 5,922,025 A | 7/1999 | Hubbard | |
| 5,997,574 A | 12/1999 | Hayes et al. | |
| 6,083,522 A | 7/2000 | Chu et al. | |
| 6,130,200 A | 10/2000 | Brodbeck et al. | |
| 6,136,334 A * | 10/2000 | Viegas | A61F 9/00819 424/427 |
| 6,165,514 A | 12/2000 | Bockman et al. | |
| 6,387,978 B2 | 5/2002 | Ronan et al. | |
| 6,432,437 B1 | 8/2002 | Hubbard | |
| 6,537,574 B1 | 3/2003 | Hubbard | |
| 6,558,612 B1 | 5/2003 | Hubbard | |
| 7,060,287 B1 | 6/2006 | Hubbard | |
| 8,067,027 B2 | 11/2011 | Hubbard et al. | |
| 2003/0093157 A1 | 5/2003 | Casares et al. | |
| 2003/0143274 A1 | 7/2003 | Viegas et al. | |
| 2004/0078077 A1 | 4/2004 | Binette et al. | |
| 2004/0096422 A1 | 5/2004 | Schwartz et al. | |
| 2004/0185021 A1 | 9/2004 | Hubbard | |
| 2005/0079202 A1 | 4/2005 | Chen et al. | |
| 2005/0112151 A1 | 5/2005 | Horng | |
| 2005/0266037 A1 * | 12/2005 | Mao | A61K 35/32 424/423 |
| 2006/0173551 A1 | 8/2006 | Hubbard et al. | |
| 2006/0257488 A1 | 11/2006 | Hubbard | |
| 2007/0184087 A1 | 8/2007 | Voigts et al. | |
| 2010/0041788 A1 | 2/2010 | Voigts et al. | |
| 2010/0100179 A1 | 4/2010 | Hubbard | |
| 2010/0240946 A1 | 9/2010 | Hubbard et al. | |

FOREIGN PATENT DOCUMENTS

| | | |
|---|---|---|
| CN | 1370084 A | 9/2002 |
| EP | 196143 | 10/1986 |
| EP | 353936 A1 | 2/1990 |
| EP | 402031 | 12/1993 |
| EP | 0466300 B1 | 5/1998 |
| EP | 1464346 A | 10/2004 |
| GB | 2227176 | 7/1990 |
| JP | 61-050279 | 3/1986 |
| JP | 61101447 | 5/1986 |
| JP | 6211459 | 1/1987 |
| JP | S63-209647 | 8/1988 |
| JP | H02-111359 | 4/1990 |
| JP | 02-297374 | 12/1990 |
| JP | 03-196834 | 8/1991 |
| JP | H04-246361 | 9/1992 |
| JP | 2003-507351 | 2/2003 |
| NL | 8304129 | 7/1985 |
| WO | WO 87/04110 | 7/1987 |
| WO | WO 91/17777 | 11/1991 |
| WO | WO 93/15721 | 8/1993 |
| WO | WO 99/02107 | 1/1999 |
| WO | WO 01/12247 | 2/2001 |
| WO | WO 2005/086697 | 9/2005 |
| WO | WO 2005/107828 | 11/2005 |
| WO | WO 2007/126411 | 11/2007 |

OTHER PUBLICATIONS

Adeyeye, et al. "Viscoelastic Evaluation of Topical Creams Containing Microcrystalline Cellulose/Sodium Carboxymethyl Cellulose as Stabilizer", AAPS PharmSciTech 2002, vol. 3, No. 2, article 8 (http://www.aapspharmschitech.org).

Andrews, et al., "Rheological Characterisation of Primary and Binary Interactive Bioadhesive Gels Composed of Cellulose Derivatives Designed as Ophthalmic Viscosurgical Devices", 2005, pp. 571-580, vol. 26, Elsevier-Biomaterials.

(56) References Cited

OTHER PUBLICATIONS

AQUALON® Sodium Carboxymethylcellulose: Physical and Chemical Properties, Hercules Inc. 1999, pp. 1-29.
Breuls, et al., "A Theoretical Analysis of Damage Evolution in Skeletal Muscle Tissue with Reference to Pressure Ulcer Development", Dec. 2003, vol. 125, pp. 902-909. ASME—http://www.asme.org/terms/Terms_Use.cfm.
Bronneberg, et al., "An in vitro Model System to Study the Damaging Effects of Prolonged Mechanical Loading of the Epidermis", Mar. 2006, pp. 506-514, vol. 34, No. 3, Annals of Biomedical Engineering.
Caro et al., (1978) "The Mechanics of the Circulation," Oxford University Press p. 156.
Chan, et al., "Viscoelastic Shear Properties of Human Vocal Fold Mucosa: Measurement Methodology and Empirical Results", Oct. 1999, vol. 106, No. 4, pp. 2008-2021, J. Acoust. Soc. Am.
Chan et al., (1998) Laryngoscope, 108:725-731, "Viscosities of Implantable Biomaterials in Vocal Fold Augmentation Surgery".
Claes et al. (1989) "Journal of Urology 142:821-822, Pulmonary Migration Following Periurethral Polytetrafluoroethylene Injection for Urinary Incontinence."
Dikstein, S., "Hydropharmacology", 1995, vol. 13, pp. 195-200, Cell Biochemistry and Function.
Drobeck et al. (1984) J. of Oral Maxillofac. Surg., 42: 143-149, "Histologic Observation of Soft Tissue Responses to Implanted, Multifaceted Particles and Discs of Hydroxylapatite."
Ersek et al (Apr. 1991) Plastic and Reconstructive Surgery, pp. 693-701 "Bioplastique: A New Textured Copolymer Microparticle Promises Permanence in Soft Tissue Augmentation."
Gawlitta, D., "Evaluation of a Continuous Qualification Method of Apoptosis and Necrosis in Tissue Cultures", 2004, vol. 46, pp. 139-150, Cytotechnology.
Hench, (1991) Elsevier Science Publishers B.V. pp. 259-274, "Ceramics in Substitutive and Reconstructive Surgery".
Hendriks, et al., "A Numerical-Experimental Method to Characterize the Non-Linear Mechanical Behavior of Human Skin", 2003, vol. 9, pp. 1-26, Skin Res. Technol.
Hendriks, et al., "Influence of Hydration and Experimental Length Scale on the Mechanical Response of Human Skin in vivo, using Optical Coherence Tomography", 2004, vol. 10, pp. 231-241, Skin Res. Technol.
Hendriks, el al., "The Relative Contributions of Different Skin Layers to the Mechanical Behaviour of Human Skin in Vivo Using Suction Experiments", 2006, vol. 28, pp. 259-266, Medical Engineering & Physics.
Ho, et al., "Physical Properties of Human Lips: Experimental and Theoretical Analysis", 1982, vol. 15, No. 11, pp. 859-866, J. Biomechanics.
http://en.wikipedia.org/wiki/Gel as visited on Jul. 23, 2009.
International Preliminary Report on Patentability dated Jul. 23, 2009 for corresponding PCT Application No. PCT/US2007/017131.
International Search Report prepared for PCT International Application No. PCT/US2007/017131, completed Mar. 24, 2009 by the European Patent Office as International Searching Authority, 7 pages.
Jansen, et al., "Evaluation of a Calcium Hydroxylapatite-Based Implant (Radiesse) for Facial Soft-Tissue Augmentation", 2006, pp. 22S-30S, vol. 118, Plast. Reconstr. Surg.
Khatyr, et al., "Model of the Viscoelastic Behaviour of Skin in Vivo and Study of Anisotropy", 2004, vol. 10, pp. 96-103, Skin Research and Technology.
KIC Chemicals. Inc.; Sodium CarboxyMethylCellulose (Cellulose Gum/CMC, Food Grade) Catalog page; downloaded Jul. 7, 2005 from URL: http://www.kicgroup.com/cmc.htm.
Klaas deGroot, (1983) Dental Implants, in Bioceramics of Calcium Phosphate, (ed), CRC Press, pp. 115-129.
Larsen, et al., Hylan Gel for Soft Tissue Augmentation; Matrix Biology Institute, 16th Annual Meeting of the Society for Biomaterials, May 20-23, 1990, p. 302.
Lehtenen et al., (1990) J. Oral Maxillofac Surg, 48:1075-1078 "Soft Tissue Response to Hydroxyapatite Particles of Different Shapes in Rabbit Tibia."
Lemperle et al., (1991) Annals of Plastic Surgery, 26(1):57-63 "PMMA Microspheres for Intradermal Implantation: Part I Animal Research".
Lin, et al., "Viscoelasticity of Anionic Polymers and their Mucociliary Transport on the Frog Palate", 1993, vol. 10, No. 3, Pharmaceutical Research.
Malizia et al. (Jun. 22/29, 1984) JAMA, 251:24 "Migration & Granulomatous Reaction After Periurethral Injection of Polytef (Teflon),".
Meijer, et al., "Chracterisation of Anisoiropic and Non-Linear Behaviour of Human Skin In Vivo", 1999, vol. 1, pp. 13-27, Computer Methods in Biomechanics and Biomedical Engineering.
MicroChem Product Information, NANO™ PMMA and Copolymer, downloaded Nov. 9, 2011 from URL: http://www.microchem.com/pdf/PMMA_Data_Sheet.pdf, 8 pages, MicroChem Corp., Copyright 2011.
Misiek et al., (1984) J. Oral Maxillofac Surge, 42:150-160 "Soft Tissue Responses to Hydroxylapatite Particles of Different Shapes".
Oomens, et al., "A Mixture Approach to the Mechanics of Skin", 1987, vol. 20, No. 9, pp. 877-885, J. Biomechanics.
Oomens, et al., "In Vitro Compression of a Soft Tissue Layer on a Rigid Foundation", 1987, vol. 20, No. 10, pp. 923-635, J. Biomechanics.
Pasyk, et al., "Quantitative Analysis of the Thickness of Human Skin and Subcutaneous Tissue Following Controlled Expansion with a Silicone Implant", 1998, vol. 81, pp. 516-523, Plastic Recontr Surg.
Patel (2005) Wiley InterScience, "Rheological and recovery properties of poly(ethylene glycol) diacrylate hydrogels and human adipose tissue", 7 pages.
Plasma Osmolality, definition; downloaded Nov. 9, 2011 from URL: http://en.wikipedia.org/wiki/Plasma_osmolality, 4 pages.
Politano et al., (Feb. 1974) Journal of Urology, pp. 180-183, vol. III, "Periurethral Teflon Injection for Urinary Incontinence".
Polymethyl methacrylate definition; downloaded Aug. 8, 2005 at URL: http://en.wikipedia.org/wiki/PMMA.
Ramer et al., 16th Annual Meeting of the Society for Biomaterials, May 20-23, 1990. "BiogIass®—A Suspension for Treatment of Urinary Incontinence."
Reihsner, et al., "Two-Dimensional Elastic Properties of Human Skin in terms of an Incremental Model at the In Vivo Configuration", 1995, vol. 17, No. 4, pp. 304-313, Med. Eng Phys.
Remington's Pharmaceutical Sciences, (1990) Gennaro, Ed., 18m Edition, pp. 1304-1305 and 1316.
Shen, et al., "Modified Bilston Nonlinear Biscoelastic Model for Finite Element Head Injury Studies", Oct. 2006, vol. 128, pp. 797-801, J. Biomech Eng.
Shimizu Shin-ich (1988) Biomedical Research, 9 (2) 95-111,"Subcutaneous Tissue Responses in Rats to Injection of Fine Particles of Synthetic Hydroxyapatite Ceramic."
Silver, et al., "Viscoelastic Properties of Human Skin and Processed Dermis", 2001, vol. 7, pp. 18-23, Skin Research and Technology.
Silver, et al., "Mechanobiology of Cartilage: How do Internal and External Stresses Affect Mechanochemical Transduction and Elastic Energy Storage?", 2002, pp. 219-238, Biomechan Model Mechanobiol 1.
Silver, et al., "Viscoelastic Properties of Young and Old Human Dennis: A Proposed Molecular Mechanism for Elastic Storage in Collagen and Elastin", 2002, vol. 86, pp. 1978-1985, Journal of Applied Polymer Science.
Silver, et al., "Mechanobiology of Cartilage: How Do Internal and External Stresses Affect Mechanochemica Transduction", 2003, vol. 95, pp. 2134-2141, J. Appl. Physiol.
Silver, et al., "Physiology of Aging-Invited Review: role of Mechanophysiology in Aging of ECM: Effects of Changes in Mechanochemical Transduction", 2003, vol. 95, pp. 2134-2141, J. Appl. Physiol.
Silver, et al., "Review—Mechanobiology of Force Transduction in Dermal Tissue", 2003, vol. 9, pp. 3-23, Skin Research and Technology.

(56) References Cited

OTHER PUBLICATIONS

Turnhout, et al., "Passive Transverse Mechanical Properties as a Function of Temperature of Rat Skeletal Muscle In Vitro", 2005, vol. 42, pp. 193-207, Biorheology.
U.S. Appl. No. 11/083,542, filed Mar 17, 2005.
Vais, et al., "Rheological Characterization of Carboxymethylcellulose Solution Under Aseptic Processing Conditions", 2002, vol. 25, pp. 41-61, Journal of Food Process Engineering.
Van Vlack et al., (1964) "Elements of Materials Science," Addison Wesley pp. 379-380.

* cited by examiner

| HORIZ. | VERT. | FACTOR | CURRENT X | | |
|---|---|---|---|---|---|
| ○ | ⊙ | $F_o$ | 33 | | |
| ○ | ○ | PBS (mM) | 25 | | |
| ⊙ | ○ | % NaCMC | 2.3 | | |
| ○ | ○ | % GLYCERIN | 1.5 | | |

| | RESPONSE | CONTOUR | CURRENT Y | LO LIMIT | HI LIMIT |
|---|---|---|---|---|---|
| — | PF 0.7 Hz $|\eta^*|$ [cP] | 1792.4528 | 14923.491 | 7200 | 53000 |
| ····· | PF 0.7 Hz Tan (d) | 1 | 1.4104487 | 1 | |
| --- | PF G' 0.7 Hz | 156.32075 | 45.064436 | | 100 |
| -- | PF G" 0.7 Hz | 145.56504 | 46.606078 | | 100 |
| -·- | PF G' 4 Hz | 361.32075 | 115.05565 | | 300 |
| ···· | PF G" 4 Hz | 225.65038 | 93.335414 | | 300 |
| -··- | PF d-R 0.7 Hz | 66.839623 | 44.724107 | | 60 |
| ··- | PF d-R 4 Hz | 121.32075 | 72.954157 | | 110 |

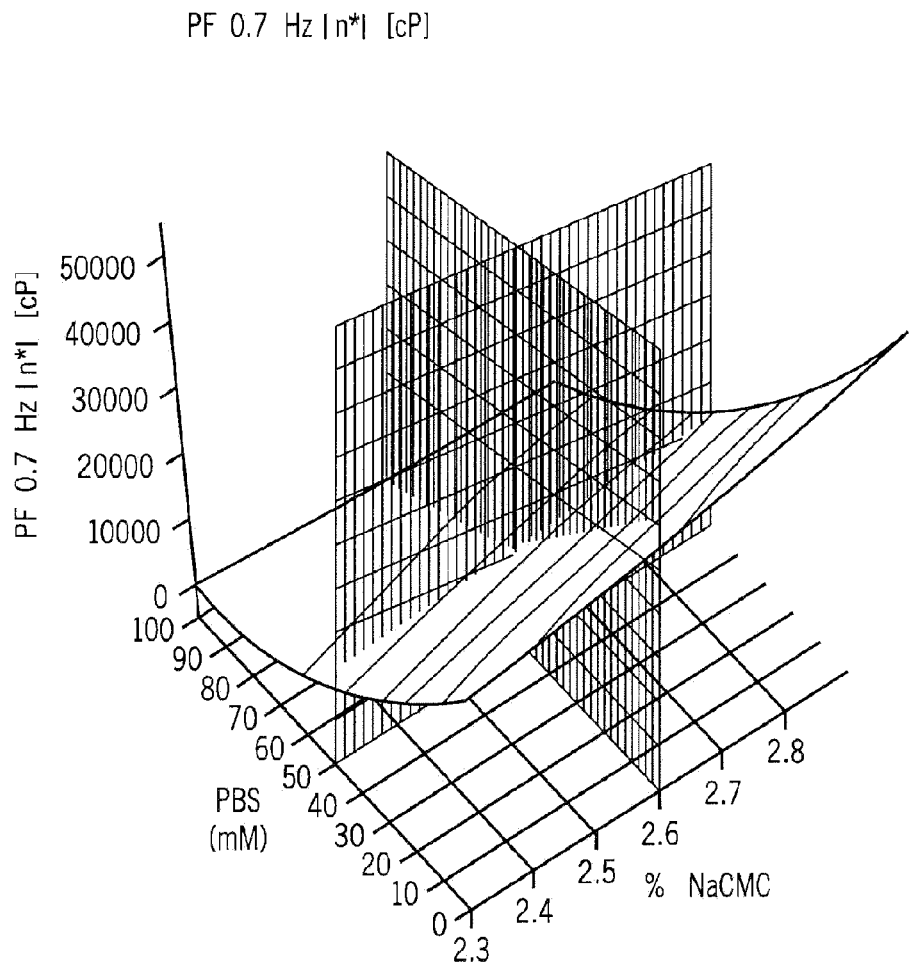
FIG. 9A(ii)

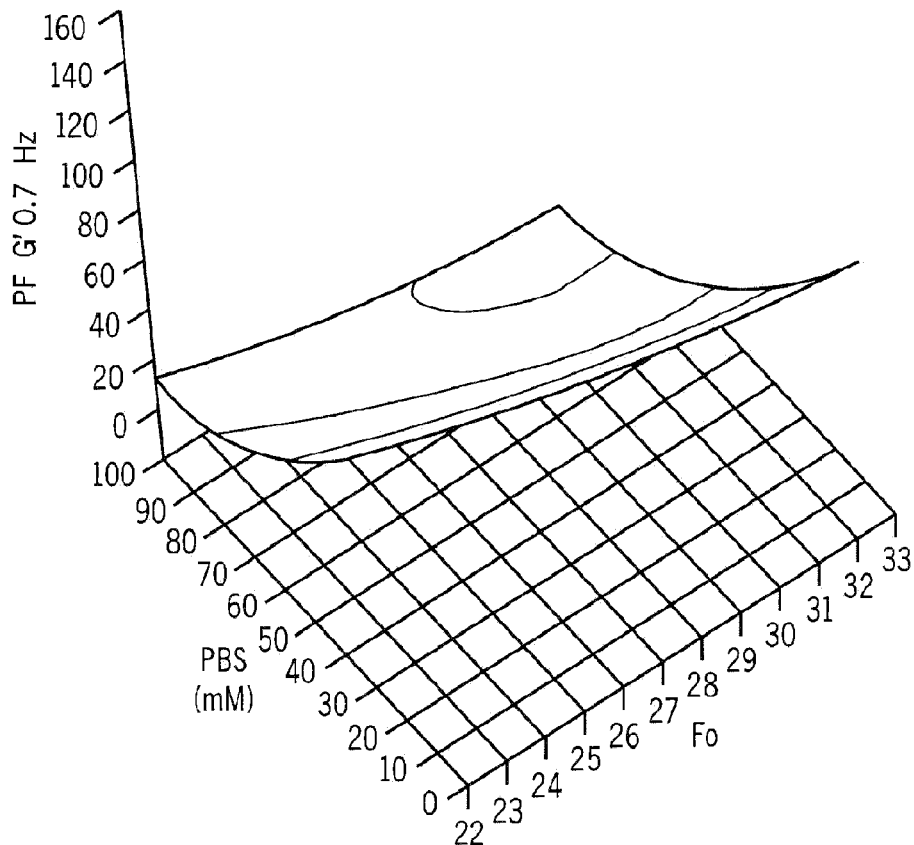
FIG. 9A(iii)

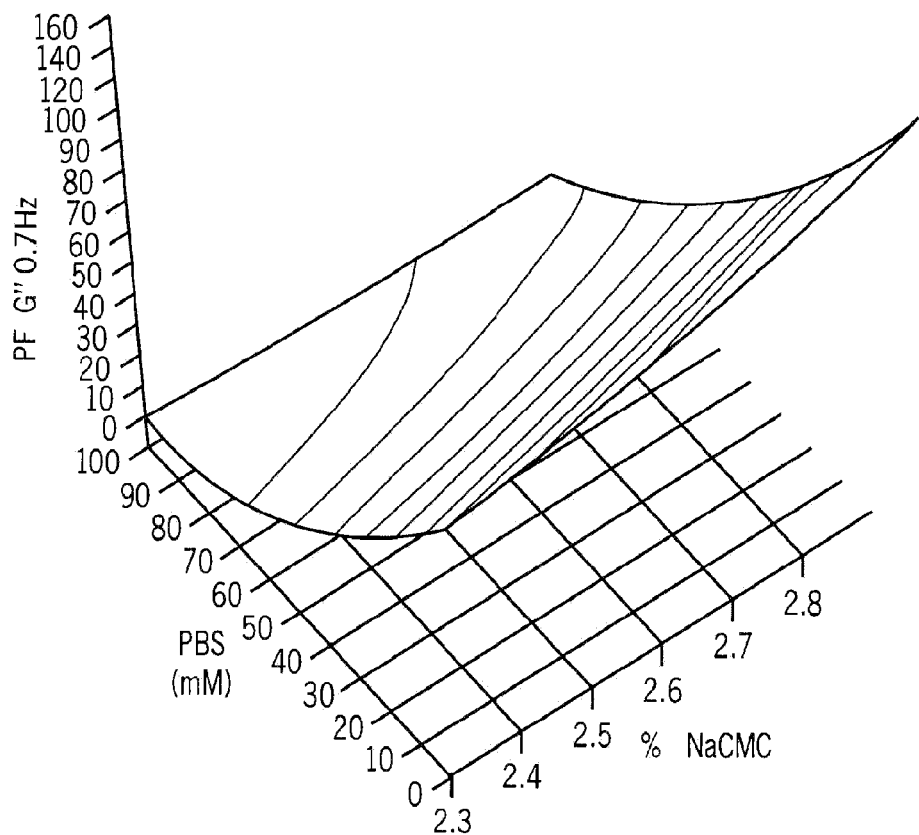
INDEPENDENT VARIABLES
| X | Y | | VALUE | GRID |
|---|---|---|---|---|
| X | X | Fo | 27.5 | |
| X | | PBS (mM) | 50 | |
| | | % NaCMC | 2.6 | |
| | | % Glycerin | 0.75 | |
FIG. 9A(i v)

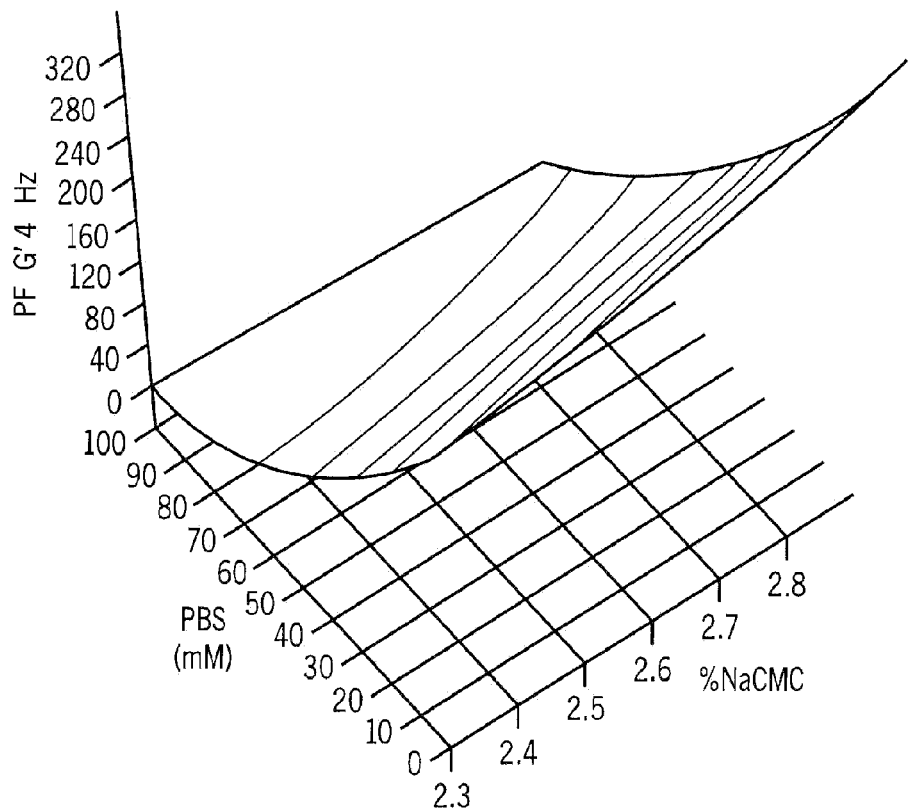
FIG. 9A(vi)

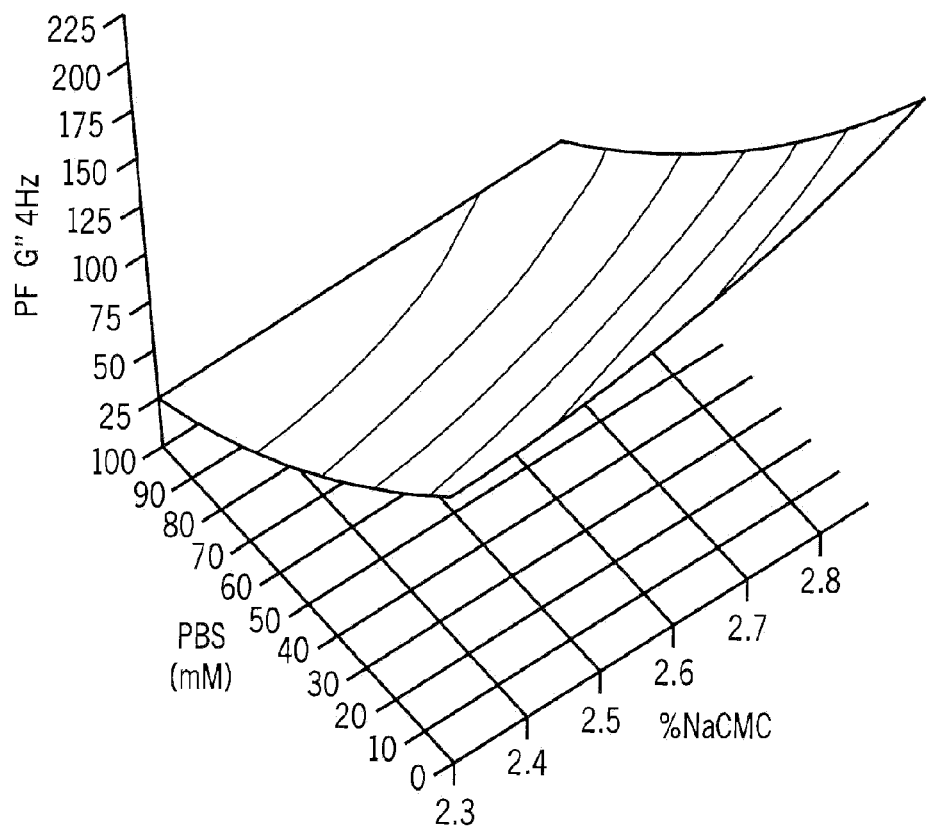
FIG. 9A(vii)

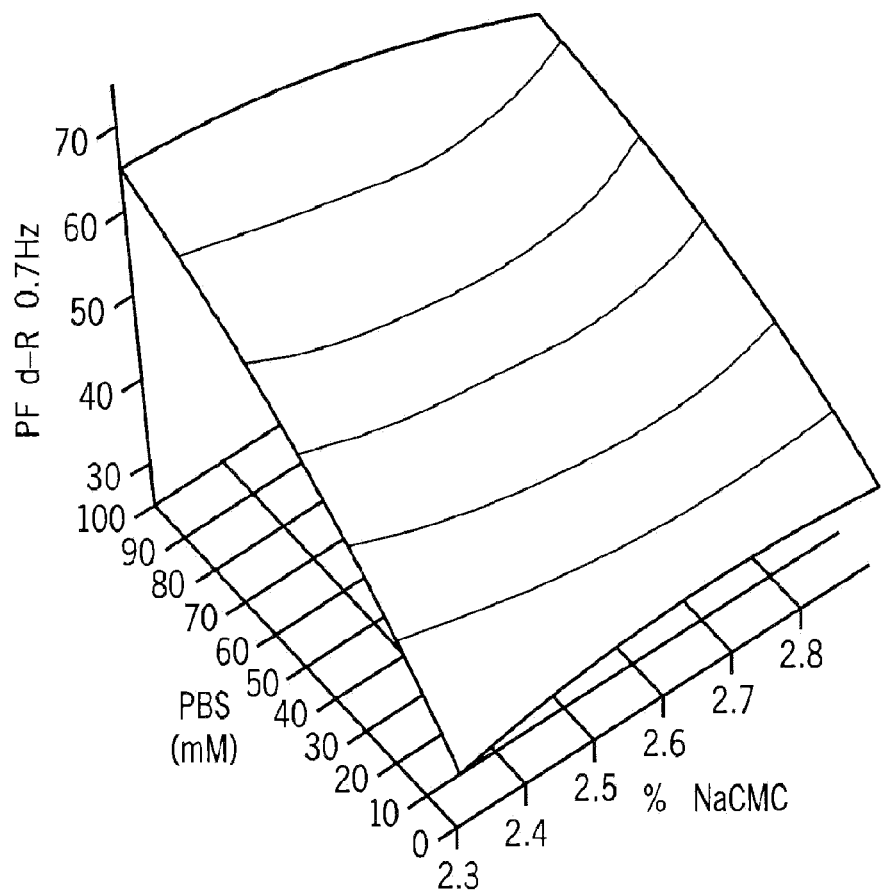
PF d-R 0.7Hz
INDEPENDENT VARIABLES
| X | Y | | VALUE GRID |
|---|---|---|---|
| X | X | Fo | 28 |
| X |   | PBS (mM) | 50 |
|   |   | % NaCMC | 2.6 |
|   |   | % Glycerin | 1.5 |
FIG. 9A(viii)

PF d - R 4 Hz
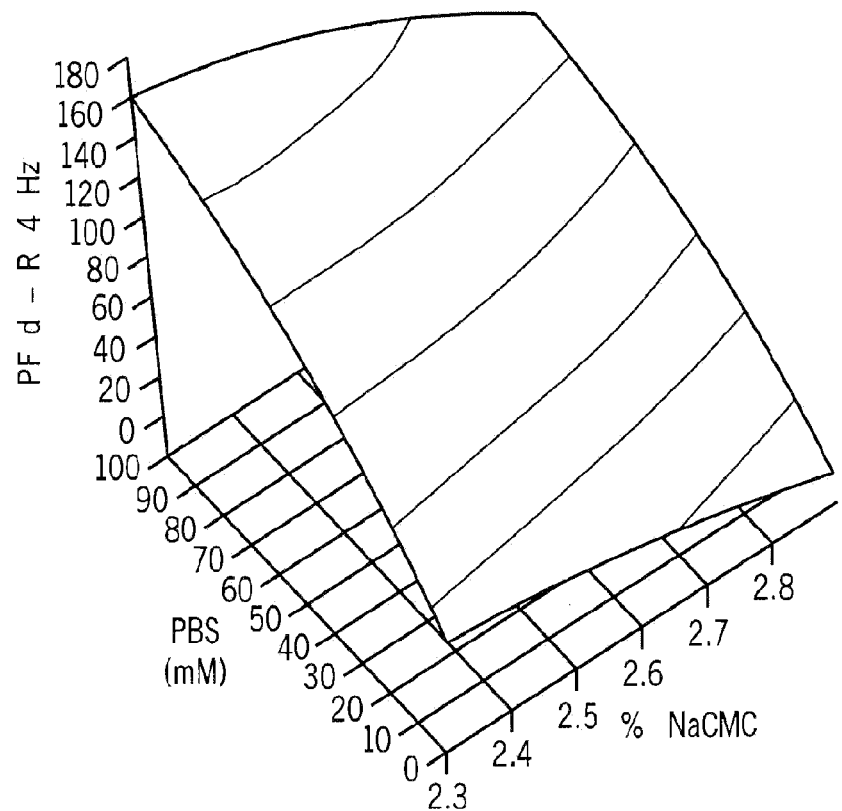
INDEPENDENT VARIABLES
| X | Y | | VALUE | GRID |
|---|---|---|---|---|
| X | X | Fo | 28 | |
| X | | PBS (mM) | 50 | |
| | | % NaCMC | 2.6 | |
| | | % Glycerin | 1.5 | |
FIG. 9A(i x)

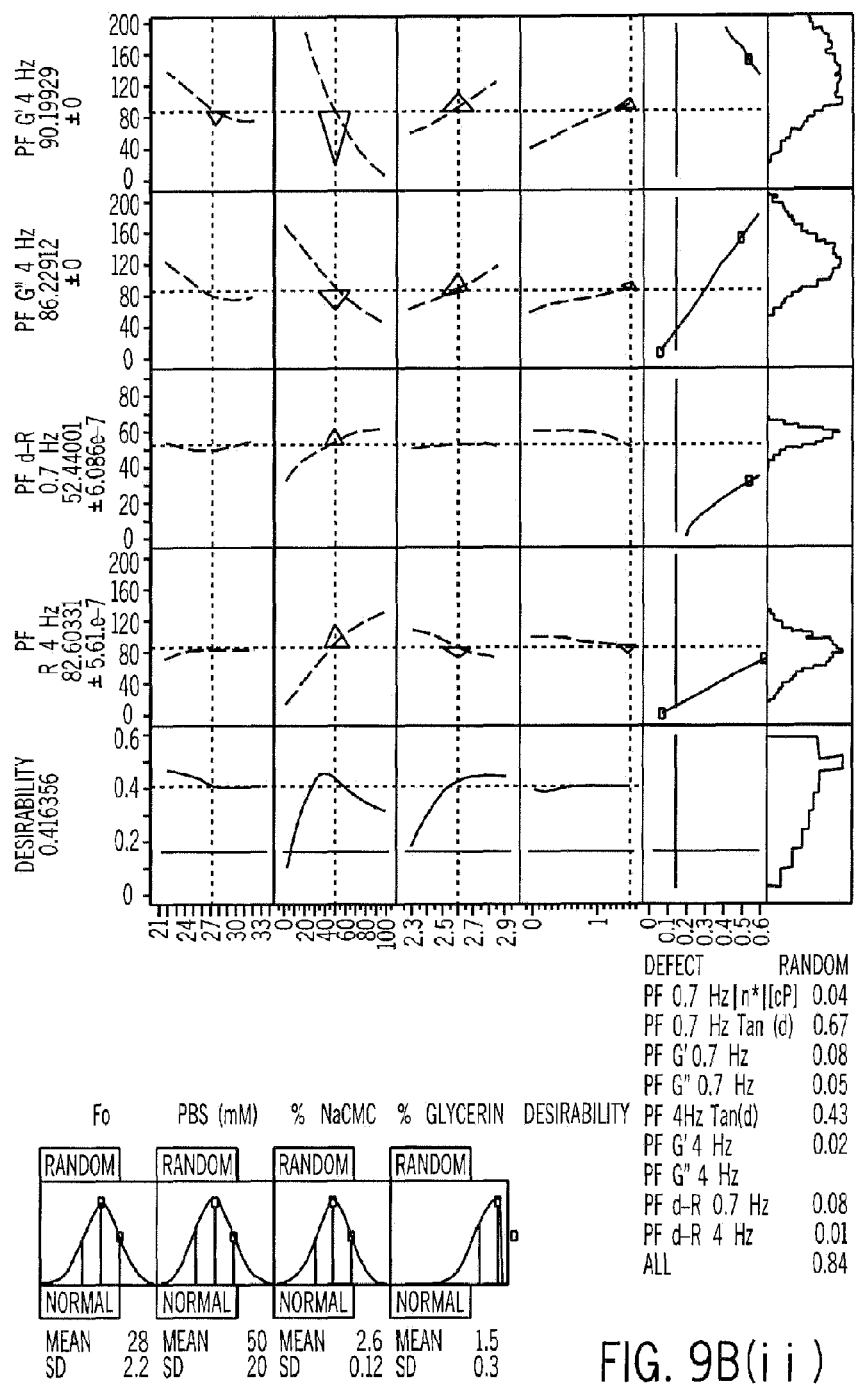
FIG. 9B(ii)

IMPLANTATION COMPOSITIONS FOR USE IN TISSUE AUGMENTATION

CROSS-REFERENCE TO RELATED PATENT APPLICATIONS

The present application is a continuation-in-part of U.S. patent application Ser. No. 13/924,240 filed 21 Jun. 2013, which application is a division of U.S. patent application Ser. No. 12/521,947, filed 1 Jul. 2009, which application is a 371 of PCT International Application No. PCT/US2007/017131, filed 31 Jul. 2007, which application is a continuation-in-part of U.S. patent application Ser. No. 11/348,028, filed 6 Feb. 2006 and U.S. patent application Ser. No. 11/650,696, filed 8 Jan. 2007, the disclosure of each being incorporated herein by reference in it entirety.

FIELD OF THE INVENTION

The present invention relates generally to tissue augmentation, and more particularly to injection of resorbable, biocompatible, gel and solid composites to correct and augment soft tissue with specific application for cosmetic augmentation of tissues.

BACKGROUND OF THE INVENTION

There are a number of non-resorbable, particle-based compositions used for permanent correction or augmentation of soft tissue defects or augmentation for cosmetic purposes. Each composition is associated with certain advantages and disadvantages. Silicone gel was frequently used to treat dermal defects, such as wrinkles, folds, and acne scars in the 1970's and 1980's but has since been prohibited from use in these applications. Silicone was frequently associated with chronic inflammation, granuloma formation, and allergic reactions. TEFLON® paste is a suspension of polytetrafluoroethylene particles in glycerin. This composition was primarily used for vocal fold augmentation and has been associated with granuloma formation. Bioplastics composed of polymerized silicone particles dispersed in polyvinylpyrrolidone. This composition has been withdrawn from commercial application due to frequent chronic inflammation and tissue rejection. Polymethylmethacrylate (PMMA) microspheres having a diameter of 20-40 µm and suspended in a bovine collagen dispersion have been described by Lemperle (U.S. Pat. No. 5,344,452). Since the composition contains collagen from a bovine source, skin testing is required. In addition, the composition is associated with sterilization challenges; the bovine collagen dispersion is damaged by standard terminal sterilization techniques, including heat and gamma irradiation. PMMA is also labile to heat sterilization conditions.

Carboxymethylcellulose and other polysaccharides are examples of material used in gel or solution form for a variety of medical and non-medical applications. Sodium carboxymethylcellulose ("CMC") is cellulose reacted with alkali and chloroacetic acid. It is water soluble and biodegradable and used in a number of medical and food applications. It is also commonly used in textiles, detergents, insecticides, oil well drilling, paper, leather, paints, foundry, ceramics, pencils, explosives, cosmetics and adhesives. It functions as a thickening agent, a bonder, stabilizer, water retainer, absorber, and adhesive.

The prior art gel materials teachings treat the gel merely as a carrier, incidental to the actual augmentation function of the gel; and there has been no directed effort to understanding how best to prepare an implant which is truly compatible rheologically and chemically with an implant site. Further, conventional methods and products fail to address several problems with current gels. More specifically, the injectable materials of the prior art fail to address the specific difficulties in applying implants across a wide range of locations in the body and consequently fail to provide the appropriate type of implant. For example, current implants can experience occlusion, or irregular implantation during the implantation procedure when a fine gauge needle is used. While in certain applications a fine gauge needle may not be required, it is vital to the success of several applications. In addition, a smaller gauge needle leaves a smaller puncture point, which is often desirable to patients. Furthermore, the propensity for occlusions often results in uneven, erratic and discontinuous implantation, which causes highly undesirable results.

In another aspect of conventional methods and products, current implants have failed to address the viscoelastic properties of the implant in the syringe, such that current implants require a significant amount of force, and even irregular levels of force, to extrude the implant from the needle, much more so as the needle gauge is reduced. This presents fatigue issues for medical professionals who may well be performing many injections in a day. This also makes any given injection more difficult to perform, and also perform proper injection amounts and distributions, because of the necessity to exert a large amount, or an irregular amount of force on the syringe, while maintaining a steady needle during injection.

Conventional methods and current implant materials also fail to address the wide range of distinctions in the different tissues in which the implants are placed. Implants can undergo unwanted agglomeration, chemical reaction, phase separation, and premature breakdown of the implanted mass into discontinuous variable shapes, all of which can consequently manifest different undesirable mechanical properties and performance relative to the implant tissue region.

Material composition and its associated mechanical, chemical, and even electrical and other physical properties are important relative to: compatibility and stability at the tissue implant site; controlled and proper tissue in-growth and to implement integration into the tissue, immuno-histo tissue response, and mechanical and visual appearance. The augmentation performance for the patient encompasses proper aesthetic outcome arising from the function of the physical components and the chemical composition of the composite of gel and particles implant. In particular, prior art implants utilizing gels have relied on the gel as a carrier but have failed to recognize and solve the problem of providing an implant with a gel which is designed to cooperate with the solid particles to mimic, both mechanically and chemically, the tissue into which it is injected and to behave in a symbiotic controlled manner when embedded in the tissue.

Implants using prior art gels exhibit a tendency to form nodules, or to migrate from the desired implantation location, or to undergo unwanted and undesired chemical and/or mechanical breakdown, such as phase separation or formation of unwanted geometries and cosmetic appearance in the body. None of these is an acceptable result for a patient. Nodule formation has been previously reported for known compositions by M. Graivier and D. Jansen, "Evaluation of a Calcium Hydoxylapatite-Based Implant (Radiesse) for Facial Soft-Tissue Augmentation," Plastic and Reconstructive Surgery Journal, Vol. 118, No. 3s, pg. 22s (2006).

SUMMARY OF THE INVENTION

The present invention is directed to systems and methods for preparation of implant materials which enable compatible tissue augmentation. In particular, the systems and methods relate to augmentation implants preformed in accordance with carefully preparing implant matrix materials using a precise protocol to manipulate a plurality of chemical variables to achieve a designed end product and with well define rheological characteristics. In one embodiment, the implants comprise gels having specific compatibility and stability at the tissue implant site; controlled and proper tissue in-growth to implement integration into the tissue, minimized immuno-histo tissue response, and improved mechanical and visual appearance. In one embodiment, the implant comprises gels having particles suspended therein with specific compatibility and stability at the tissue implant site; controlled and proper tissue in-growth to implement integration into the tissue, minimized immuno-histo tissue response, and improved mechanical and visual appearance. The implants have physical and chemical properties selected to achieve a desired rheological and chemical behavior when implanted. For example, it is preferable to replace or augment tissue structure with a material exhibiting physiological properties, including rheological, chemical, biological, and mechanical properties, which are similar to and/or compatible with those of the treated tissue and/or designed to accommodate tissue in growth in a controlled manner.

BRIEF DESCRIPTION OF THE DRAWINGS

FIG. 7B(ii) shows the same chemical variables versus G' at 0.7 Hz; FIG. 7B(iii) same but for G' at 4 Hz; FIG. 7B(iv) same but for frequency response at 0.7 Hz; FIG. 7B(v) same but for tan $\delta$ at 0.7 Hz; FIG. 7B(vi) same but for G" at 0.7 Hz; FIG. 7B (vii) same but G" at 4 Hz; and FIG. 7B(viii) same but for frequency response at 4 Hz.

FIG. 9A(ii) is CMC versus PBS versus viscosity at O.7 Hz with planar cross-sections for FIG. 9B shown; FIG. 9A(iii) is CMC versus PBS versus G' at O.7 Hz; FIG. 9A(iv) is CMC versus PBS versus G" at 0.7 Hz; FIG. 9A(v) is CMC versus PBS versus tan $\delta$ at 4 Hz; FIG. 9A(vi) is CMC versus PBS versus G' at 4 Hz; FIG. 9A(vii) is CMC versus PBS versus G" at 4 Hz; FIG. 9A(viii) is CMC versus PBS versus frequency response at 0.7 Hz; and FIG. 9($ix$) is CMC versus PBS versus frequency response at 4 Hz.

DETAILED DESCRIPTION OF THE PREFERRED EMBODIMENTS

Figure 1:
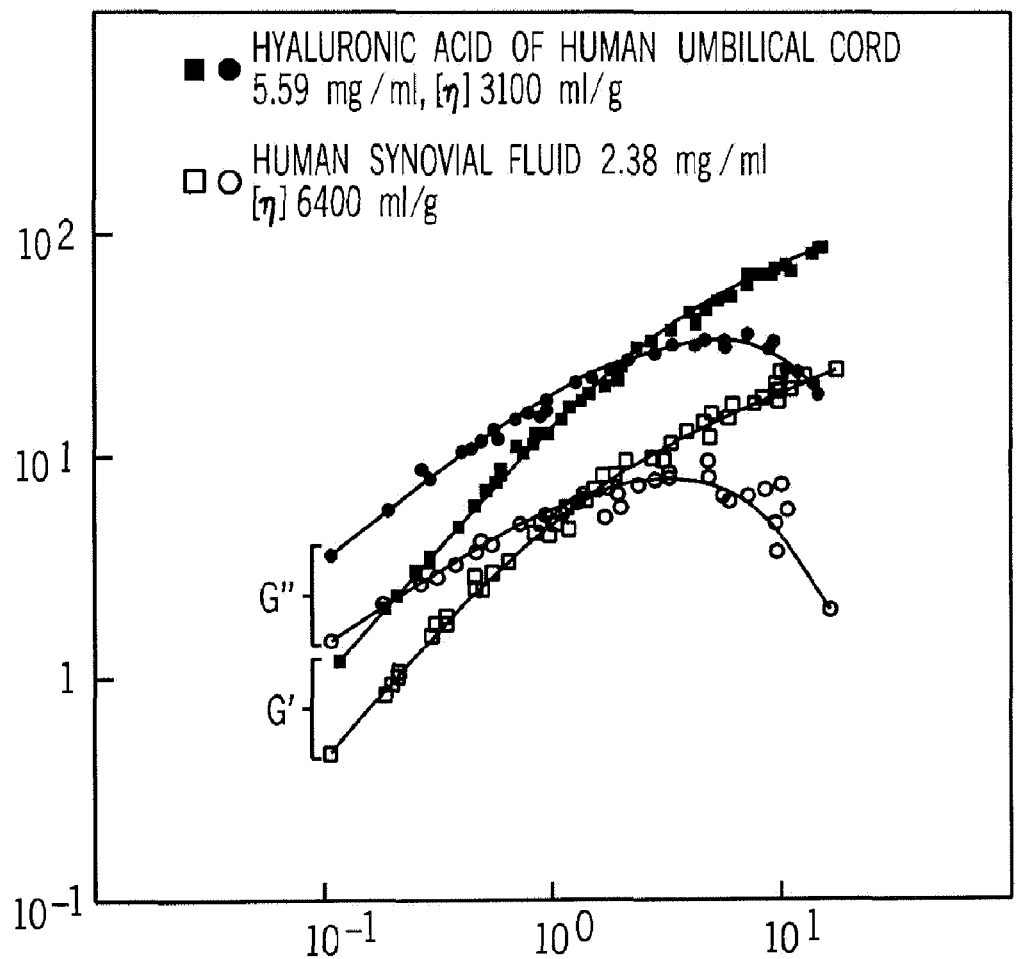
FIG. 1 illustrates behavior of G' and G" for two different body tissue fluids.

The present invention is directed to tissue augmentation implants and generally to programmable rheology polysaccharide gels. More particularly, the invention relates to polysaccharide compositions containing carboxymethylcellulose or other polysaccharide polymers formulated to exhibit rheological characteristics which are designed particularly to match the characteristics of the body tissue implant region of interest. For example, the invention can be applied to provide tissue implant product throughout the body, such as, for example, urinary tract, vocal fold, lip tissue, cheek, other dermal tissue for various uses including clinical and restorative applications and cosmetic applications like nasolabial folds, marionette lines, lip augmentation and wrinkles and folds. In considering tissue augmentation implants, it is important to understand that physical properties of body tissue are closely related to tissue function; and in one aspect tissue cell response to the rheological characteristics (e.g., elasticity) of their microenvironment must be properly accounted for. Understanding the physical structure and function of tissues is of fundamental and therapeutic interest. It is therefore most preferable to replace or augment tissue structure with a material exhibiting physical properties, including rheological, and also chemical and biological properties similar to those of the treated tissue. This provides improved tissue compatibility of the implant material and encourages normal cell responsiveness. In addition, the similar behavior of the implant and the surrounding tissue provides for a more natural appearance to the augmented area and also can more readily accommodate controlled tissue in-growth. The particular way in which the "similarity" of the implant rheology is determined and control of the product manufacture are important aspects of the invention. The details of the selection of the chemical and thermal treatment variables for the implant product and their mapping to appropriate rheological values will be described in detail hereinafter. Different tissues exhibit unique biomechanical and chemical characteristics associated with tissue functions; and the effects of tissue properties should be considered when augmenting or replacing these tissues. Consequently, the implant products are formulated to achieve the desired rheological properties to achieve tissue compatibility, as well as avoid unwanted chemical reactions and phase separation.

Carboxymethylcellulose ("CMC") and other polysaccharides are examples of material used in gel or solution which are used for a variety of medical and non-medical applications. Sodium carboxymethylcellulose ("NaCMC") is cellulose reacted with alkali and chloroacetic acid. It is one of the most abundant cellulose polymers available. It is water soluble and biodegradable and used in a number of medical and food applications. It is also commonly used in textiles, detergents, insecticides, oil well drilling, paper, leather, paints, foundry, ceramics, pencils, explosives, cosmetics and adhesives. It functions as a thickening agent, a bonder, stabilizer, water retainer, absorber, and adhesive.

A number of literature references describe carboxymethylcellulose and other ionic polysaccharides as being viscoelastic and pseudoplastic. See, for example: (Andrews G P, Gorman S P, Jones D S., Rheological Characterization of Primary and Binary Interactive Bioadhesive Gels Composed of Cellulose Derivatives Designed as Ophthalmic Viscosurgical Devices, Biomaterials, 2005 February; 26 (5): 571-80; Adeyeye M C, Jain A C, Ghorab M K, Reilly W J Jr., Viscoelastic Evaluation of Topical Creams Containing Microcrystalline Cellulose/sodium Carboxymethyl Cellulose as Stabilizer, AAPS PharmSciTech. 2002; 3 (2): E8; Lin S Y, Amidon G L, Weiner N D, Goldberg A H., Viscoelasticity of Anionic Polymers and Their Mucociliary Transport on the Frog Palate, Pharm. Res. 1993, March: 10 (3): 411-417; Vais, A E, Koray, T P, Sandeep, K P, Daubert, C R. Rheological Characterization of Carboxymethylcellulose Solution Under Aseptic Processing Conditions, J. Food Science, 2002. Process Engineering 25: 41-62).

The Aqualon Product Information publication from Hercules, Inc. describes the effects of various parameters on rheology of sodium CMC. Viscosity increases with increasing concentration, and CMC solutions are pseudoplastic and viscoelastic. Exposure to heat results in a reduction in viscosity and effects are reversible under normal conditions. After long periods of time, CMC will degrade at elevated temperatures with permanently reduced viscosity. For example, moderate MW (Aqualon 7L) CMC heated for 48 hours at 180° F. will lose 64% of viscosity. CMC is relatively stable to changes in pH and effects of pH on viscosity are minimal in the physiologically relevant range of pH 6-9. There is some loss of viscosity above 10 and some increase below 4. Salts may also affect rheology of CMC; and monovalent cations interact to form soluble salts. If CMC is dissolved in water and then salts are added, there is little effect on viscosity. If CMC is added dry to salt solution, the viscosity can be depressed through ionic repulsion. Polyvalent cations will not generally form crosslinked gels. Viscosity is reduced when divalent salts are added to CMC solution and trivalent salts precipitate CMC.

As can be concluded from consideration of the prior art, rheological and chemical properties of the implant involve many complex factors. As such, one can vary each of those components of the implant in order to design an implant with specific controlled in vivo properties. Such degrees of freedom are in fact so large and complex that designing the proper implant is a formidable task.

In order to resolve these complex tasks, it is instructive to consider the rheology of selected body tissue components. Shown in FIG. 1 are two different body tissue fluids composed of the same basic hyaluronic acid (sometimes referred to as hyluronic acid) component but that show significantly different storage and loss modulus under the same physiological strain conditions. Both solutions demonstrate shear thinning and the material conversion from a viscous material ($G''$ predominant or Tan $\delta > 1$) to an elastic material ($G'$ dominant) over a relatively small physiological shear stress of 0.1 to 180 radians/sec (0.159 Hz to 28.6 Hz).

Figure 2:
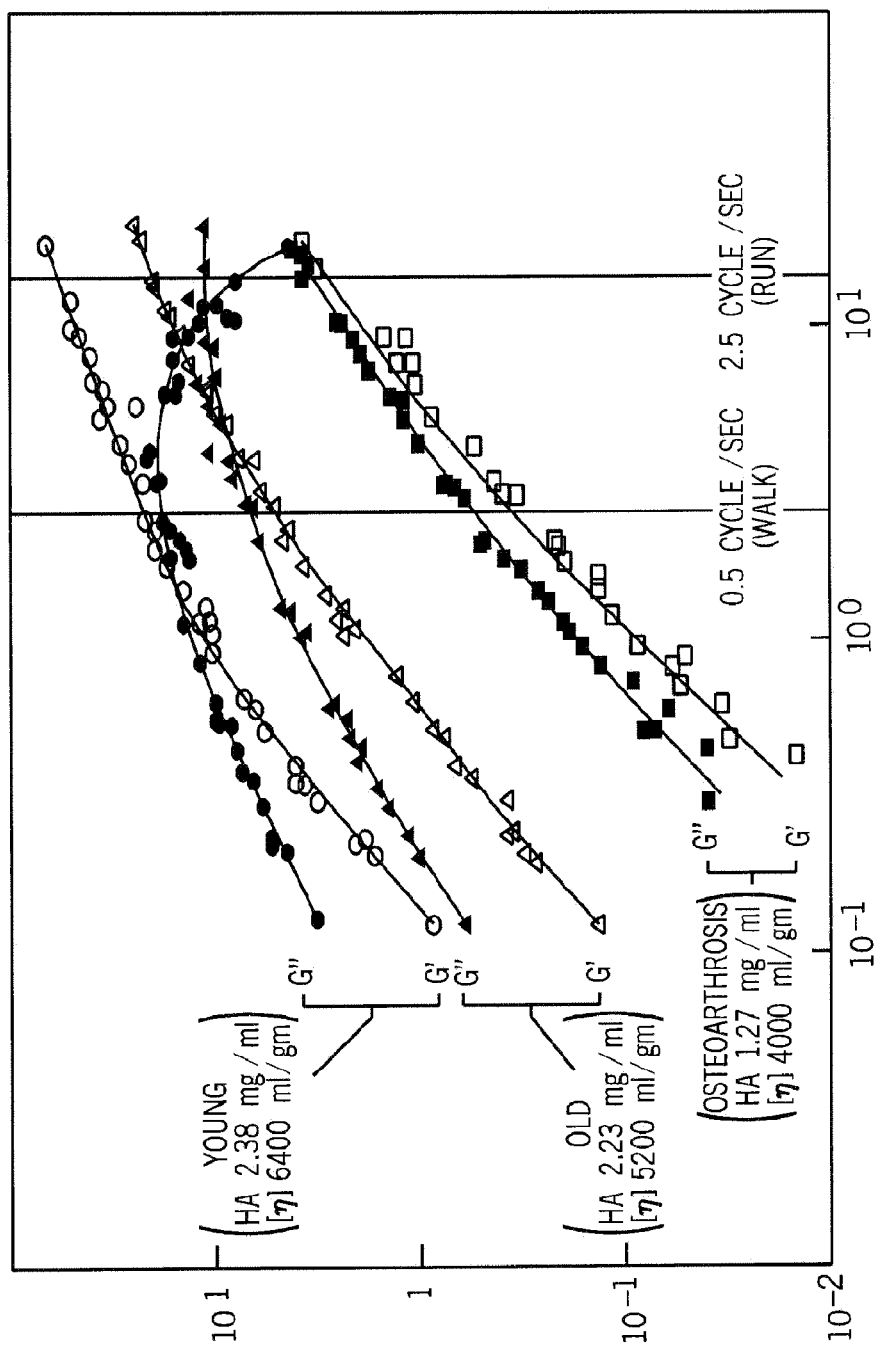
FIG. 2 illustrates G' and G" for three different age body tissue fluids.

For example, it has been demonstrated that physiological fluids conform to the stress imposed on them in varying ways. Dominant characteristics of a material can change from a viscous lubrication material to elastic anchoring character as outside forces are imposed. Shown in FIG. 2 are three of the same body tissue fluids composed of the same basic hyaluronic acid component but that show significantly different storage and loss modulus under the same physiological strain conditions based on the age of an individual. The materials labeled "young" and "old" demonstrate shear thinning and the material conversion from a viscous material ($G''$ predominant or tan $\delta > 1$) to an elastic material ($G'$ dominant) over a relatively small physiological shear stress of 0.1 to 180 radians/sec. Material cross-over ($G''=G'$) and relative amplitude is dependent on age. The material labeled "osteoarthritis" did not cross-over under the same shear conditions and the storage $G'$ and loss modulus $G''$ amplitudes were significantly less than the other two materials. Therefore, it is demonstrated herein through formulation and physical manipulation of the cellulose based implant that biologically relevant biomechanical gel properties can be manufactured that can be tailored for the specific application required. It is thus important to recognize this type of transition point for biological acceptance of materials. Various controlling parameters, such as implant product parameters can be manipulated, including buffer strength (such as PBS), polysaccharide choice and concentration (such as NaCMC), lubricant content (such as glycerin); and autoclave time can also be manipulated so that mechanical outputs of viscosity and elasticity may be adapted to the desired outcome without creating all of the problems apparent in the prior art.

For example, in one preferred embodiment of the present invention the method of manufacture and product are directed to implants for tissue augmentation of the lips. As stated earlier, physical properties of body tissue are closely related. Cellular propagation, cellular infiltration and cellular function during tissue repair has been shown across several cellular models to be dependent on the rheological characteristics (e.g., elasticity) of their microenvironment. As described hereinbefore, understanding the physical structure and function of tissues is of fundamental therapeutic interest during tissue augmentation and repair. It is therefore preferable to replace or augment tissue structure with a material exhibiting physical properties, including rheological, as well as chemical, biological, and mechanical properties, similar to those of the treated tissue. The implants therefore provide an opportunity to match the properties of the implant with that of the tissue in which the implant is to be placed. This provides improved tissue compatibility of the implant material and encourages normal cell responsiveness designed to provide controlled tissue in growth. In addition, the similar behavior of the implant and the surrounding tissue provides for a more natural appearance to the augmented area.

In one most preferred embodiment, the implant comprises gels of 2.6% CMC with 1.5% glycerin in a 25 mM phosphate buffer (PBS) at 7.4 pH. The phase angle ranged from 48 degrees to 140 degrees over the frequency range of 0.1 Hz to 10 Hz. This is consistent with published measurements for experimentally measured phase angle for the oblicularis oris superior and inferior under voluntary stimulation where the phase angle ranged from near 0 degrees to 150 degrees over the frequency range of 0.1 Hz to 10 Hz.

The magnitude of the initial phase angle is larger for the implant as the material demonstrates more viscous character at f<0.05. However, the material G'=G" cross-over is 0.2; and the elastic character starts to dominate so as to simulate the elastic behavior which has been experimentally measured in the art. For both the experimentally measured and the proposed implant the phase angle demonstrates little change over the frequency range of 0.1 Hz to 1 Hz with similar phase shifts noted over the same biologically relevant ranges.

In one embodiment, the implant comprises gels of 2.6% CMC with 1.5% glycerin in a 25 mM phosphate buffer at 7.4 pH with 30% v/v 25 um to 45 um calcium hydroxylapatite particles. The material rheology is similar to the tissue site, especially at low frequencies where the phase angle is linear. The material tests as an elastic material over the frequency range. However, the tan $\delta$ starts at 0.9 (approximately G'=G") and decreases as the material shear thins over the physiologically relevant range of 0.1 Hz to 10 Hz.

It is also useful to understand certain terminologies used herein; including "rheology", which is the study of the deformation and flow of matter. "Newtonian fluids" (typically water and solutions containing only low molecular weight material), the viscosity of which is independent of shear strain rate and a plot of shear strain rate. Non-Newtonian fluid is a fluid in which the viscosity changes with the applied shear force. The rheological outputs that describe a material are typically $\eta$, G', G", tan $\delta$ deflection angle relative to a linear force (shear) or oscillating force (Hz) of activity on the tissue at an implant site. The parameter $\eta$ is the viscosity, which is an indication of the materials measure of the internal resistance of a material to deform under shear stress. For liquids, it is commonly perceived as "thickness", or resistance to pouring. G' is the storage modulus, which is an indicator of elastic behavior and reveals the ability of the polymer system to store elastic energy associated with recoverable elastic deformation. G" is the loss modulus, which is a measure of the dynamic viscous behavior that relates to the dissipation of energy associated with unrecoverable viscous loss. The loss tangent (tan $\delta$) is defined as the ratio of the loss modulus to the storage modulus (G"/G') and is dimensionless. It is a measure of the ratio of energy lost to energy stored in a cycle of deformation and provides a comparative parameter that combines both the elastic and the viscous contribution to the system. A tan $\delta$ greater than 1 means the fluid is more liquid. A tan $\delta$ less than 1 means the fluid is more solid. Deflection angle is defined as the angle from a steady state after a force is applied to a material. The physiologically relevant range of shear force and oscillation force is the body tissue activity range for typical human function for that tissue. These ranges will be particularly evident, if a target implant is directed to soft dermal tissue, dense collagenous tissue, muscle or bone.

The biomechanical behavior of biomaterials can therefore be characterized by measuring their rheological properties. Rheology is related to viscoelasticity and viscoelastic shear properties. Viscoelastic shear properties are quantified by complex shear modulus which includes elastic shear modulus and viscous shear modulus. The magnitude of the complex shear modulus has been used to indicate overall shear elasticity, stiffness, and rigidity. If a material is purely elastic, then tan $\delta$=0. If the material is purely viscous, the tan $\delta$=infinity. All tissues exhibit a tan $\delta$ between these two extremes.

Different tissues exhibit unique biomechanical characteristics associated with tissue functions and the effects of tissue properties should be considered when augmenting or replacing these tissues. This invention describes compositions that are formulated to simulate the biomechanical properties of the tissues in which the compositions are injected or implanted and avoid unwanted chemical reactions and phase separation. Many different variables together provide the overall mechanical, chemical and biologic properties of the implant. As such, one may vary each of those components of the implant in order to design an implant with specific controlled in vivo properties. Sterility is a necessary design requirement. Therefore, the sterilization mode and parameters associated with the sterilization process are vital to the material design because the intended use of the material is for tissue augmentation or replacement.

The implant is a composite injectable into soft tissue. The composite material comprises a biocompatible gel with or without particles. Prior to and during injection, the gel functions, in part, as a carrier for particles which might be present. In vivo, the gel forms an integral part of the implant, providing the necessary pre-selected mechanical and chemical microenvironment previously described for the implant to achieve the desired article of manufacture.

As stated hereinbefore, the carrier preferably includes a polysaccharide gel wherein the polysaccharides that may be utilized in the present invention include, for example, any suitable polysaccharide and combinations thereof, within the following classes of polysaccharides: celluloses/starch, chitin and chitosan, hyaluronic acid, hydrophobe modified systems, alginates, carrageenans, agar, agarose, intramolecular complexes, oligosaccharide and macrocyclic systems. Examples of polysaccharides grouped into four basic categories include: 1. nonionic polysaccharides, including cellulose derivatives, starch, guar, chitin, agarose and. dextron; 2. anionic polysaccharides including cellulose derivatives starch derivatives, carrageenan, alginic acid, carboxymethyl chitin/chitosan, hyaluronic acid and xanthan; 3. cationic polysaccharides, including cellulose derivatives, starch derivatives guar derivatives, chitosan and chitosan derivatives (including chitosan lactate); and 4. hydrophobe modified polysaccharides including cellulose derivatives and alpha-emulsan. In one embodiment, the polysaccharide polymer is selected from the group of sodium carboxymethylcellulose, hydroxyethyl cellulose, ethylhydroxyethyl cellulose, carboxymethyl cellulose, carboxyethylhydroxyethyl cellulose, hydroxypropylhydroxyethyl cellulose, methyl cellulose, methylhydroxylmethyl cellulose, methylhydroxyethyl cellulose, carboxymethylmethyl cellulose, and modified derivatives thereof. Preferred polysaccharides for use in the present invention include, for example, agar methylcellulose, hydroxypropyl methylcellulose, ethylcellulose, microcrystalline cellulose, oxidized cellulose, chitin, chitosan, alginic acid, sodium alginate, and xanthan gum. In certain embodiments, more than one material may be utilized to form the gel, for example two or more of the above listed polysaccharides may be combined to form the gel. In certain embodiments, more than one material may be utilized to form the crosslinked gel, for example two or more of the above listed polysaccharides may be combined to form the gel.

In addition, the gel may be crosslinked. Appropriate gel crosslinkers include for example: heat, pH, and crosslinking through mono valent, di-valent, and tri-valent cationic interactions. The crosslinking ions used to crosslink the polymers may be anions or cations depending on whether the polymer is anionically or cationically crosslinkable. Appropriate crosslinking ions include, but are not limited to cations selected from the group consisting of calcium, magnesium, barium, strontium, boron, beryllium, aluminum, iron, copper, cobalt, and silver ions. Anions may be selected from but are not limited to the group consisting of phosphate, citrate, borate, carbonate, maleate, adipate and oxalate ions. More broadly, the anions are derived from polybasic organic or inorganic acids. Preferred crosslinking cations are calcium iron and barium ions. The most preferred crosslinking cations are calcium and iron. The preferred crosslinking anions are phosphate, citrate and carbonate. Crosslinking may be carried out by contacting the polymers with an aqueous solution containing dissolved ions. Additionally, crosslinking could be accomplished through organic chemical modification including: poly-functional epoxy compound is selected from the group consisting of 1,4-butanediol diglycidyl ether (BDDE), ethylene glycol diglycidyl ether (EGDGE), 1,6-hexanediol diglycigyl ether, polyethylene glycol diglycidyl ether, polypropylene glycol diglycidyl ether, polytetramethylene glycol digylcidyl ether, neopentyl glycol digylcidyl ether, polyglycerol polyglycidyl ether, diglycerol polyglycidyl ether, glycerol polyglycidyl ether, tri-methylolpropane polyglycidyl ether, pentaerythritol polyglycidyl ether, and sorbitol polyglycidyl ether. Additionally, crosslinking could be accomplished through organic chemical modification through the carbonyl or hydroxide functionality of the polysaccharide backbone reaction. In embodiments utilizing more than one type of polymer, the different polymers may crosslink with each other to form further crosslinking.

As shown by the Example 19, the discussion regarding FIG. 9B, and data provided hereinafter, in one embodiment the implant comprises a gel, the tan $\delta$ (ratio of the viscosity modulus G" to the loss modulus G') of which can be manipulated by adjusting the concentration of salt (in this case potassium phosphate or PBS) in NaCMC formulations that are subsequently heat sterilized. In compositions prepared in water, the tan $\delta$ is <1 before and after heat treatment indicative of a elastic fluid. If the compositions are prepared in dilute salt solutions, the tan $\delta$ is <1 before heat treatment and >1 after heat treatment. A tan $\delta$>1 generally indicates a viscous fluid. Both dilute salt (in this case monovalent) and heat treatment are needed to convert the composition from a tan $\delta$<1 to a tan $\delta$>1. As the salt concentration increases, the viscosity of the composition is reduced by reducing the ability of the polysaccharide to internally crosslink.

In selected compositions for tissue augmentation a viscosity is preferred that will provide some bulking capability in addition to satisfying tissue rheological behavior. Therefore, the salt concentration is preferably carefully controlled at relatively low levels, usually less than 100 mM.

The addition of glycerin to salt solution reduces the tan $\delta$ i.e., the composition, even after heat treatment, remains elastic, because the rheological properties of the glycerin provide bulking rheological interaction with the polysaccharide gel. The tan $\delta$ is preferably and usually <I. However, the tan $\delta$ of this composition is different from the tan $\delta$ of compositions prepared in water without salt. The rheological characteristics of NaCMC can be manipulated by salt, glycerin, and heat treatment.

In addition to the desire to accommodate the rheological character of the implant tissue site, the gel of the present invention can be adjusted to control extrusion, decomposition rate (chemical and physical), moldability and porosity to modulate tissue response. Gel characteristics also control varying rates of resorption, as host tissue forms around the slower resorbing ceramic particles.

In one embodiment, the present invention provides a gel capable of supporting solid particles for injection through fine gauge needles and forming an integral and compatible part of the implant (and surrounding bio-environment) once injected. The implant includes particles suspended in the gel. In certain embodiments, the particles are ceramic based composites. Particulate ceramic materials include, but are not limited to, calcium hydroxyapatite, and other suitable materials including, but are not limited to, calcium phosphate-based materials, and the like. Examples include, but are not limited to, tetracalcium phosphate, calcium pyrophosphate, tricalcium phosphate, octacalcium phosphate, calcium fluorapatite, calcium carbonate apatite, alumina-based materials, and combinations thereof. The ceramic particles may be smooth rounded, substantially spherical, particles of a ceramic material embedded in a biocompatible gel material that is continuous, crosslinked or in a dehydrated configuration as discussed below. In this embodiment, particles may range in size 20 microns to 200 microns and preferably from about 20 microns to 120 microns and most preferably from 20 microns to 45 microns. Concentration of ceramic particles ranges from 5% to 65%, by volume, preferably from 10% to 50% by volume and most preferably from 30% to 45% by volume.

Particles which can be added to the gel can be made of a biocompatible but non-biodegradable material. Suitable materials include glass, e-PTFE, PTFE, polypropylene, polyacrylamide, polyurethane, silicone, polymethylmethacrolate, Dacron, carbon particles, TEFLON®, metals of iron, copper nickel titanium alloys thereof including Nitinol, silver, gold, platinum, or stainless steel. The particles can be comprised of a plurality of layers of materials including organic polymers and proteins. Additionally, one can select particles from organic biopolymers of elastomers such as, for example, acrylic polymers, vinyl alcohol polymers, acrylate polymers, polysaccharides, the acrylic family such as polyacrylamides and their derivatives, polyacrylates and their derivatives as well as polyallyl and polyvinyl compounds. All of these polymers are crosslinked so as to be stable and non-resorbable, and can contain within their structure other chemicals displaying particular properties or mixtures thereof. The particles may preferably include a polysaccharide particle, for example, any suitable polysaccharide and combinations thereof, within the following classes of polysaccharides: celluloses/starch, chitin and chitosan, hyaluronic acid, hydrophobe modified systems, alginates, carrageenans, agar, agarose, intramolecular complexes, oligosaccharide and macrocyclic systems. Examples of polysaccharides can be grouped into four basic categories and include: 1. nonionic polysaccharides, including cellulose derivatives, starch, guar, chitin, agarose and. dextron; 2. anionic polysaccharides including cellulose derivatives starch derivatives, carrageenan, alginic acid, carboxymethyl chitin/chitosan, hyaluronic acid and xanthan; 3. cationic polysaccharides, including cellulose derivatives, starch derivatives guar derivatives, chitosan and chitosan derivatives (including chitosan lactate); and 4. hydrophobe modified polysaccharides including cellulose derivatives and alpha-emulsan. In one preferred embodiment, the polysaccharide polymer is selected from the group of sodium carboxymethylcellulose, hydroxyethyl cellulose, ethylhydroxyethyl cellulose, carboxymethyl cellulose, carboxyethylhydroxyethyl cellulose, hydroxypropylhydroxyethyl cellulose, methyl cellulose, methylhydroxylmethyl cellulose, methylhydroxyethyl cellulose, carboxymethylmethyl cellulose, and modified derivatives thereof. Preferred polysaccharides for use in the present invention include, for example, agar methylcellulose, hydroxypropyl methylcellulose, ethylcellulose, microcrystalline cellulose, oxidized cellulose, chitin, chitosan, alginic acid, sodium alginate, and xanthan gum. In certain embodiments, more than one material may be utilized to form the particle, for example two or more of the above listed polysaccharides may be combined to form the particle. In certain embodiments, more than one, such as two or more polysaccharide materials can be utilized in conjunction with those crosslinking agents previously listed herein, to form the crosslinked particle. Further, particles, beads, microbeads, nanoparticles and liposomes that may be suspended in gels may be porous, textured, coated, and solid surfaces and can be round or other configurations.

These material compositions of the gel allow for better extrusion characteristics through needle gauges as small as 27 to 30 gauge without the use of mechanical assistance devices, and with less frequency of jamming or occlusion not previously accomplished in prior art. While gels having particles suspended therein will clearly have different extrusion characteristics than if there were no particles, the implants of the present invention having particles suspended in gel exhibit improved extrusion over those of the prior art. As particle size approaches that of the needle, extrusion becomes increasing difficult. However, particle sizes below 75 microns allow for implants of the present invention to be injected through fine gauge needs (such as 27 to 30 gauge). The gel is able to suspend the particles as a carrier and allow for less force to extrude the implant with a lower likelihood of occlusion. Material compositions with a higher tan δ in the range of 0.5 to 3.5 and most preferably between 0.5 and 2.0 demonstrate the best performance characteristic for extrusion through needle gauges as small as 27 to 30 gauge. Material with higher tan δ are more preferable for instances where mobility is the key parameter. Decreasing tan δ creates more stout, moldable implant materials. Some examples of extrusion forces for CaHA loaded gel are in Table 1 below.

TABLE 1

| Physical parameters/ Material composition | 30% CaHA— 3.25 CMC; 15% glycerin | 30% CaHA— 2.6% CMC; 1.5% glycerin | 40% CaHA— 2.6% CMC; 1.5% glycerin |
|---|---|---|---|
| Extrusion Force (lbf, 0.5" 27 Ga.) | 6.1 | 5.4 | 4.8 |
| Extrusion Force (lbf, 1.25" 27 Ga.) | 11.5 | 9.8 | 7.6 |

The preferred embodiment demonstrates substantially less required force than conventional systems.

In one embodiment, the present invention provides a gel capable of supporting semi solid particles for injection through fine gauge needles and forming an integral and compatible part of the implant (and surrounding bio-environment) once injected. The implant includes particles suspended in the gel. In certain embodiments, the particles are excessively crosslinked polysaccharide based composites. Particulate materials include, but are not limited to, CMC, agar and other suitable materials including, but are not limited to, alginate, hyaluronic acid, chitosan and compositional combinations of the like. Examples include, but are not limited to, hyaluronic acid/CMC, alginate/CMC and chitosan/CMC ionically and chemically crosslinked combinations thereof. The particles may be smooth rounded, substantially spherical, particles embedded in a biocompatible gel material that is continuous, crosslinked or in a dehydrated configuration as discussed below. In this embodiment, particles may range in size from about 20 microns to 200 microns, and preferably from 20 microns to 120 microns and most preferably from 20 microns to 45 microns. Concentration of particles ranges from 5% to 90%, by volume, preferably from 10% to 80% by volume and most preferably from 60% to 70% by volume.

Furthermore, slight compositional changes in the gel carrier allows selection of the biocompatibility parameters previously described, while still allowing for homogenous particle suspension. Tissue specific proteins may be added to facilitate tissue response either by acceleration (infiltration of extra cellular matrix or collagen) or decreasing the immuno histological response. Such careful selection of these biocompatibility characteristics enable achieving a preselected shape, cosmetic appearance, chemical stability and bioenvironment to achieve stability of the implant or tissue in-growth depending on the application. Increased biocompatibility and biomechanical capability allows for the implant to degrade into compounds native to the body according to a specific degradation profile.

In one embodiment, a decrease in glycerin content has provided for an improved osmolarity range that is physiologically more similar to normal tissue physiological conditions with improved biocompatibility not previously reported in the prior art. The preferred form of the implant of the present invention does not rely on high amounts of glycerin to suspend the particles, as prior art gels have done. Despite this, the gels of the present invention are able to suspend a higher concentration of particles than previously taught even in prior art gels which relied heavily on glycerin content. The decrease in glycerin content enables the preferred embodiments to have a osmolarity range of 255 mOs to 600 mOs, preferable 255 mOs to 327 mOs, which is closer to the physiological osmolarity of blood of 280 to 303 mOs and is generally accepted as the range for cellular compatibility. Control of the parameter is one degree of freedom in achieving the above recited selection of a biocompatible implant. This preferred embodiment is described in tabular form in Table 2.

TABLE 2

| Physical parameters/ Material composition | 30% CaHA— 3.25 CMC; 15% glycerin | 30% CaHA— 2.6% CMC; 1.5% glycerin | 40% CaHA— 2.6% CMC; 1.5% glycerin |
|---|---|---|---|
| Osmolality (mmol/kg) | 1768 to 2300 | 291 | 289 |

This preferred embodiment is substantially more similar to normal physiological conditions than any conventional product.

In addition, the decrease in glycerin and CMC allows for material rheologies of preferred implant products that approach these physiological conditions or physiological conditions of other extra cellular matrixes and bodily fluids. The lower viscosity modulus $G''$ and loss modulus $G'$ allow for better tissue simulation at stress/strain amplitudes typical to target tissue in the human body.

The decrease in glycerin content also enables the preferred embodiments to have a water content range of 57.9% to 70.3%, which is closer to the physiological dermal water content of 70% in embryonic skin to 60% in more mature skin. Materials that are intended for tissue implantation that are closer to the physiological water content of the target tissue create less osmotic stress to the tissues and cells immediate to the implant.

Another controllable degree of freedom in constructing an implant to be biocompatible, as explained in detail herein before, is control of CMC concentration. The decrease in CMC concentration enables the preferred embodiments to have a thinner supporting gel matrix which allows for more particle movement during the injection and post injection which more closely mimics certain native tissue. It has been demonstrated that formulation adjustment within the gel allows for increasing the bulking material composition while still maintaining biologically relevant rheological characteristics. This facilitates improved baseline correction and improved durability in the soft tissue corrections while maintaining application standards consistent with the intended application. This creates less regional tissue stress and strain which, in turn, limits the immuno histological response in the form of erythema and edema thereby reducing recovery time.

As stated hereinbefore, implants described herein may be used in many parts of the body for tissue augmentation. For example, soft tissue that can be augmented by the implant includes but is not limited to dermal tissue (folds and wrinkles), lips, vocal folds, mucosal tissues, nasal furrows, frown lines, midfacial tissue, jaw-line, chin, cheeks, and breast tissue. It will be appreciated that each of these areas exhibit unique mechanical and biological properties. For example, the upper and lower lip exhibit continuous mobility and require an implant that provides similar mobility because of the muscle interaction and the decreased need for elasticity. Thus implants exhibiting such characteristics provide for both a higher degree of biocompatibility, mechanical compatibility, and a superior visual effect. As such, the implant may be formulated so as to be specifically designed for implantation within a particular portion of the body for addressing a particular indication. Table 3 illustrates the tan δ for vocal folds and skin in the young and the elderly.

For typical dermis applications outside the face, the rheological response for characterization may be better defined by $G'$, $G''$ or tan δ. This is summarized in Table 3 below, and these particular rheological parameters are preferably used to define regions of merit or volumes in desirability plots described hereinafter.

TABLE 3

Tan δ for Intact Tissues

| Tissue | Tan δ | Reference |
|---|---|---|
| Vocal fold (human) | 0.1-0.5 (0.2-0.5 at low frequency) (0.1-0.3 at high frequency) | Chan, R W and Titze, I R. 1999. J. Acoust. Soc. Am., 106: 2008-2021 |
| Human Dermis- 23 year old | 0.61 (strain rate 10% per minute) 1.02 (strain rate 1000% per minute) | Estimated as ratio of slopes of viscous modulus to elastic modulus from incremental stress-strain curves (Silver, F H, Seehra, G P, Freeman, J W, and DeVore, D P. 2002. J. Applied Polymer Science, 86: 1978-1985) |
| Human Dermis- 87 year old | 0.36 (strain rate 10% per minute) 1.16 (strain rate 1009% per minute) | See above |

Examples of preferred parameters for selected material compositions are set forth below in Table 4.

TABLE 4

| Physical parameters/ Material composition | 30% CaHA— 3.25 CMC; 15% glycerin | 30% CaHA— 2.6% CMC; 1.5% glycerin. | 40% CaHA— 2.6% CMC; 1.5% glycerin |
|---|---|---|---|
| Tan δ @ 0.5 Hz, 2τ 30degree C. | 0.453 | 0.595 | 0.581 |

Materials with higher tan δ are more preferable for instances where mobility is the key parameter. Decreasing tan δ creates more stout, moldable implant materials. The preferred embodiment demonstrates closer physiological response than conventional product materials.

For example, for addressing indications where the tissue exhibits lower viscosity, such as the lips, an implant having a viscosity of between 100,000 centipoise and 300,000 centipoise at 0.5 Hz with a tan δ between 0.5 and 1 may be used. Likewise, for addressing indications where a higher viscosity implant is desired such as facial contouring in the midfacial area or other areas where the implant preferably provides structural support, an implant having a viscosity of between 300,000 centipoise and 600,000 centipoise with a tan δ between 0.5 and 1 may be used. This is summarized in Table 5 below.

TABLE 5

| Physical parameters/ Material composition | 30% CaHA— 3.25 CMC; 15% glycerin | 30% CaHA— 2.6% CMC; 1.5% glycerin | 40% CaHA— 2.6% CMC; 1.5% glycerin |
|---|---|---|---|
| Viscosity (η @ 0.5 Hz) | 413750 | 202865 | 396585 |
| Tan δ @ 0.5 Hz | 0.453 | 0.595 | 0.581 |
| Viscosity modulus ($G'$ @ 0.5 Hz) | 1478.60 | 678.32 | 1331.8 |
| Loss Modulus ($G''$ @ 0.5 Hz) | 671.69 | 404.30 | 773.23 |

The tan δ of human vocal fold tissue ranges from 0.1-0.5 indicative of an elastic material (Chan, R W and Titze, I R, Viscoelastic shear properties of human vocal fold mucosa: Measurement methodology and empirical results". 1999, 1. Acoust. Soc. Am. 106:2008-2021). The tan δ of human skin ranges from 0.36 (older skin) to 0.61 (younger skin) (Calculated from stress-strain data—Silver, F H, Seehra, G P, Freeman, J W, and DeVore, D P. 2002. J. Applied Polymer Science, 86:1978-1985). The tan δ for skeletal muscles exceeds 1.0 indicative of a viscous material. The tan δ for hyaluronic acid ranges from 1.3 to 0.3 as the material demonstrates shear thickening and transitions through tan δ equal to 1 between 1 and 8 rad/s (0.17 to 1.3 Hz) (Fung Y C, 1993 "Biomechanics: Mechanical properties of living tissue", Second edition, Springer-Verlag, New York, N.Y.). This is important when designing a composition to augment human lips (muscle). There is even a difference in stiffness (more elastic according to Chan and Titze, et. al) between the upper and lower lips and between males and females. The lower lip is stiffer than the upper lip and male lips are stiffer than female lips (Ho, T P, Azar, K, Weinstein, and Wallace, W B. "Physical Properties of Human Lips: Experimental Theoretical Analysis", 1982. J. Biomechanics. 15:859-866). The present invention describes compositions that can be formulated to a rheology (including tan δ) that more closely simulates the tissue into which the biomaterial is placed.

Human lips are primarily composed of skeletal muscle surrounded by loose connective tissue covered by stratified keratinized squamous (similar to the stratum corneum of skin). There is a difference in the stiffness of the lower and upper lip. Many references equate stiffness to elasticity. If lip tissue is similar to skeletal muscle, lip tissue exhibits significant elasticity. However, a composition with a higher tan δ may result in fewer lip nodules, a common problem with prior art implants. Tissue responses to any implant depend on several factors including the chemical composition, physical configuration and biomechanical characteristics of the implant material and on the biomechanical forces of the micro environment of the host tissue. Prior art CaHA/CMC compositions injected into tissues under increased mechanical stress produce more collagenous tissue (which may lead to undesired tissue in-growth in certain applications) than when implanted in tissues under less mechanical stress. Part of this response is related to the viscoelasticity of the implant. An implant under continuous mechanical stress will react differently depending on the viscoelastic properties of the implant. A highly viscoelastic implant (low tan δ) will continuously undergo shear thinning to a lower viscosity and "recoil" to the initial higher viscosity. This continuous change in implant mechanics may "turn on" or signal host cells to become more active and to produce more collagen than an implant exhibiting more viscous rheology (higher tan δ). More viscous implants will not undergo the same level of mechanical flux compared to more viscoelastic implants.

For prior art compositions, thick collagenous material has been observed to encapsulate individual particles. The implant does form a continuous mass between muscle bundles (looks like muscle bundles were pushed apart) and particles are surrounded by a thick fibrous ring with thinner collagen units integrating between particles. In contrast, it has been observed in dermis and mucosal areas that collagen integration appears as a continuous weave between particles and not as a thick capsule around individual particles. This thick collagenous material around individual particles is similar to that observed in a lip nodule biopsy. This encapsulation is likely related to the continuous biomechanical forces in lip muscle, the elasticity and cohesiveness of the material, and accumulation between muscle bundles.

Thus, while not limiting the scope of the invention a composition with a higher tan δ may reduce the incidence of early nodules (those apparently associated with initial inflammatory response and foreign body response to engulf and remove CMC) and of later nodules resulting from excess fibrous tissue surrounding CaHA particles. A less elastic and lower viscosity composition can provide a smoother flowing and more intrudable implant with reduced biomechanical motion to signal host cells, thereby resulting in fewer nodules.

In addition to a base implant product and also selectively the use of filler materials, such as ceramics like CaHA, any number of medically useful substances for treatment of a disease condition of a patient can be added to the implant composition at any steps in the mixing process. Such substances include amino acids, peptides, vitamins, co-factors for protein synthesis; hormones; endocrine tissue or tissue fragments; synthesizers; angiogenic drugs and polymeric carriers containing such drugs; collagen lattices; biocompatible surface active agents, antigenic agents, cytoskeletal agents; cartilage fragments, living cells such as chondrocytes, bone marrow cells, mesenchymal stem cells, natural extracts, transforming growth factor (TGF-beta), insulin-like growth factor (IGF-1); growth hormones such as somatotropin; fibronectin; cellular attractants and attachment agents. In addition, lidocaine and other anesthetic additions to the gel are in the range of 0.1% to 5% by weight, more preferably 0.3%-2.0% and most preferably 0.2%-0.5%.

Manufacture of a Preferred Embodiment

Figure 3:
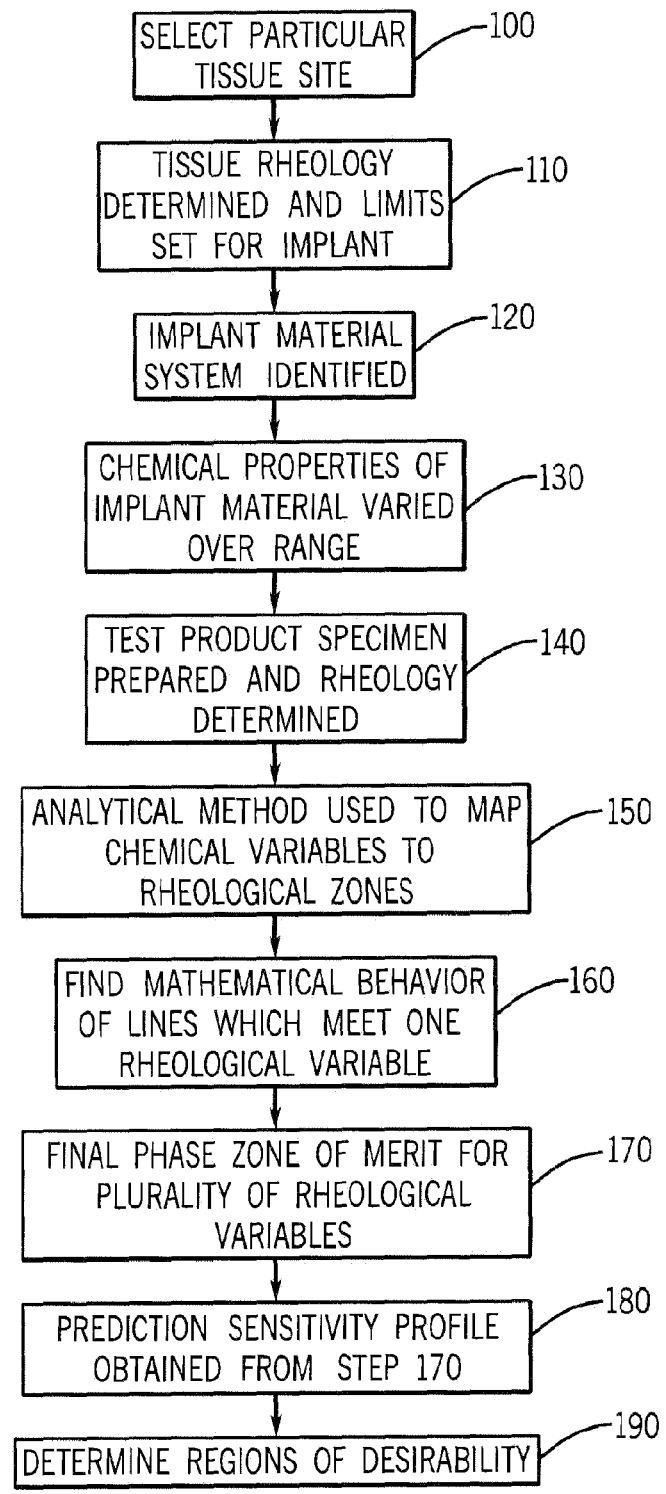
FIG. 3 illustrates a schematic method of manufacture of implant products.
Figure 4:
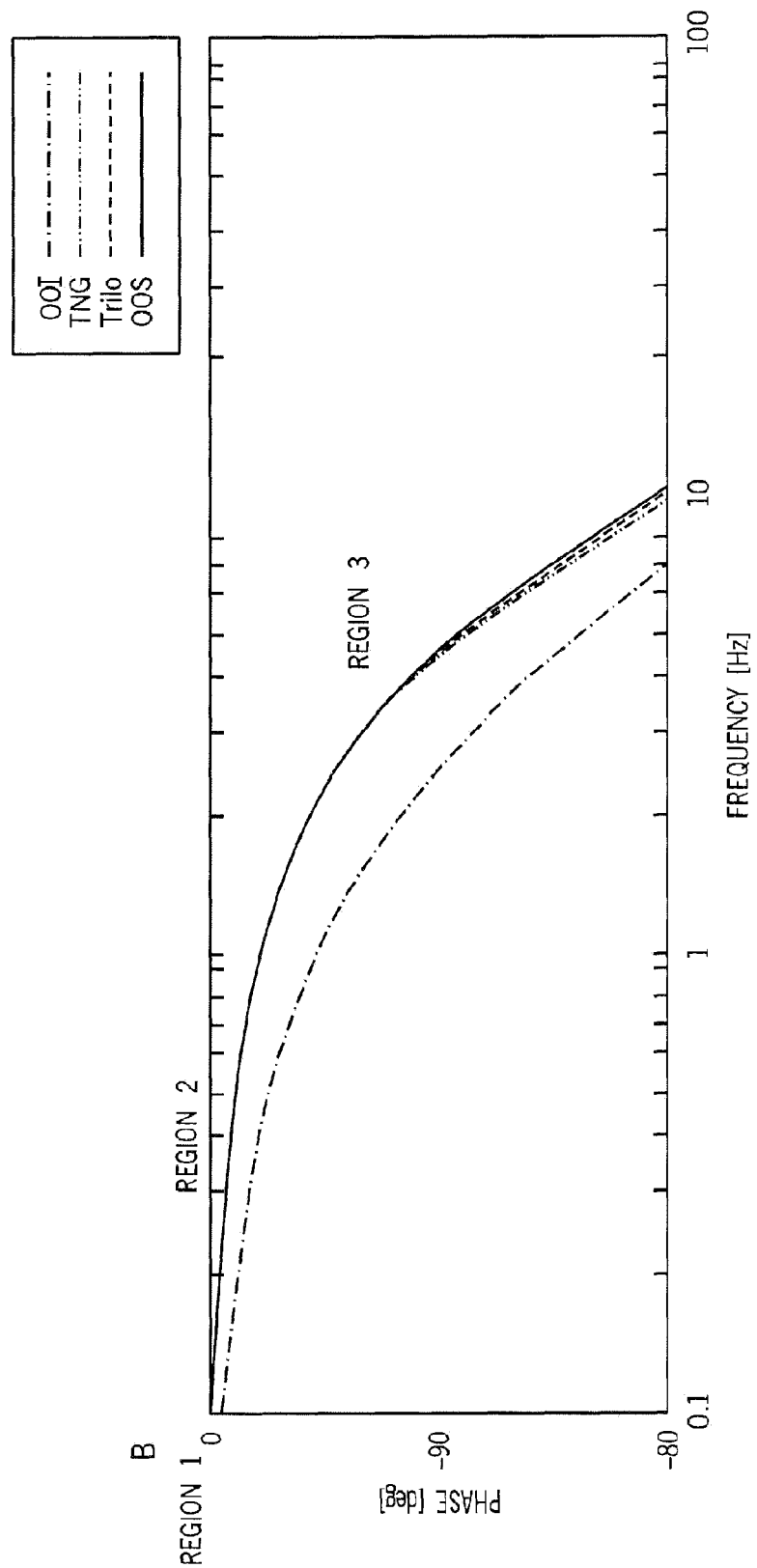
FIG. 4 illustrates phase angle versus frequency behavior of lip tissue.

In order to carry out a proper design and manufacture of the implant material, rheological parameters are selectively established to achieve an implant product targeted for a particular tissue site. In order to describe this process in detail, reference will be made to FIG. 3 which sets forth the method in a stepwise manner. In a first step 100, one selects a particular tissue site for the implantation. For example, tissue sites can include lip tissue, dermis and harder tissue, such as muscle tissue. The tissue sites can be characterized by their rheological response to stress over a range. For lip tissue as shown in FIG. 4, there are three regions of activity. In Region 1 for an initial small stress (0.1 Hz,), the phase angle, demonstrates the material to be elastic or muscle-like (range 0 to 5) and is linear in character. The larger the initial phase angle, the less dominate the character of the muscle/tissue interaction or the softer the tissue (such as dermis). In Region 2, the general increase in stress results in limited phase angle change. Muscle contraction does not dominate the elastic character of muscle and has not exceeded the muscle tissue elastic limit. In Region 3, the general increase in stress results in phase angle change. Stress starts to dominate the elastic character of the muscle tissue limit. The physiologically relevant range for stress is 0.1 Hz to 10 Hz. Optimization for dermal filler applications in the lip require consideration of the movement of muscles and soft bulbous tissue. Lip morphology is primarily directed by muscle interaction with soft tissue. Lip contractions are controlled by small sets of muscle: tissue nodes in multiple planes and dimensions. A dermal filler for the lip should then be most preferably viscoelastic. The material should be viscous under smalls stresses and gradually become elastic. The elastic character is essential so that the material stays where implanted. Amplitudes for G' & G" should be within the physiological range of similar ECM polysaccharides (See Fung Y C, 1993 "Biomechanics: Mechanical Properties of Living Tissue", Second Edition, Springer-Verlog, New York, N.Y.) and may range from 10 cps to 300 cps. This is summarized in Table 6 below.

TABLE 6

| Physical parameters/<br>Material composition | 3.25 CMC;<br>15% glycerin | 2.6% CMC;<br>1.5% glycerin |
|---|---|---|
| G' Range O.I Hz to 10 Hz | 86 cps to 530 cps | 21 cps to 238 cps |
| G" Range O.I Hz to 10 Hz | 66 cps to 262 cps | 26 cps to 154 cps |
| Tan δ Range O.I Hz to 10 Hz | 0.77 to 0.49 | 1.19 to 0.647 |

A material that maintains or more closely approximates the range of G' and G" values would be preferred. The preferred embodiment demonstrates a response that is substantially more similar to a normal physiological response than any conventional product.

In a second step 110, rheological properties of the selected tissue site are determined and proper limits of these rheological properties should be established. Consequently, data must be accumulated (either by direct experimental tests or by reference to published data) to define the range of tissue rheology and behavior during its use.

Figure 5:
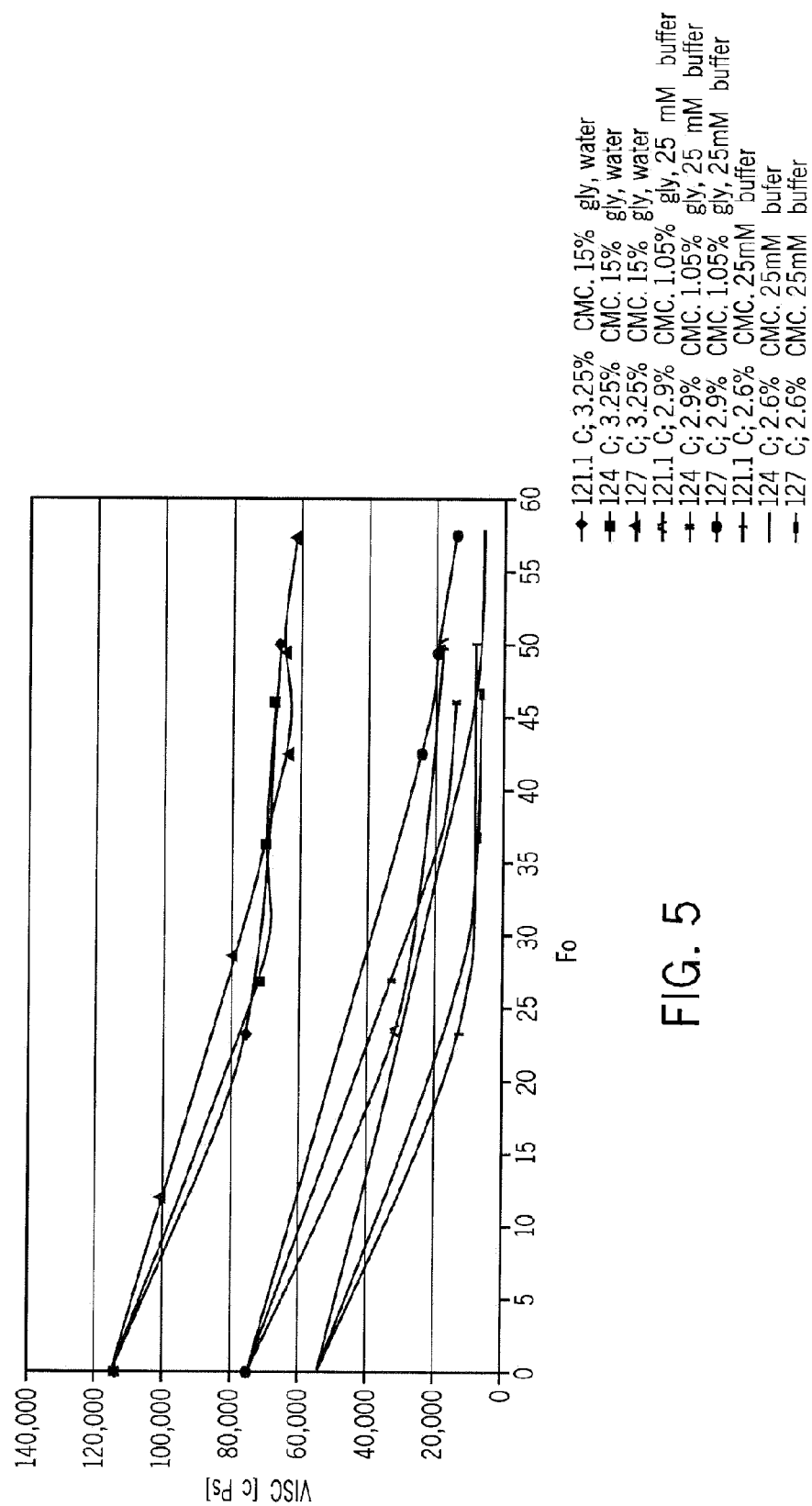
FIG. 5 illustrates Fo behavior versus viscosity for representative implant products.

In a next step 120, the implant material system is identified, and in general, it is important to satisfy several requirements in order to achieve a desirable rheology and avoid chemical breakdown or phase separation. Initially, it is desirable to select a polysaccharide based gel that can establish good chemical stability in the body. In addition, the gel can be combined with buffer and lubricants and properly sterilized to enable creating an implant with acceptable rheological behavior over the parameters of body tissue use. An example of one such preferred system includes a NaCMC polysaccharide gel, a buffer such as PBS, and a lubricant, such as glycerin. The composite material when sterilized achieves Fo values from about 22 and above and most preferably from about 24-33 which provides a value of about $10^{-6}$ sterility. The implant viscosity versus Fo is shown in FIG. 5.

Other implant components are also useful and would most preferably include other polysaccharides which have been described before, such as, celluloses/starch, chitin and chitosan, hyaluronic acid, hydrophobe modified systems, alginates, carrageenans, agar, agarose, intramolecular complexes, oligosaccharide and macrocyclic systems. In addition, any physiologically acceptable buffer can be employed, such as and not limited to glycine, citrate, and carbonate. A lubricant can also be employed, such as for example and not limited to, mineral oils and complex fatty acids. All these components must be adjusted by applying rigorous manufacturing standards described hereinafter which enable achieving the prescribed rheological parameter over the range of use of the particular tissue site.

In a next step 130, the chemical parameters of the selected implant material are varied to achieve a relatively broad range of rheological behavior. These chemical parameters are selected to cover such a reasonably broad range to insure the downstream analyzation process is able to identify the full range of useful chemical compositions from among the universe of possibilities. As will be described and illustrated graphically hereinafter, this broad set of chemical values enables analytical isolation of phase zones or regions of merit where the chemical characteristics map to an implant material having rheological behavior fitted to the selected recipient tissue site.

As noted hereinbefore, prior art implant products have serious deficiencies. For example, in one type of polysaccharide gel based implant for lip tissue, the implant tends to undergo chemical reaction or phase separation occurs, causing accumulation in nodules causing an irregular bumpy appearance in the lip tissue. These and other known products, as shown hereinafter, are outside the proper rheological phase zone or region of merit. The known implants do not demonstrate viscous behavior over the physiologically relevant ranges (about 0.1-10 Hz for stress) and therefore do not crossover G"=G' or tan δ>1. The prior art implants are thicker (i.e., more viscous) and cause an increased inflammatory response as the body increasingly recognizes the material as foreign hyaluronic acid. In yet another example of a prior art product, the material is based on highly crosslinked hyaluronic acid or hyaluronic acid particles which have G' and G" plots that do not cross-over resulting in a deficient implant.

After step 130, which includes identification of the chemical parameters and selecting a broad range of chemical implant values, in step 140 test product specimens are prepared over a broad range and their rheological character is determined. The matrix of rheological values includes frequency responses as a function of frequency (registered as phase angles), elastic modulus G'; viscosity modulus G"; tan δ (GIG") and viscosity over the body tissue variable range of interest. A comparative analysis between material compositions can then be performed to isolate the phase region of merit by methods described hereinafter.

As noted above, experimental data have been taken for a substantial matrix of chemical variables and the end rheological parameters determined. Various experimental data and the rheology contours and mathematical descriptions of boundary lines for meeting the desired rheology are set forth in Example 19 hereinafter. The data were processed using four basic inputs: CMC concentration, glycerin concentration, phosphate buffer concentration and Fo values. The variation of Fo for several representative implant products is shown in FIG. 5. In performing these complex calculations described below and illustrated in several figures, the Fo has been set at the end points of about 22 and 33 using a 121°C sterilization cycle; but other temperatures and times can be used to achieve the same Fo values; and the effect of all other chemical variables can be determined to map the chemical variables to the targeted proper rheological property or properties for a given tissue implant site. It is generally understood that sterilizing material requires that a specific Fo be reached to ensure $10^{-6}$ sterility claims for a product. The use of different combinations of sterilization time and temperature were studied in a Getinge Ab, Sweden autoclave to optimizing the sterilization process. Materials were autoclaved at 121°C for run cycles of 3 mins., 6 mins., 12 mins., and 30 mins. Sterilization programs had sterilization efficacy (Fo) equal to 22, 25, 28 and 33 respectively and the $10^{-6}$ sterility was achieved. Materials were autoclaved at 124°C for run cycles of 4 mins., 7.5 mins., and 11 mins. Sterilization programs had sterilization efficacy (Fo) equal to 26, 36, 46 respectively. Materials were autoclaved at 127°C for run cycles of 0.5 min., 1.5 mins., and 3 mins. Sterilization programs had sterilization efficacy (Fo) equal to 42, 49, 57 respectively.

Variations on rheological parameters used in the method of manufacture can also be incorporated into the analytical methods used to achieve the desired implant rheology. For example, tan δ=G"/G' and such interrelationships can permit simplification of the analysis, such as for example, given knowledge of two of the three parameters to determine the impact of the third variable on rheological parameters. As mentioned hereinbefore, these may be a subset of rheological parameters of particular interest to the selected tissue implant site which thus may not require achieving all the above-mentioned rheological parameter values. In addition, one or more of the rheological parameters may be substantially insensitive to variations in one or more of the manufacturing variables (such as, for example, content of polysaccharide gel, buffer concentration, autoclave Fo value and lubricant content). This would then allow preparing a product mapping to the particular one or more rheological properties for the tissue.

Figure 6:
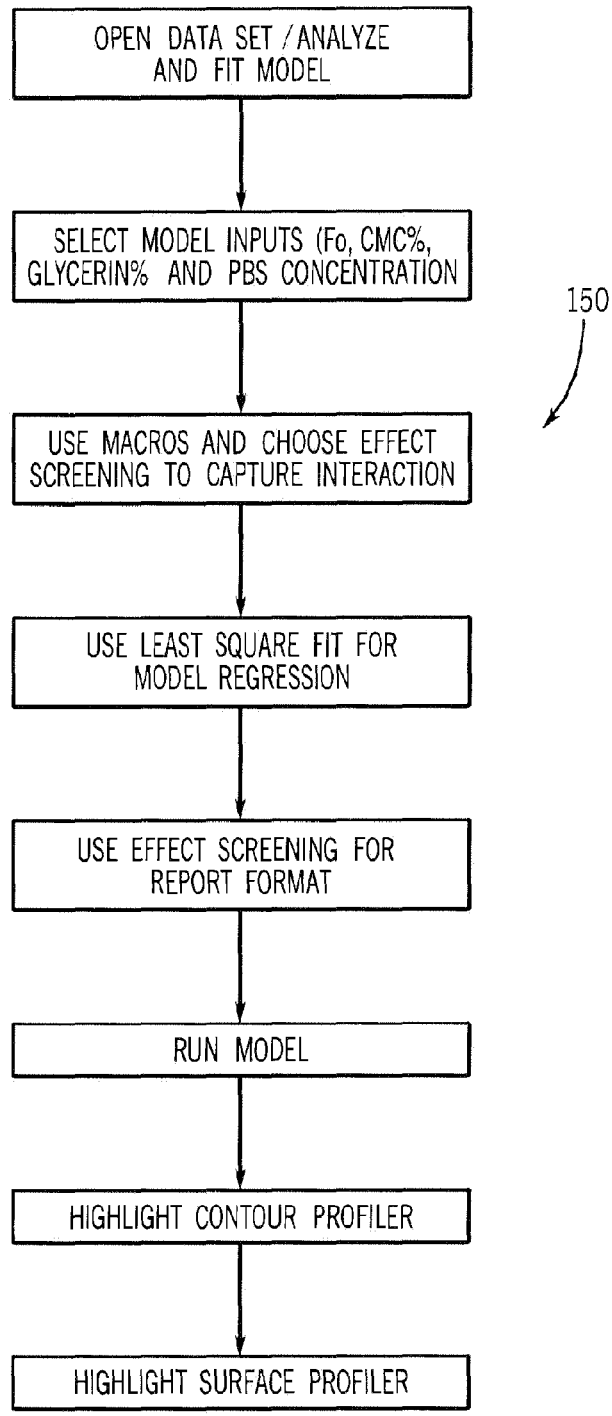
FIG. 6 illustrates a flow chart of an analytical statistical method to analyze chemical variables to map to a target tissue rheology.

In a next step 150 in FIG. 6, an analytical method is used to identify the precise chemical variables needed to map to the desired rheological phase zone to achieve the rheologically matched implant product for the particular tissue site. As stated hereinbefore, in a preferred embodiment the sterilization was carried to a particular range of Fo to achieve a commercially acceptable $10^{-6}$ sterility state. Further, the Fo value increased linearly with all treatments until the beginning of the cooling phase. The main effect of different sterilization temperatures on the cumulative Fo curves was an increase in the slope of the curves with increasing sterilization temperature (see FIG. 5). It also is possible to use higher sterilization temperatures than usually suggested in pharmacopoeias and thus shorten the process time. This sterilization process preferably corresponds to a Fo value range of about 22 to at least about 33, and these values are also associated with a change in the degree of polymeric chain breakdown, as well as achieving the desired sterility. However, this breakdown of polymeric chain leads to an effect on the rheological parameters; and in the most preferred embodiment the range of 24-33 has been characterized in terms of all the remaining preparation variables to establish proper rheological phase zones or regions of merit within which the implant product has the required rheological values to perform well at the tissue implant site. The methodology can also readily be extended to determine the effect of higher Fo values.

In this step 150, one preferred methodology for data analysis to identify the proper implant chemistry is performed using the set of chemical values associated with each data point to carry out a rigorous modeling procedure. Further details are set forth in Example 20. This embodiment can also be described as a screening model by using four inputs: CMC concentration, glycerin concentration, phosphate buffer concentration and Fo values. For example, CMC was varied between 2.3 wt. % and 2.9 wt. % in 0.1% increments, the glycerin content was set to 1.5 wt. %, the buffer was set to 0 M, 25 mM and 100 mM concentration. The model was then executed using two separate Taguchi array screening models as described in Example 19.

Using JMP7.0 pull down menus, the following path was used in the SAS JMP ver. 2.0 software:
Open Data set\Analyze\fit model\
  Select model inputs by highlighting: Fo, CMC concentration (% CMC),
  Glycerin concentration (% Gly), PBS concentration (XmM).
Use macros and choose and/or effect screening to capture all interactions for inputs
Use linear least squares fitting for model regression
Use effect screening for report format
  Run Model
  Under linear least squares: (graphing options of outputs)
  Highlight prediction profiler to graphically represent input interactions.
  Use pull down menus for setting specification limits-optional
  Optimization is based on specification limits used.
  Desirability is a unit-less parameter based on desirability of how well a condition meets the specification for the input condition. Desirability may be calculated for each condition of the data set. A graphing of desirability allows for graphical display of all conditions which meet specifications.
  Highlight Contour profiler to graphically represent 2D input/response interactions.
  Highlight Surface profiler to graphically represent 3D input/response interactions.

Successive iteration of 2-D graphing base on two variables allows for iterative examination of the self limiting output function. This is an exhaustive excersize and only the limiting condition plot is presented. Under this evaluation the sterilization time was found to be limiting from 12 to 25 min (Fo 22 to 33).

The limiting value of Fo was then incorporated into the development of the prediction model using the prediction formulas from the screening model contours for each output. The screening model was developed based on the following four inputs: CMC concentration (% CMC), glycerin concentration (% gly), phosphate buffer concentration (mM) and autoclave time. The CMC concentration (% CMC) was varied between 2.3% w/v and 2.9% w/v in 0.1% w/v increments. The glycerin concentration (% gly) was held to 0% w/v, 1.0% w/v and 1.5% w/v. The buffer concentration (mM) was varied from 0, 25 mM, 50 mM and 100 mM concentration. This creates a full factorial design of with 420 interactive conditions. The prediction formulas were input into a full factorial design. The rheological outputs were calculated based on screening model prediction formulas. See attachment II. Again, the data were analyzed by use of SAS JMP ver. 7.0 statistical software following the steps of FIG. 6 to generate prediction profiles, three dimension ("3D") surface contour plots (see, for example, FIG. 7B(i)-7B(viii). The prediction model provides statistical strength to the model incorporating more data points into the model description. Further details are set forth in Example 19.

Figures 7A, 7B:
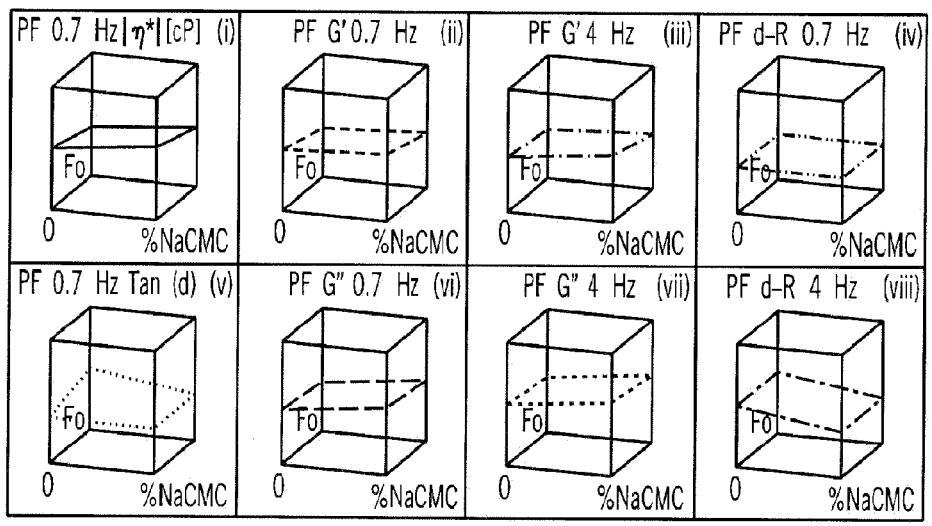
FIG. 7A shows a list of chemical variables and a tabular key for a first range of rheological variables.
FIG. 7B(i) shows Fo versus percent CMC and viscosity.
Figure 7C:
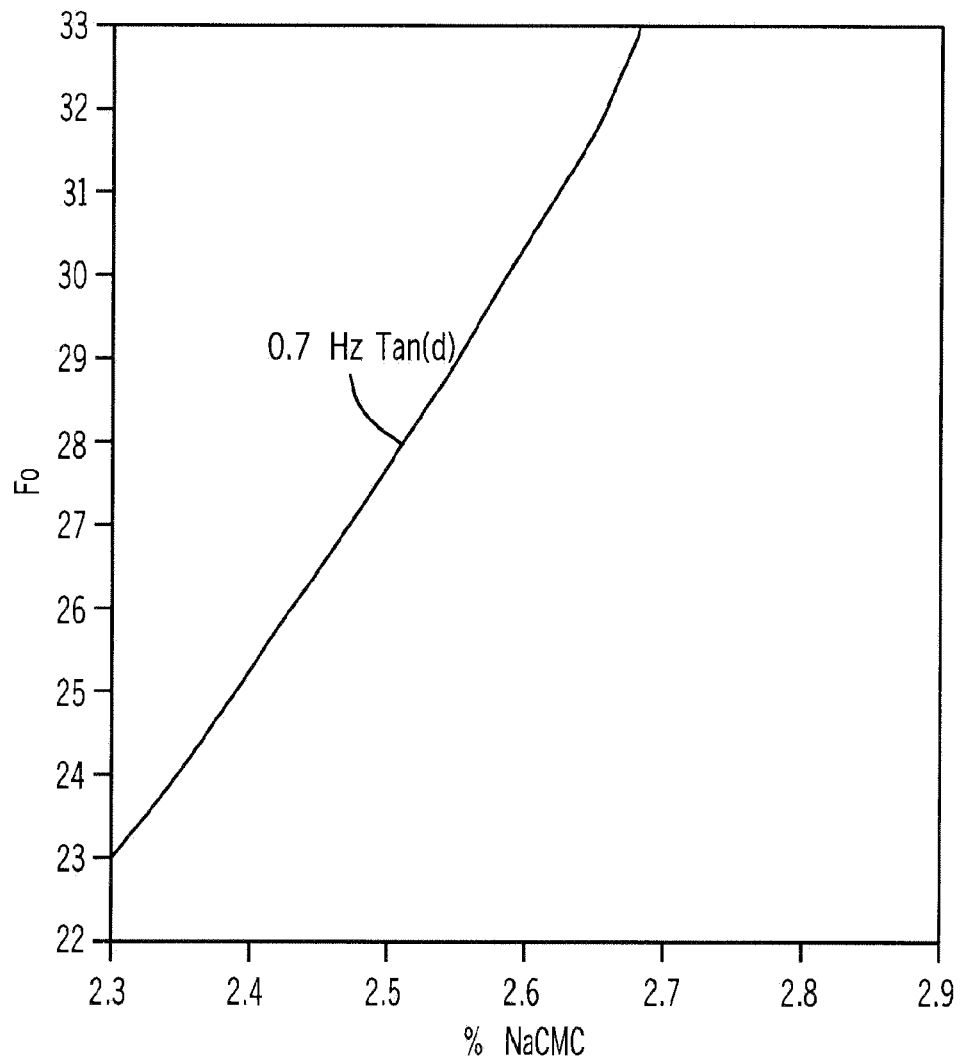
FIG. 7C shows the 2D plot of a region of rheological merit (white) versus a region not meeting the parameters (dark)
Figure 9A:
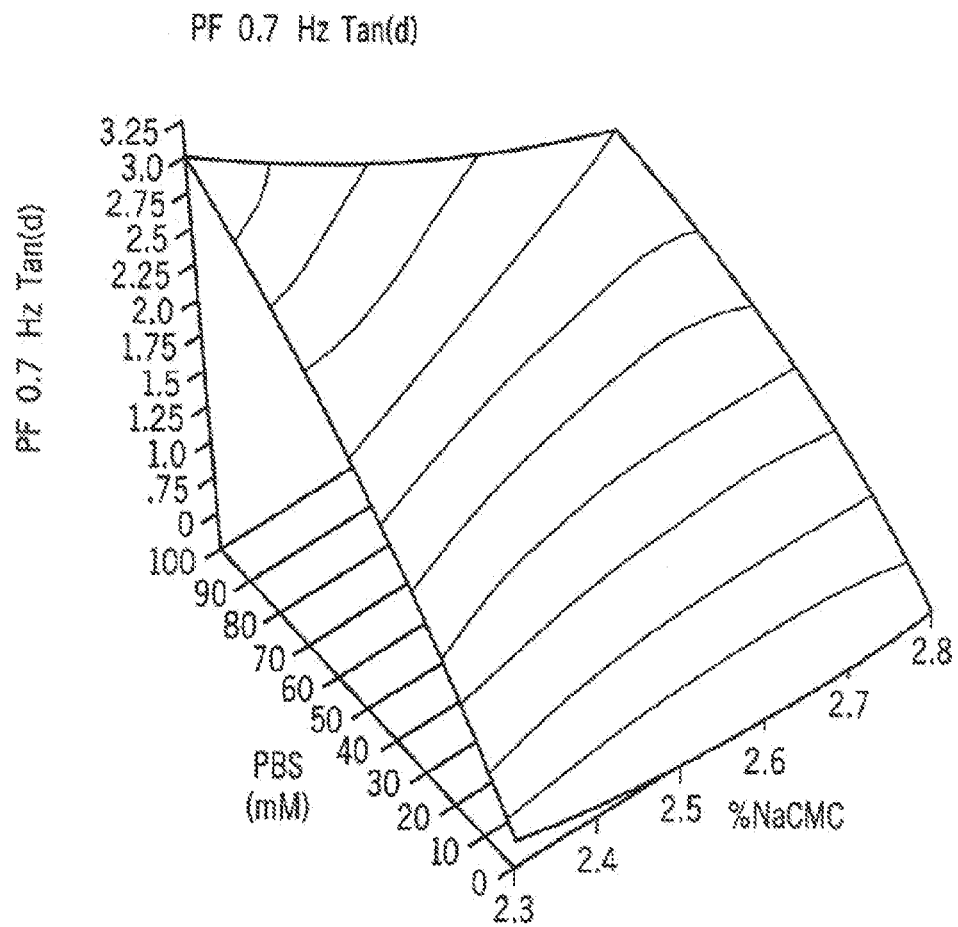
FIG. 9A(i) is a 3D contour of CMC percent versus PBS (mM) versus tan $\delta$.
Figure 9A:
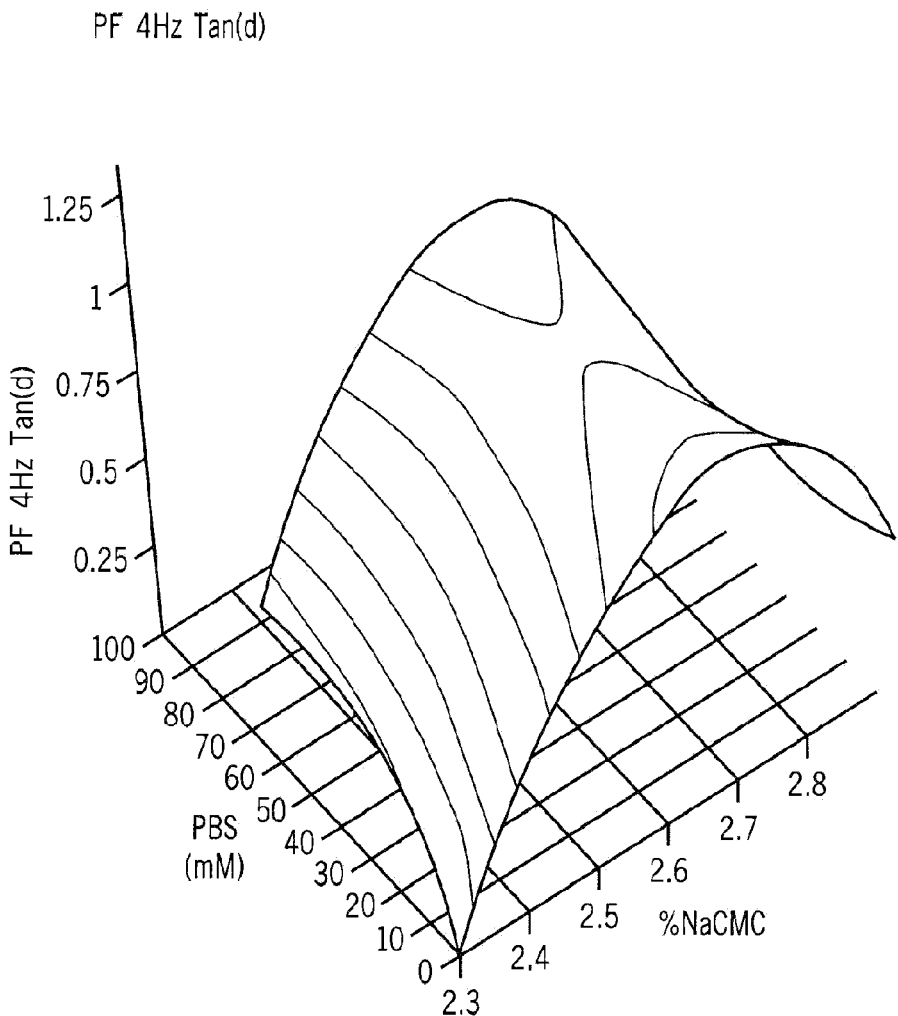

Again noted hereinbefore, the analysis by use of SAS JMP ver. 7.0 statistical software provides useful three dimensional ("3D") contour plots (see, for example, FIGS. 7B(i)-7B(viii)) FIG. 7C and also FIGS. 9A(i)-9A(ix). Other suitable conventional statistical analysis software can also be used in this one type of methodology to analyze the base chemical parameter data from the test product samples. This approach can generate data fits allowing formation of 3D surfaces and line fits to identify phase regions of merit based on the implant/tissue constraints to determine the three dimension plot of rheological behavior and selection of a minimum and maximum range of those rheological parameters to meet the preset desired rheological conditions and properties. Example 19 hereinafter also provides details of equations defining the boundary lines and contours.

Regarding criteria for rheological variables for the implant product, Example 19 is for an implant application in lip tissue, wherein (1) the G' and G" behavior should preferably be within a range of about 0 to 300 pas to map to the desired property since the interstitial extracellular matrix of the lip tissue comprises a hyaluronic acid polysaccharide for which the rheology range can be identified; and their plots should crossover at a physiologically relevant frequency of about 0.5 to 4 Hz which is consistent with the lip tissue functionality, and (2) the viscosity should be about 0 to 300,000 cps for the same physiologically relevant stress ranges. The tan δ should be greater than 1 for low stress conditions indicating an inherent viscous nature to the material with decreasing tan δ as the stress increases demonstrating elastic behavior of lip:tissue nodal properties. Phase or deflection angle should be about 5 to 110 over the stress range of 0.1 Hz to 4 Hz. The SAS analytical method produced families of rheological variable plots that met the following rheological evaluation parameters and can be summarized in Table 7.

TABLE 7

| Rheological parameter | | |
|---|---|---|
| Viscosity (5τ, 30 degree C parallel plate) 0.7 Hz | 7200 cps to 53000 cps | Data based on the specification limits of a present conventional implant product. This is supported in the published references for several hyaluronic acid compositions. |
| Tan δ 0.7 Hz | >1 | Data based on the specification limits of the conventional product and the desired rheology at low stresses. Material for dermal application should show minimal elastic behavior at low stress to act more like the surrounding tissue and the Newtonian fluid (water) microenvironment. This is supported in the published references for several hyluronic acid compositions as they demonstrate viscous to elastic behavior under increasing stress and cross-over at some stress point. |
| G" and G" 0.7 Hz | <300 cps | Data from Fung reference with various hyaluronic acid compositions. Hyaluronic acid is a primary constituent of dermal extra cellular matrix. |
| G' and G" 4.0 Hz | <100 cps | Data from Fung reference with various hyaluronic acid compositions. Hyaluronic acid is a primary constituent of dermal extra cellular matrix and this seems to be applicable. |
| Tan δ 11.7 Hz | <1 | Data set based on the specification limits of the conventional product and the desired rheology at higher stresses. It would be best if material demonstrated some elastic character when subjected to higher stress to limit movement or deformation of form. |
| δ-R 0.7 Hz & 4 Hz | <60 and <110 | Data supported in published references for phase angle evaluation of lips. The limits were subjective and taken from the graphs as presented in the literature. Evaluation at two points 0.7 Hz & 4 Hz covers the physiologically relevant range of stresses. |

In a next step 160, lines having a mathematical behavior are part of a series of identified loci for each single one of the rheological variables for which the conditions have been met. These are shown in FIG. 7C as the line separating the acceptable white zone from the adjacent dark zone. As stated hereinbefore Example 19 provides further details of the analysis and the mathematical descriptions. Also in a step 170, a phase zone of merit can be identified which is the white zone in FIG. 7C where the universe of rheological parameters limits were all met. This establishes the target implant product phase zone of merit. In some cases, as noted hereinbefore, it is necessary to use only one of the rheological parameters to define a "region of merit" in order to identify the chemical characteristics which meet the implant tissue requirements. Numerous examples are set forth hereinafter delineating these rheological loci of proper performance or merit and also target rheological phase zones of merit. The examples are in particular directed to lip tissue implantation; but in view of knowledge of other tissue rheology, the methodology described herein can be used for any tissue site with known rheological parameters. The statistical method is executed by the above-referenced SAS off the shelf software formalisms, including for example Monte Carlo calculations and which are part of the analysis show in the statistical analysis flow chart of FIG. 3.

Figure 8:
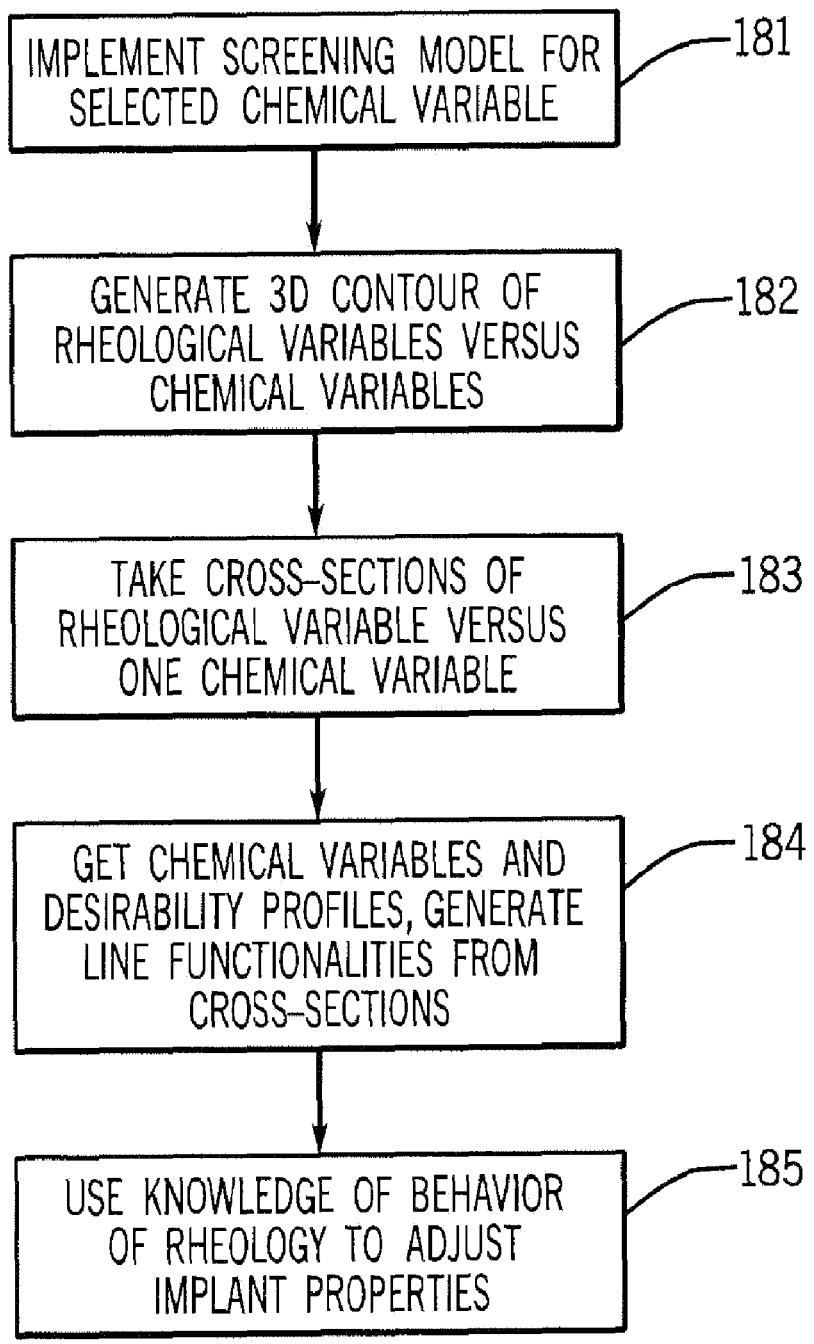
FIG. 8 illustrates a flow chart of the steps in creating prediction profiles.

In another embodiment, an enhancement based on the steps 160 and 170 can be implemented to establish the applicability and functionality of the rheological variables relative to the chemical variables. This can be accomplished by a step 180 of generating a predictive profiler mathematical model using the one or more inputs of the rheological parameters in a screening model least squares regression to form plots of chemical variables versus rheological outputs of choice. FIG. 8 shows the steps of the predictive profiler in step 181 of implementing the screening model of step 150 to select one of the rheological parameters as a function of two chemical variables. From this analysis the SAS software can generate in step 182 the 3D contours of the rheological parameters versus the two chemical variables (see, for example, FIGS. 9A(i)-9A(ix)). In a next step 183 a planar cross-section is taken at a set value of one of the chemical variables (see FIG. 9A(ii)). In a next step 184, the planar intersection with the contour of the rheological function establishes a line for the selected variables (see FIG. 9B for a matrix of these various lines in the rheology contours for the given parameters). In a step 185 knowledge of the sensitivity of the rheology parameters to the chemical variables allows control of the chemistry. (See the various plots in FIG. 9B). These prediction profiles then demonstrate how the change in one chemical variable input has a fairly modest impact on certain rheological variables as the other variables are held constant, while other chemical variables have very dramatic impact on rheological response as the other variables are held constant. For example, as shown in FIG. 9B, the PBS chemical variable causes quite dramatic changes in selected rheological outputs. Their variability (or lack thereof) can be used to either simplify manufacture of a desired end product or further effect the ultimate value of a given rheological variable in combination with knowledge of the location within a rheological phase zone or region suitable for a selected tissue implant site. As described hereinbefore, further details of the mathematical equations which are created by the SAS software to describe contours and lines are characterized in Example 19 and are executed by graphing scripts of the software.

In another procedure in step 190, a "desirability" measure or region can be determined by analyzing the input data and rheological parameters by limiting the model to only those conditions which meet the required output ranges. Desirability is an index to evaluate if the testing condition meets the specifications and to what degree. Those values that are less than 0 fail to meet one or all of the criteria for acceptable material. Thus they are not included in the 3D plots. All other combinations of variables that have positive desirability meet the specification goals to some relative degree. The threshold condition of desirability was limited to 0.5 as the predictive optimal obtainable in this case (as no one condition optimizes all outputs). Model strength can be further enhanced by increasing the amount of experimental data. This can be done through the brute force method of more iterative runs of all possible conditions or in this case the statistical SAS JMP ver. 7.0 included a Monte Carlo simulation to infinitely limit the degree of acceptable material, therefore defining the surface of the acceptable region. A threshold limit for desirability was established at 0.15 to allow a degree of confidence in the model simulation because normal variance was included in the Monte Carlo simulation.

The methods and products described hereinbefore can be implemented by a supplier establishing a database of rheological data for tissue of anyone of a plurality of particular types of patients; and understanding how to execute the methods described herein, the supplier can then map out implant products and their associated rheological properties to determine which products meet the compatibility requirements for the particular tissue. Thus, the above-described regions of merit and also desirability plots can help define the proper product.

Examples of such a "desirability" analysis are provided hereinafter in FIGS. 31A-31F.

The following non-limiting examples illustrate various aspects of the invention.

Example 1

Preparation of 2.3% Sodium CMC Gel in Sterile Water

Figure 10:
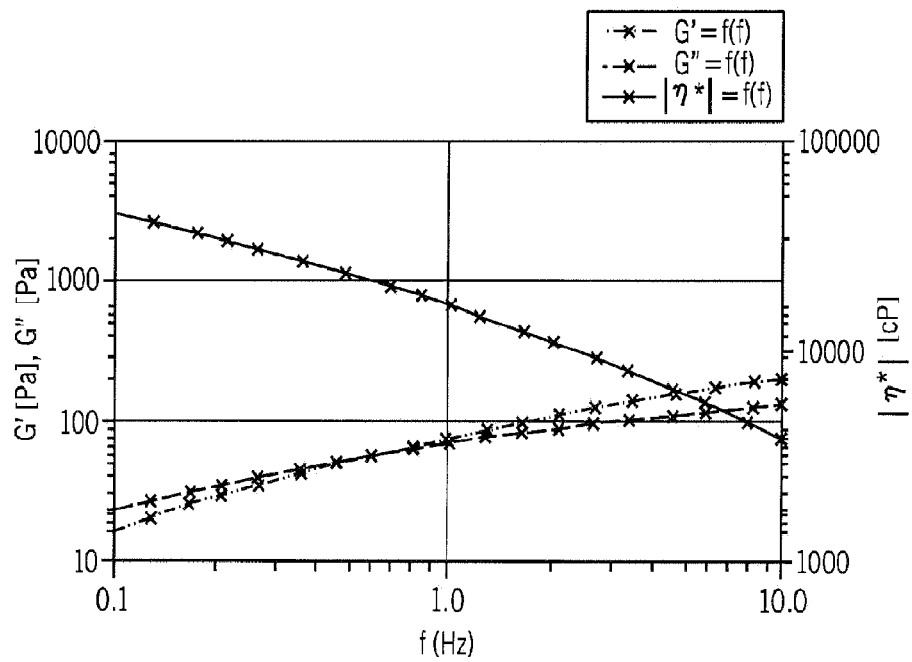
FIG. 10 illustrates a plot of elastic viscous modulus and complex viscosity as a function of frequency for the composition of Example 1.

Sodium carboxymethylcellulose was prepared in sterile water for injection and adjusted to a pH of from about 7.1 to about 8.0 using potassium hydroxide. The dispersion was mixed in an orbital Ross mixer @1725 RPM for 5 minutes followed by mixing in an orbital Ross mixer @1725 RPM for 40 minutes. while holding a vacuum @26 mm Hg or more. The composition was then steam sterilization at 121° C. for times ranging from 3 minutes to 30 minutes. In addition, one sample was sterilized for time intervals between 3 minutes and 30 minutes @121° C. Results are shown in FIG. 10 where G' represents the elastic modulus, G" represents the viscous modulus and the η complex viscosity. The profile shows that G' and G" intersect at 0.495 Hz (3.2 Rad/sec). Above this frequency, the composition exhibits non-Newtonian solution characteristics (tan δ<1.0).

Example 2

Preparation of 2.4% Sodium CMC Gel in Sterile Water

Figure 11:
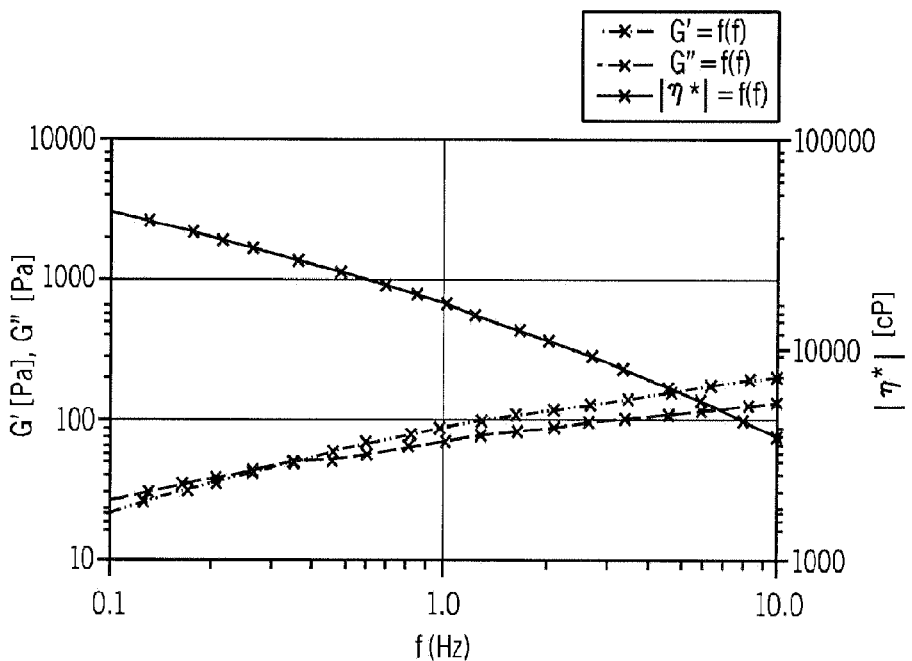
FIG. 11 illustrates a plot of elastic and viscous modulus and complex viscosity as a function of frequency for the composition of Example 2.

Sodium carboxymethylcellulose was prepared in sterile water for injection and adjusted to a pH of from about 7.1 to about 8.0 using potassium hydroxide. The dispersion was mixed in an orbital Ross mixer @1725 RPM for 5 minutes followed by mixing in an orbital Ross mixer @1725 RPM for 40 minutes while holding a vacuum @26 mm Hg or more. The composition was then steam sterilization at 121° C. for times ranging from 3 minutes to 30 minutes. In addition, one sample was sterilized for time intervals between 3 minutes and 30 minutes @121° C. Results are shown in FIG. 11 where G' represents the elastic modulus, G" represents the viscous modulus and the complex viscosity. The profile shows that G' and G" intersect at 0.0299 Hz (1.8 Rad/sec) (lower frequency than that shown in FIG. 1). Above this frequency, the composition exhibits non-Newtonian solution characteristics (tan δ<1.0).

Example 3

Preparation of 2.5% Sodium CMC Gel in Sterile Water

Figure 12:
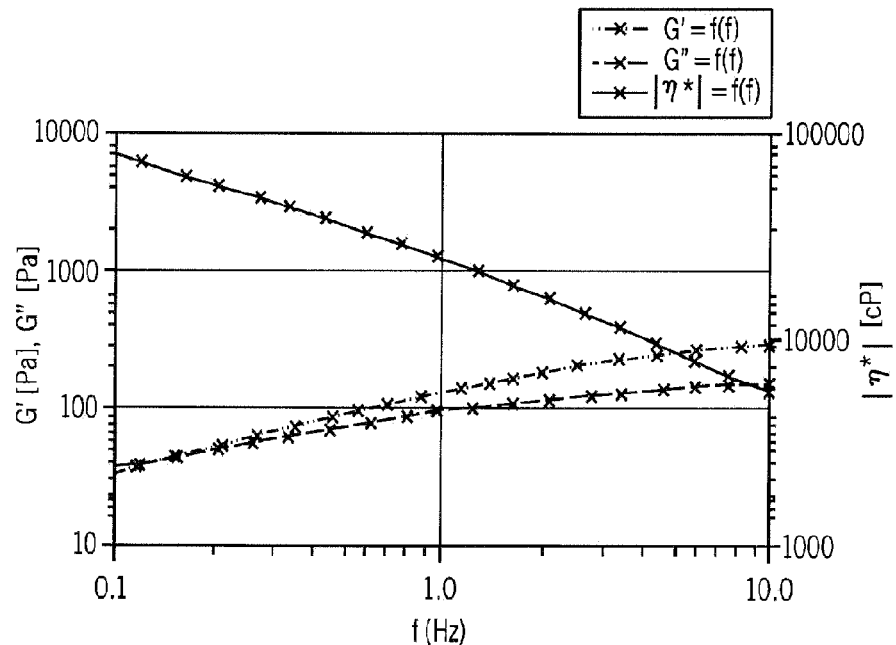
FIG. 12 illustrates a plot of elastic and viscous modulus and complex viscosity as a function of frequency for the composition of Example 3.

Sodium carboxymethylcellulose was prepared in sterile water for injection and adjusted to a pH of from about 7.1 to about 8.0 using potassium hydroxide. The dispersion was mixed in an orbital Ross mixer @1725 RPM for 5 minutes followed by mixing in an orbital Ross mixer @1725 RPM for 40 minutes while holding a vacuum @26 mm Hg or more. The composition was then steam sterilization at 121° C. for times ranging from 12 minutes to 30 minutes. In addition, one sample was sterilized for time intervals between 3 minutes and 12 minutes @121° C. Results are shown in FIG. 12 where G' represents the elastic modulus, G" represents the viscous modulus and η the complex viscosity. The profile shows that G' and G" intersect at 0.157 Hz (1 rad/sec) frequency than shown in FIGS. 10 and 11. Above this frequency, the composition exhibits non-Newtonian solution characteristics (tan δ<1.0).

Example 4

Preparation of 2.6% Sodium CMC Gel in Sterile Water

Figure 13:
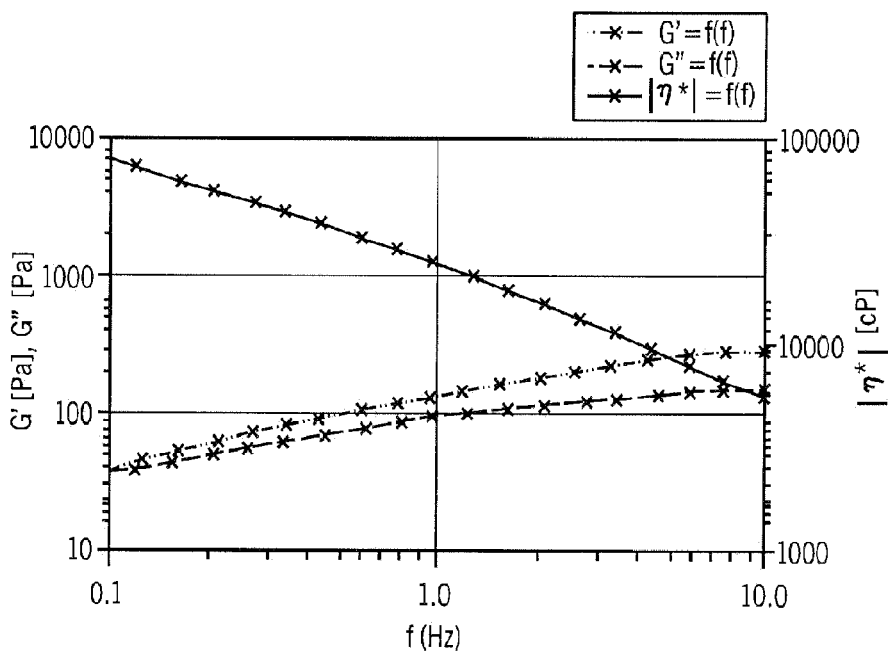
FIG. 13 illustrates a plot of elastic and viscous modulus and complex viscosity as a function of frequency for the composition of Example 4.

Sodium carboxymethylcellulose was prepared in sterile water for injection and adjusted to a pH of from about 7.1 to about 8.0 using potassium hydroxide. The dispersion was mixed in an orbital Ross mixer @1725 RPM for 5 minutes followed by mixing in an orbital Ross mixer @1725 RPM for 40 minutes while holding a vacuum @26 mm Hg or more. The composition was then steam sterilization at 121° C. for times ranging from 12 minutes to 30 minutes. In addition, one sample was sterilized for time intervals between 12 minutes and 30 minutes @121° C. Results are shown in FIG. 13 where G' represents the elastic modulus, G" represents the viscous modulus and η the complex viscosity. The profile shows the G' and G" intersect at 0.164 Hz (1.03 rad/sec). Above this frequency, the composition exhibits non-Newtonian solution characteristics (tan δ<1.0).

Example 5

Preparation of 2.3% Sodium CMC Gel in Potassium Phosphate Buffer

Figure 14:
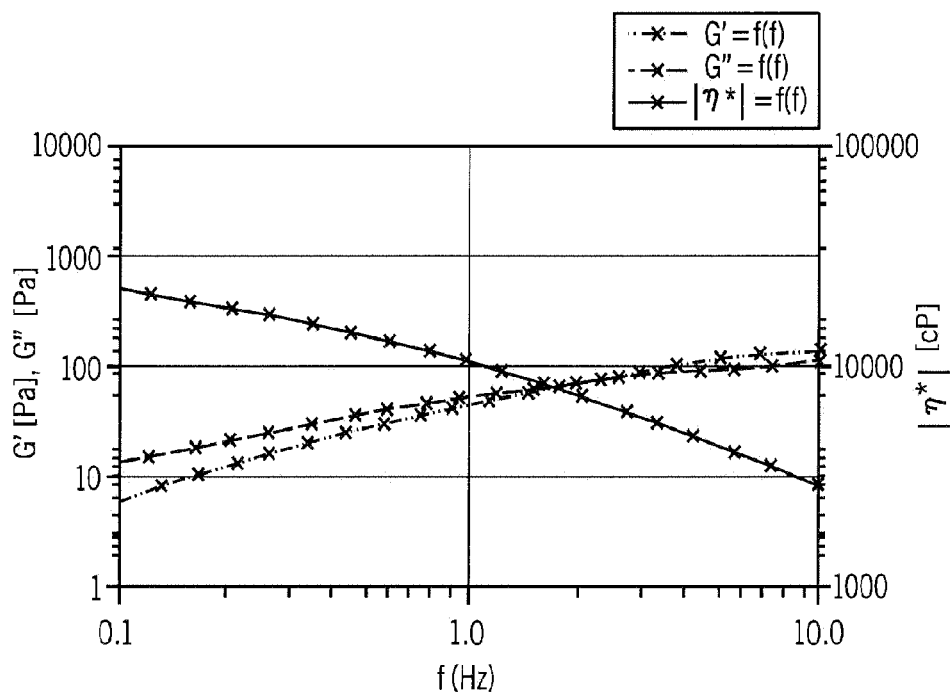
FIG. 14 illustrates a plot of elastic and viscous modulus and complex viscosity as a function of frequency for the composition of Example 5.

Sodium carboxymethylcellulose was prepared in sterile 25 mM to 100 mM potassium phosphate buffer pH and adjusted to a pH of from about 7.2 to about 8.0 using potassium hydroxide. The dispersion was mixed in an orbital Ross mixer @1725 RPM for 5 minutes followed by mixing in an orbital Ross mixer @1725 RPM for 40 minutes while holding a vacuum @26 mm Hg or more. The composition was then steam sterilization at 121° C. for times ranging from 3 minutes to 12 minutes. In addition, one sample was sterilized for time intervals between 3 minutes and 12 minutes @121° C. Results are shown in FIG. 14 where G' represents the elastic modulus, G" represents the viscous modulus and η the complex viscosity. The profile shows that G' and G" intersect at 2.401 Hz (15 rad/sec) (similar to that shown in FIG. 13). Above this frequency, the composition exhibits non-Newtonian solution characteristics (tan δ<1.0).

Example 6

Preparation of 2.4% Sodium CMC Gel in Potassium Phosphate Buffer

Figure 15:
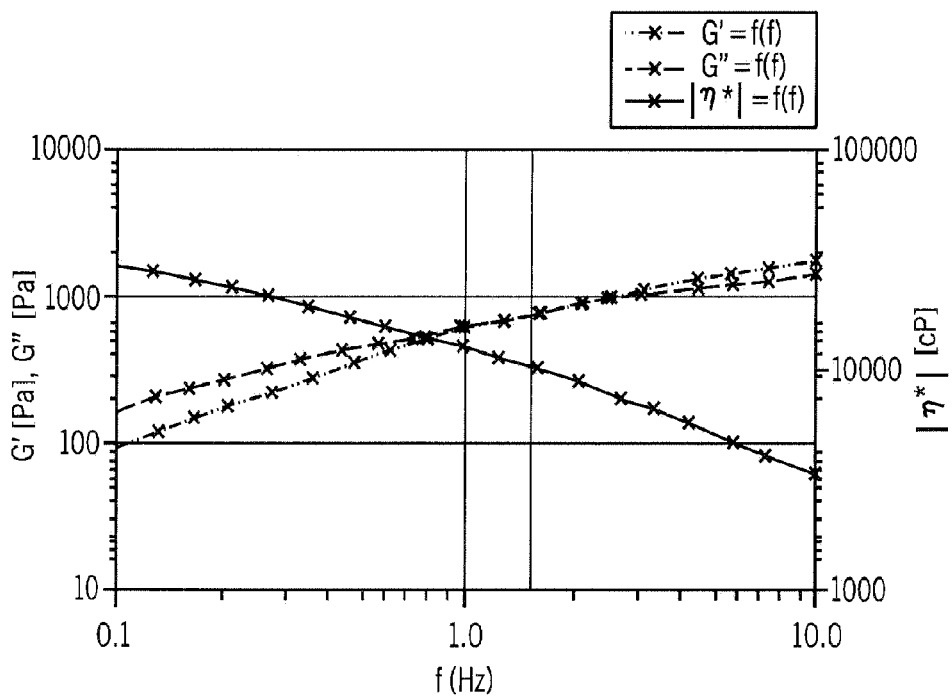
FIG. 15 illustrates a plot of elastic and viscous modulus and complex viscosity as a function of frequency for the composition of Example 6.

Sodium carboxymethylcellulose was prepared in sterile 25 mM to 100 mM potassium phosphate buffer pH and adjusted to a pH of from about 7.2 to about 8.0 using potassium hydroxide. The dispersion was mixed in an orbital Ross mixer @1725 RPM for 5 minutes followed by mixing in an orbital Ross mixer @1725 RPM for 40 minutes while holding a vacuum @26 mm Hg or more. The composition was then steam sterilization at 121° C. for times ranging from 3 minutes to 12 minutes. In addition, one sample was sterilized for time intervals between 3 minutes and 12 minutes @121° C. Results are shown in FIG. 15 where G' represents the elastic modulus, G" represents the viscous modulus and η the complex viscosity. The profile shows that G' and G" intersect at 1056 Hz. (9.8 rad/sec). Above this frequency, the composition exhibits non-Newtonian solution characteristics (tan δ<1.0).

Example 7

Preparation of 2.5% Sodium CMC Gel in Potassium Phosphate Buffer

Figure 16:
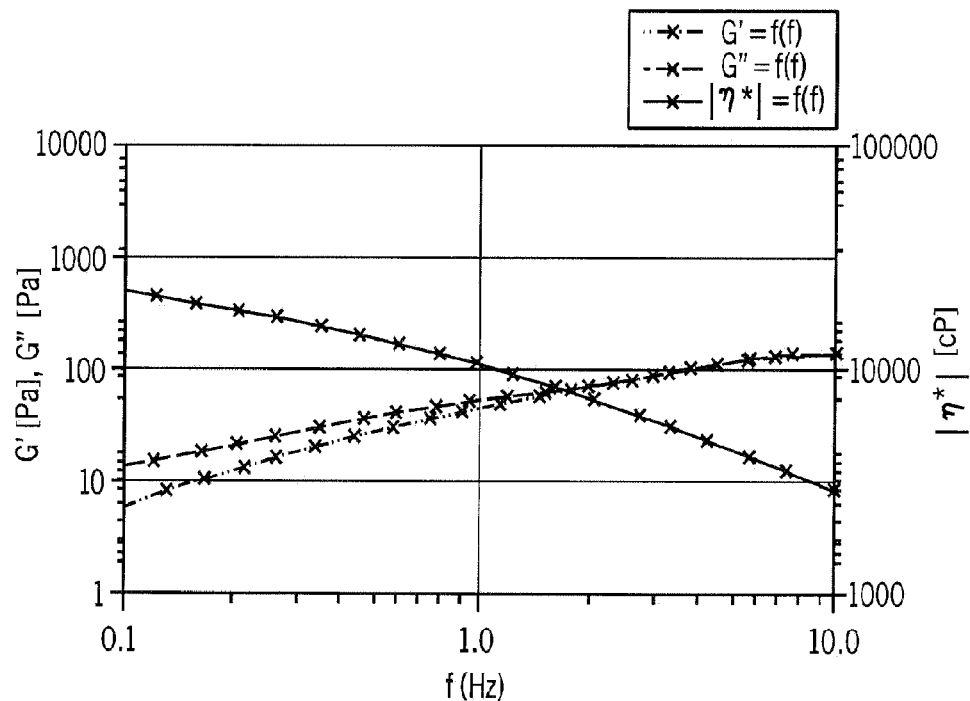
FIG. 16 illustrates a plot of elastic and viscous modulus and complex viscosity as a function of frequency for the composition of Example 7.

Sodium carboxymethylcellulose was prepared in sterile 25 mM to 100 mM potassium phosphate buffer pH and adjusted to a pH of from about 7.2 to about 8.0 using potassium hydroxide. The dispersion was mixed in an orbital Ross mixer @1725 RPM for 5 minutes followed by mixing in an orbital Ross mixer @1725 RPM for 40 minutes while holding a vacuum @26 mm Hg or more. The composition was then steam sterilization at 121° C. for times ranging from 3 minutes to 12 minutes. In addition, one sample was sterilized for time intervals between 3 minutes and 12 minutes @121° C. Results are shown in FIG. 16 where G' represents the elastic modulus, G" represents the viscous modulus and η the complex viscosity. The profile shows that G' and G" intersect at 4.54 Hz (28.5 rad/sec). Above this frequency, the composition exhibits non-Newtonian solution characteristics (tan δ<1.0).

Example 8

Preparation of 2.6% Sodium CMC Gel in Potassium Phosphate Buffer

Figure 17:
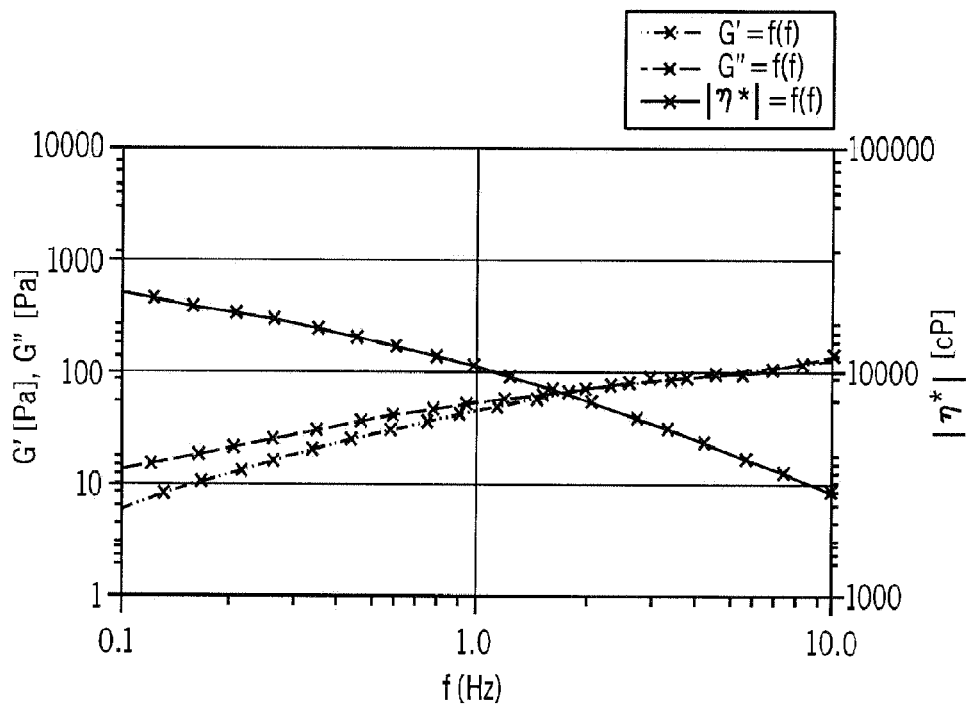
FIG. 17 illustrates a plot of elastic and viscous modulus and complex viscosity as a function of frequency for the composition of Example 8.

Sodium carboxymethylcellulose was prepared in sterile 25 mM to 100 mM potassium phosphate buffer pH and adjusted to a pH of from about 7.2 to about 8.0 using potassium hydroxide. The dispersion was mixed in an orbital Ross mixer @1725 RPM for 5 minutes followed by mixing in an orbital Ross mixer @1725 RPM for 40 minutes while holding a vacuum @26 mm Hg or more. The composition was then steam sterilization at 121° C. for times ranging from 3 minutes to 12 minutes. In addition, one sample was sterilized for time intervals between 3 minutes and 12 minutes @121° C. Results are shown in FIG. 17 where G' represents the elastic modulus, G" represents the viscous modulus and η the complex viscosity. The profile shows that G' and G" intersect at 3.61 (22.7 rad/sec) Hz. Above this frequency, the composition exhibits non-Newtonian solution characteristics (tan δ<1.0).

Example 9

Preparation of 2.7% Sodium CMC Gel in Potassium Phosphate Buffer

Figure 18:
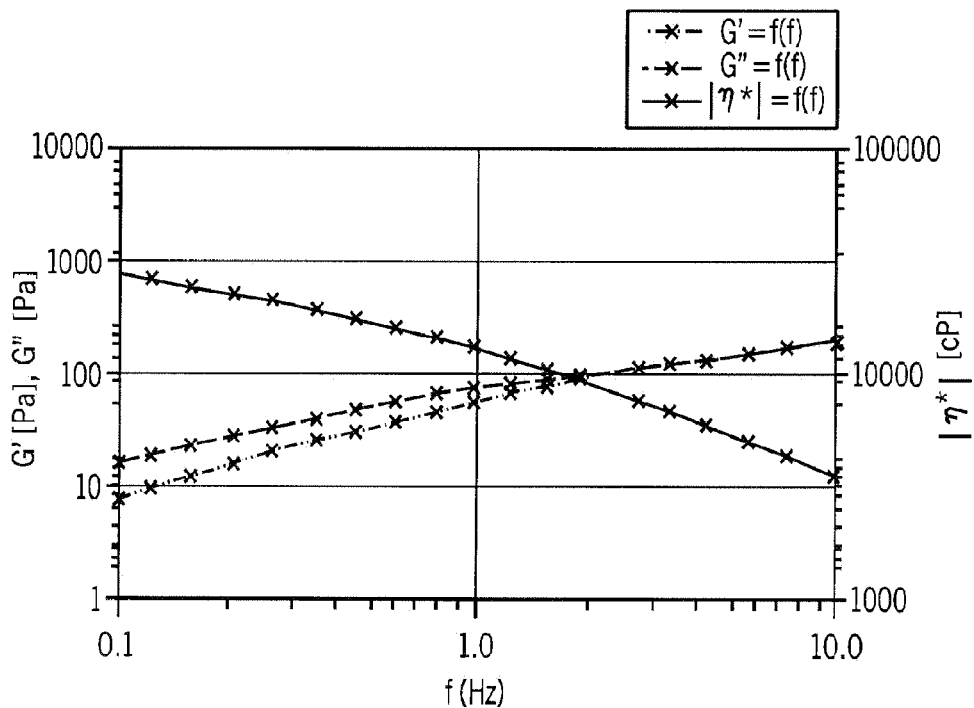
FIG. 18 illustrates a plot of elastic and viscous modulus and complex viscosity as a function of frequency for the composition of Example 9.

Sodium carboxymethylcellulose was prepared in sterile 25 mM to 100 mM potassium phosphate buffer pH and adjusted to a pH of from about 7.2 to about 8.0 using potassium hydroxide. The dispersion was mixed in an orbital Ross mixer @1725 RPM for 5 minutes followed by mixing in an orbital Ross mixer @1725 RPM for 40 minutes while holding a vacuum @26 mm Hg or more. The composition was then steam sterilization at 121° C. for times ranging from 3 to 12 minutes. In addition, one sample was sterilized for time intervals between 3 minutes and 12 minutes @121° C. Results are shown in FIG. 18 where G' represents the elastic modulus, G" represents the viscous modulus and η the complex viscosity. The profile shows that G' and G" intersect at 3.49 Hz (21.9 rad/sec). Above this frequency, the composition exhibits non-Newtonian solution characteristics (tan δ<1.0). At this sodium CMC concentration (2.7%) the intersect shifts to a lower frequency than that shown in FIG. 16 (2.5% CMC). The composition still exhibits Newtonian fluid characteristics.

Example 10

Preparation of 2.8% Sodium CMC Gel in Potassium Phosphate Buffer

Figure 19:
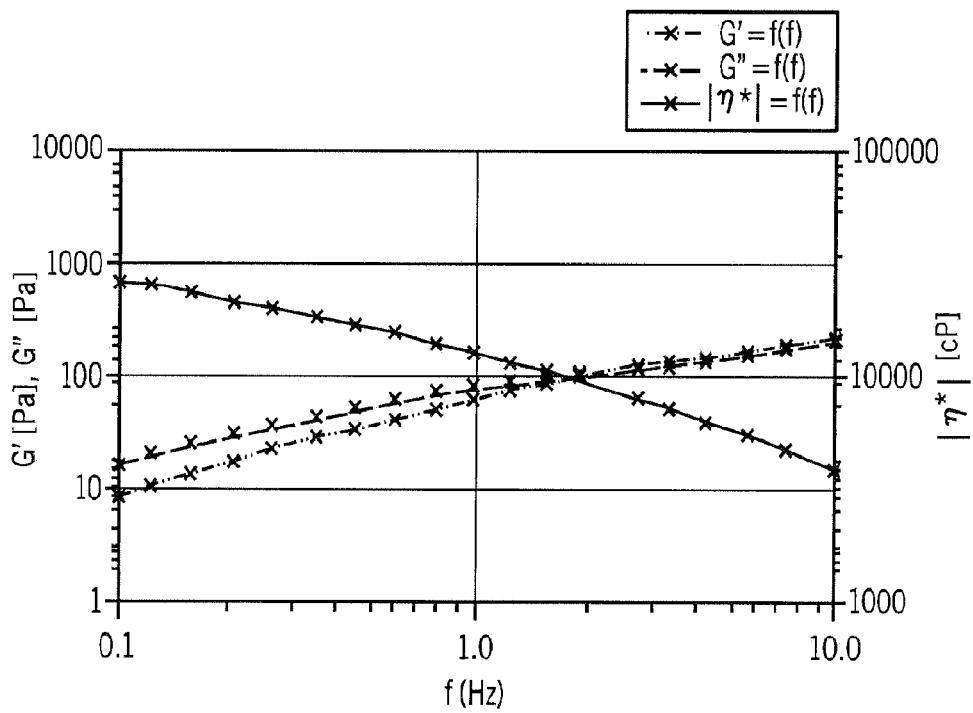
FIG. 19 illustrates a plot of elastic and viscous modulus and complex viscosity as a function of frequency for the composition of Example 10.

Sodium carboxymethylcellulose was prepared in sterile 25 mM to 100 mM potassium phosphate buffer pH and adjusted to a pH of from about 7.2 to about 8.0 using potassium hydroxide. The dispersion was mixed in an orbital Ross mixer @1725 RPM for 5 minutes followed by mixing in an orbital Ross mixer @1725 RPM for 40 minutes while holding a vacuum @26 mm Hg or more. The composition was then steam sterilization at 121° C. for times ranging from 3 minutes to 12 minutes. In addition, one sample was sterilized for time intervals between 3 minutes and 12 minutes @121° C. Results are shown in FIG. 19 where G' represents the elastic modulus, G" represents the viscous modulus and η the complex viscosity. The profile shows that G' and G" intersect at 4.88 Hz (30.7 rad/sec). Above this frequency, the composition exhibits non-Newtonian solution characteristics (tan δ<1.0). Since the intersect occurs at the top end frequency, this composition exhibits Newtonian characteristics at nearly all frequencies.

Example 11

Preparation of 2.6% Sodium CMC Gel in Potassium Phosphate Buffer and Glycerin

Figure 20:
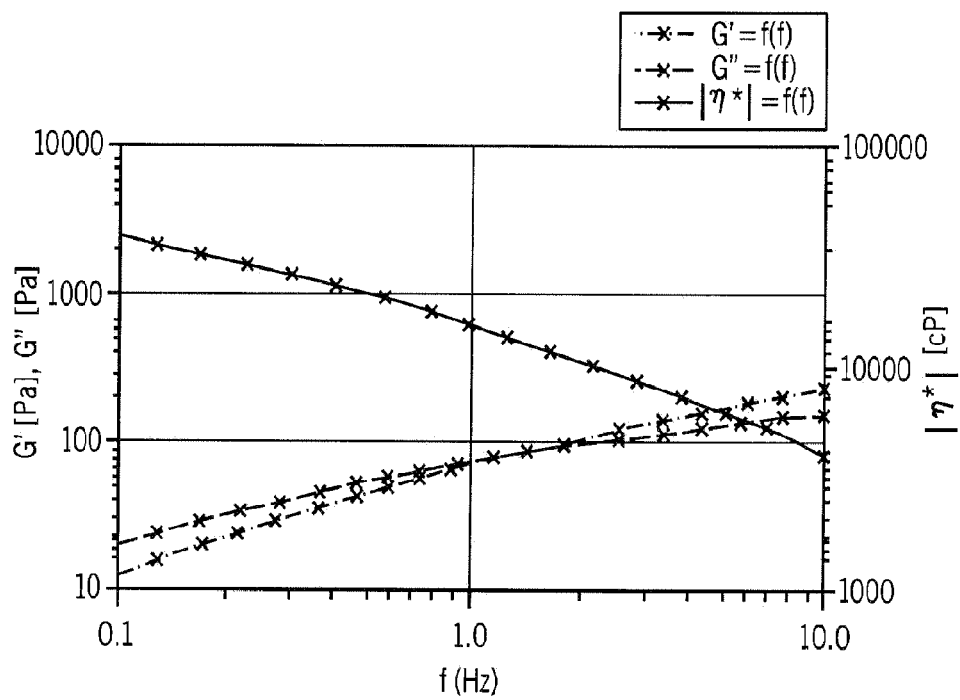
FIG. 20 illustrates a plot of elastic and viscous modulus and complex viscosity as a function of frequency for the composition of Example 11.

Sodium carboxymethylcellulose was prepared in sterile 25 mM to 100 mM potassium phosphate buffer adjusted to a pH of from about 7.2 to about 8.0 using potassium hydroxide and containing up to 1% glycerin. The dispersion was mixed in an orbital Ross mixer @1725 RPM for 5 minutes followed by mixing in an orbital Ross mixer @1725 RPM for 40 minutes while holding a vacuum @26 mm Hg or more. The composition was then steam sterilization at 121° C. for times ranging from 3 minutes to 12 minutes. In addition, one sample was sterilized for time intervals between 3 minutes and 12 minutes @121° C. Results are shown in FIG. 20 where G' represents the elastic modulus, G" represents the viscous modulus and η the complex viscosity. The profile shows that G' and G" intersect at 1.254 Hz (7.8 rad/sec). Above this frequency, the composition exhibits non-Newtonian solution characteristics (tan δ<1.0). The addition of glycerin to sodium CMC gel in potassium phosphate significantly affects the rheology of the composition, changing it from a fundamentally Newtonian fluid to a non-Newtonian fluid above a frequency of about 1.0.

Example 12

Preparation of 2.7% Sodium CMC Gel in Potassium Phosphate Buffer and Glycerin

Figure 21:
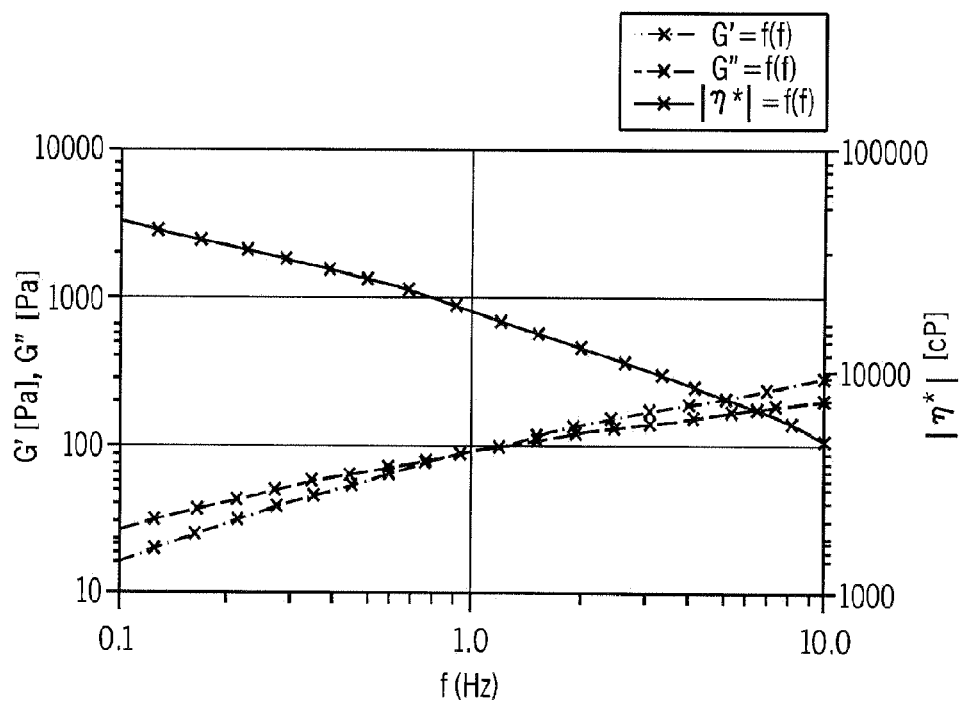
FIG. 21 illustrates a plot of elastic and viscous modulus and complex viscosity as a function of frequency for the composition of Example 12.

Sodium carboxymethylcellulose was prepared in sterile 25 mM to 100 mM potassium phosphate buffer adjusted to a pH of from about 7.2 to about 8.0 using potassium hydroxide and containing up to 1% glycerin. The dispersion was mixed in an orbital Ross mixer @1725 RPM for 5 minutes followed by mixing in an orbital Ross mixer @1725 RPM for 40 minutes while holding a vacuum @26 mm Hg or more. The composition was then steam sterilization at 121° C. for times ranging from 3 minutes to 12 minutes. In addition, one sample was sterilized for time intervals between 3 minutes and 12 minutes @121° C. Results are shown in FIG. 21 where G' represents the elastic modulus, G" represents the viscous modulus and η the complex viscosity. The profile shows that G' and G" intersect at 1.158 Hz (7.2 rad/sec). Above this frequency, the composition exhibits non-Newtonian solution characteristics (tan δ<1.0). The addition of glycerin to sodium CMC gel in potassium phosphate significantly affects the rheology of the composition, changing it from a fundamentally Newtonian fluid to a non-Newtonian fluid above a frequency of about 1.0.

Example 13

Preparation of 2.8% Sodium CMC Gel in Potassium Phosphate Buffer and Glycerin

Figure 22:
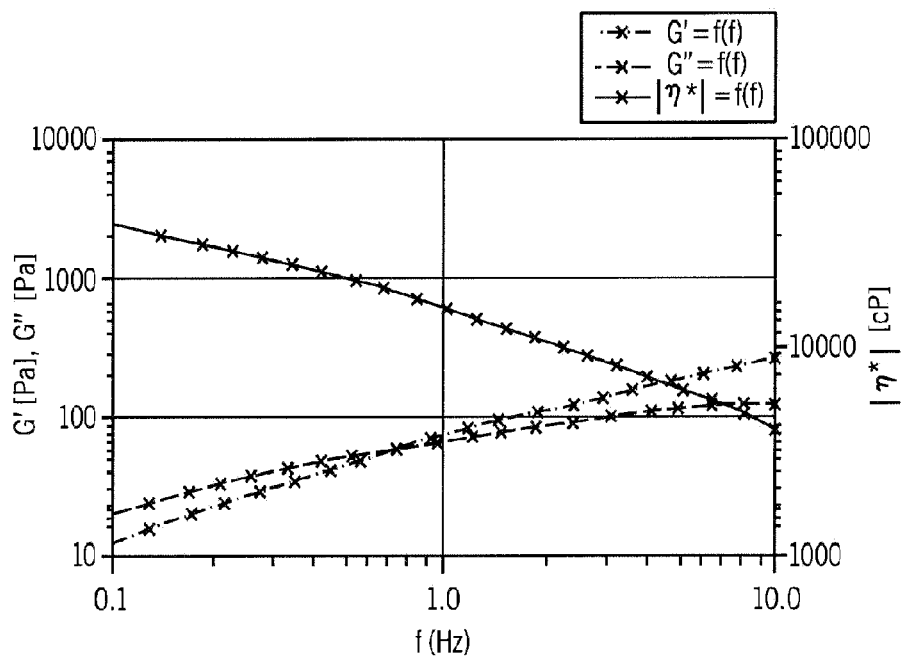
FIG. 22 illustrates a plot of elastic and viscous modulus and complex viscosity as a function of frequency for the composition of Example 13.

Sodium carboxymethylcellulose was prepared in sterile 25 mM to 100 mM potassium phosphate buffer adjusted to a pH of from about 7.2 to about 8.0 using potassium hydroxide and containing up to 1% glycerin. The dispersion was mixed in an orbital Ross mixer @1725 RPM for 5 minutes followed by mixing in an orbital Ross mixer @1725 RPM for 40 minutes while holding a vacuum @26 mm Hg or more. The composition was then steam sterilization at 121° C. for times ranging from 3 minutes to 12 minutes. In addition, one sample was sterilized for time intervals between 3 minutes and 12 minutes @121° C. Results are shown in FIG. 22 where G' represents the elastic modulus, G" represents the viscous modulus and η the complex viscosity. The profile shows that G' and G" intersect at 0.914 Hz (5.7 rad/sec). Above this frequency, the composition exhibits non-Newtonian solution characteristics (tan δ<1.0). The addition of glycerin to sodium CMC gel in potassium phosphate significantly affects the rheology of the composition, changing it from a fundamentally Newtonian fluid to a non-Newtonian fluid above a frequency of about 1.0.

Example 14

Preparation of 2.9% Sodium CMC Gel in Potassium Phosphate Buffer and Glycerin

Figure 23:
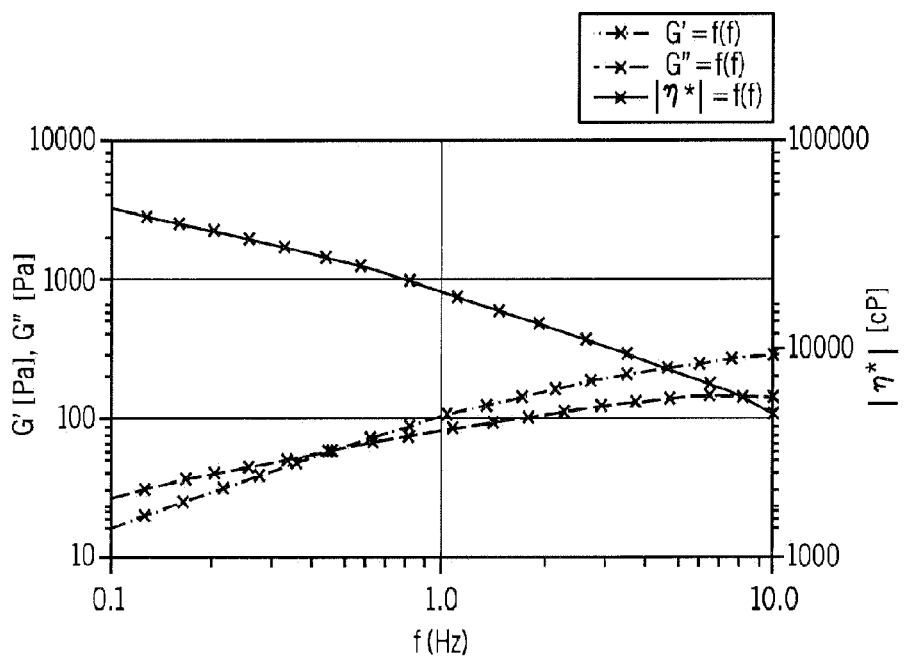
FIG. 23 illustrates a plot of elastic and viscous modulus and complex viscosity as a function of frequency for the composition of Example 14.

Sodium carboxymethylcellulose was prepared in sterile 25 mM to 100 mM potassium phosphate buffer adjusted to a pH of from about 7.2 to about 8.0 using potassium hydroxide and containing up to 1% glycerin. The dispersion was mixed in an orbital Ross mixer @1725 RPM for 5 minutes followed by mixing in an orbital Ross mixer @1725 RPM for 40 minutes while holding a vacuum @26 mm Hg or more. The composition was then steam sterilization at 121° C. for times ranging from 3 minutes to 12 minutes. In addition, one sample was sterilized for time intervals between 3 minutes and 12 minutes @121° C. Results are shown in FIG. 23 where G' represents the elastic modulus, G" represents the viscous modulus and η the complex viscosity. The profile shows that G' and G" intersect at 1.065 Hz (6.7 rad/sec). Above this frequency, the composition exhibits non-Newtonian solution characteristics (tan δ<1.0). The addition of glycerin to sodium CMC gel in potassium phosphate significantly affects the rheology of the composition, changing it from a fundamentally Newtonian fluid to a non-Newtonian fluid above a frequency of about 1.0.

Example 15

1150 C Sintered Materials Include the Following Materials and Process Conditions Materials of this exampled included implants having: 30% to 45% Media; 2.6% to 3.25% CMC; 0 to 15% glycerin; 0 mM to 100 mM PBS.

The CMC, buffer, glycerin and media were added together and mixed with a planetary mixer for 20 minutes to 3 hours under continuous and sustained vacuum. Materials were filled into 1 cc syringes, pouched in aluminum foil and terminally steam sterilized @121° C for 15 min to 30 minutes.

The rheology evaluation was carried out on 30% and 40% media, 2.6% CMC to 3.25% CMC, 1.5% to 15% glycerin, 0 to 25 mM. The results of which are shown in FIGS. 24-28. The materials tested and some of their properties are listed in Table A below. The first column implant is that as taught in prior art. The second column implant is in accordance with the principles of the present invention for use in high mobility tissues. The third column implant is also in accordance with the principles of the present invention, but for usage in higher bulking required tissues situations where contour shaping and the filling is of principle concern.

TABLE A

| Physical parameters/<br>Material composition | 30% CaHA—<br>3.25% CMC;<br>15% glycerin | 30% CaHA—<br>2.6% CMC;<br>1.5% glycerin | 40% CaHA—<br>2.6% CMC;<br>1.5% glycerin |
|---|---|---|---|
| Osmolality (mmol/kg) | 1768 to 2300 | 291 | 289 |
| Extrusion Force (lbf, 0.5" 27 Ga.) | 6.1 | 5.4 | 4.8 |
| Extrusion Force (lbf, 1.25" 27 Ga.) | 11.5 | 9.8 | 7.6 |
| Viscosity (η @0.5 Hz) | 413750 | 202865 | 396585 |
| Tan δ @0.5 Hz | 0.453 | 0.595 | 0.581 |
| Viscosity modulus (G" @0.5 Hz) | 1478.60 | 678.32 | 1331.8 |
| Loss Modulus (G' @0.5 Hz) | 671.69 | 404.30 | 773.23 |

Figure 24:
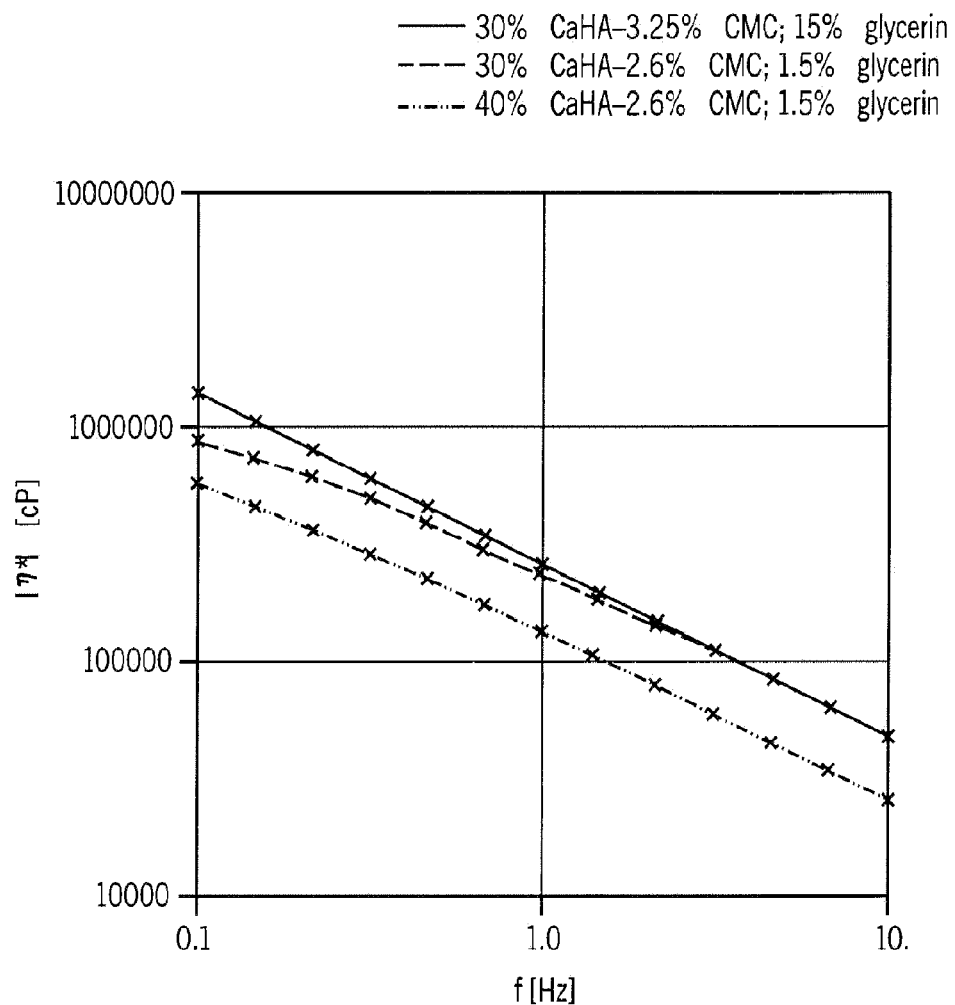
FIG. 24 illustrates the viscosities for each of the materials as sheer rate varies.
Figure 25:
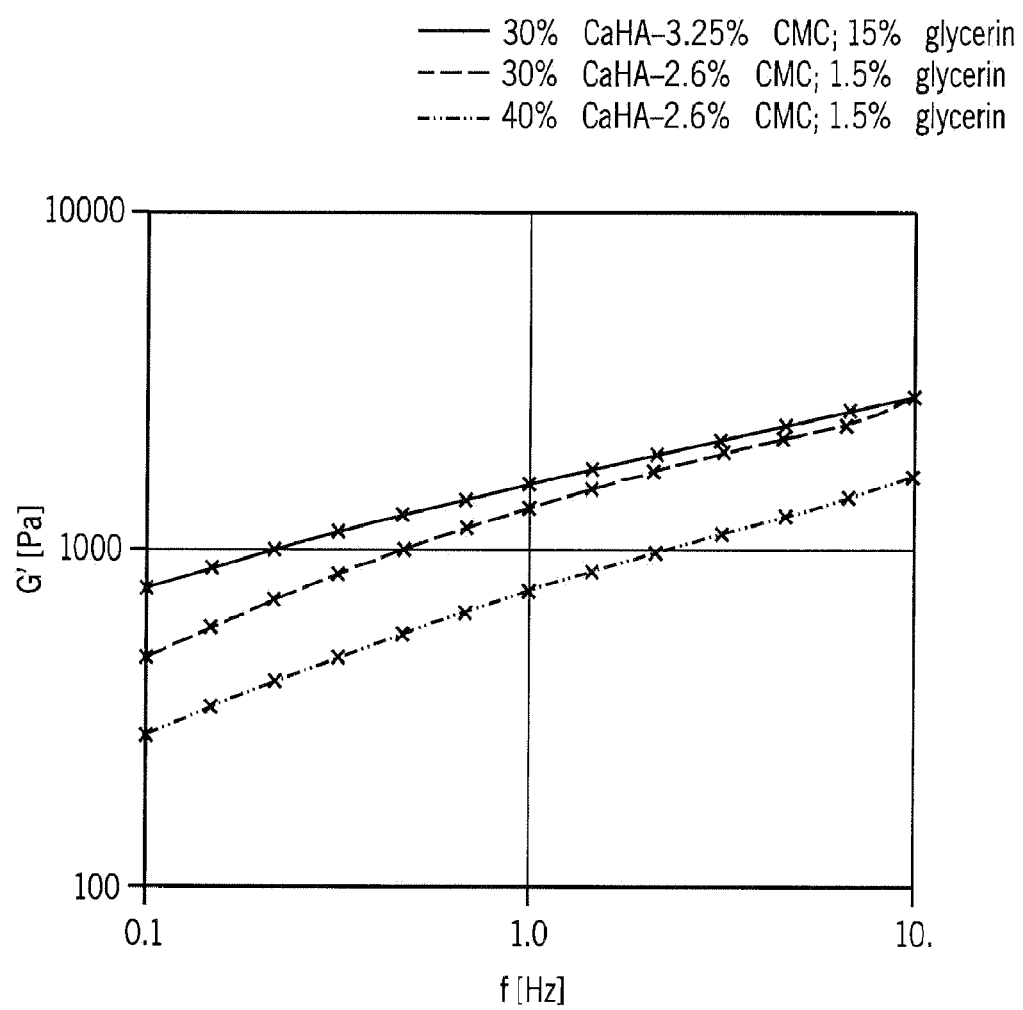
FIG. 25 illustrates the loss modulus for each of the materials as sheer rate varies.
Figure 26:
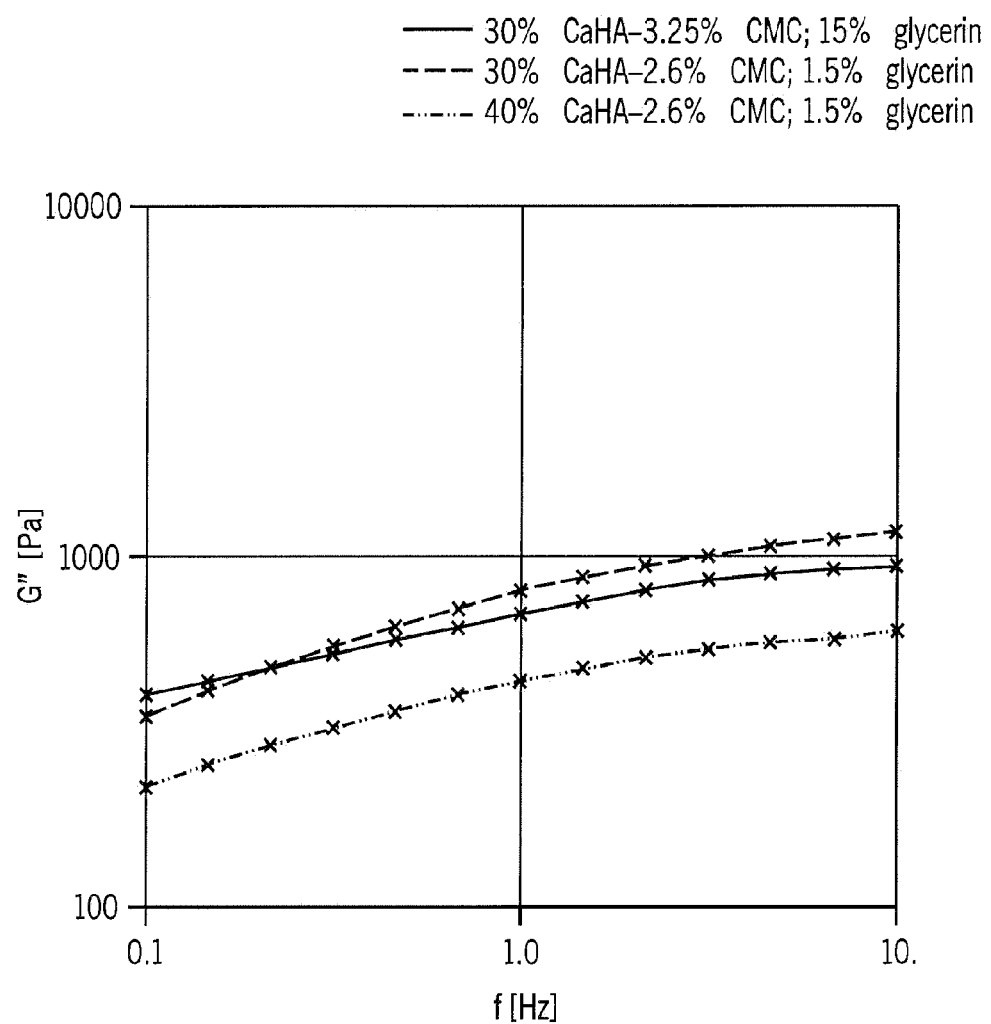
FIG. 26 illustrates the viscosity modulus for each of the materials as sheer rate varies.
Figure 27:
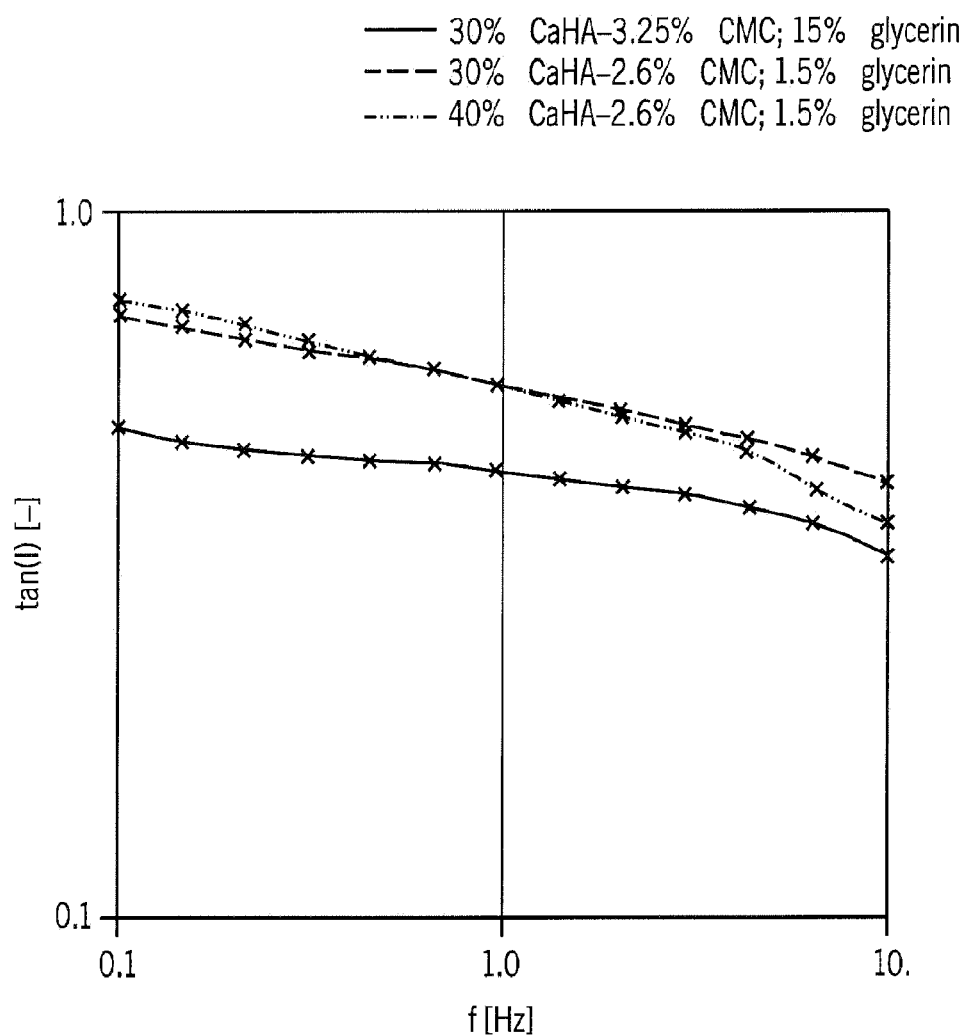
FIG. 27 illustrates the tan $\delta$ for each of the materials as sheer rate varies.

FIG. 24 illustrates the viscosities for each of the materials as shear rate varies. FIG. 25 illustrates the loss modulus for each of the materials as sheer rate varies. FIG. 26 illustrates the viscosity modulus for each of the materials as sheer rate varies. FIG. 27 illustrates the δ for each of the materials as sheer rate varies.

Material is shear thinning. Varying the gel composition concentrations within the gel carrier, offers the potential to mimic other rheological variables at higher % particle medias. Degradation rates of the particles can be manipulated through formulation in gel rheology. The descriptive characteristics of viscosity and elasticity can be varied or maintained through gel composition concentrations. The lower viscosity modulus G" and loss modulus G' the more similar in magnitude to physiological tissues studies and further asserts the improved biocompatibility not previously reported in prior art.

Figure 28:
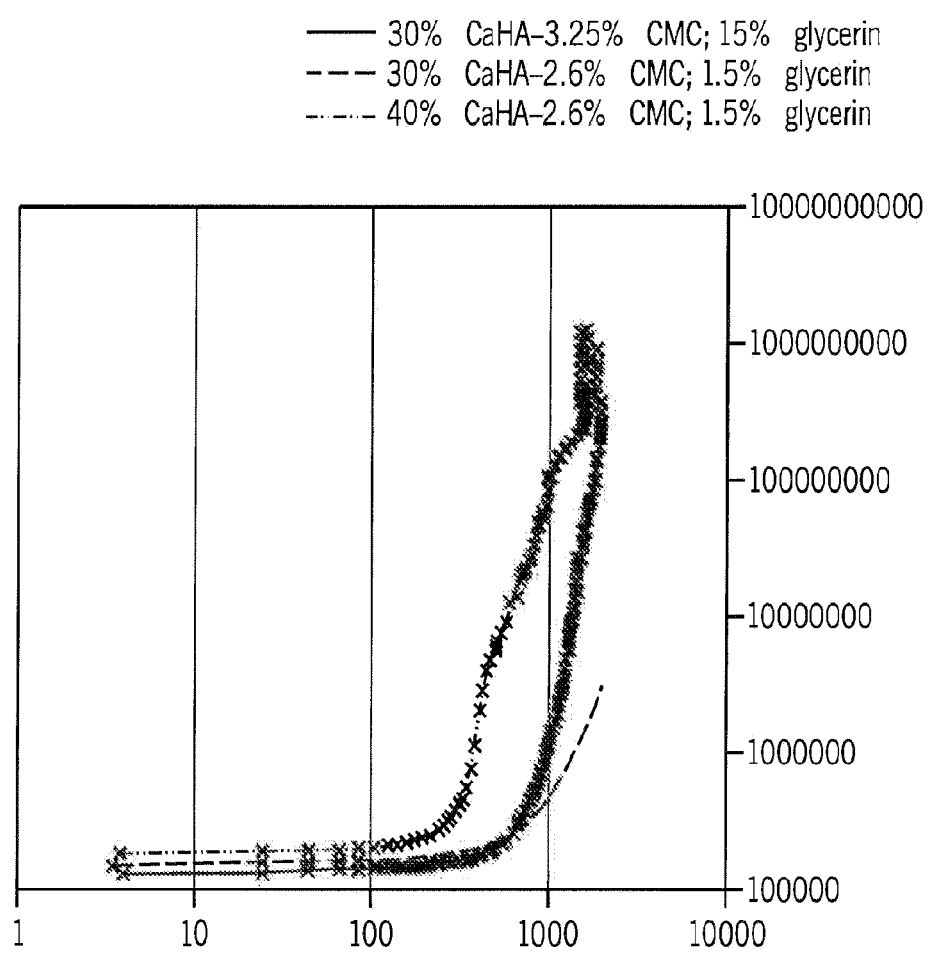
FIG. 28 demonstrates time dependency of the elasticity for varying gel compositions with varying concentrations of particles (30% & 40% solids in 2.6 CMC: 1.5% glycerin carrier vs. 30% solids in a 3.25% CMC: 15% glycerin carrier)

The time dependency of the elasticity is demonstrated in FIG. 28 for varying gel compositions with varying concentrations of particles. 30% & 40% solids in 2.6 CMC: 1.5% glycerin carrier vs. 30% solids in a 3.25% CMC: 15% glycerin carrier. The material demonstrates a time dependency to material break down due to composition. The material with less particles and lower viscosity gels have less tendency to withstand material stresses.

Example 16

Alginate/CMC carrier with glycerin was combined with CaHa particles which were sintered at 1150° C. and include the following constituents (Table B). Various alginate types have been tested and a summary of the alginates is set forth below in Table B.

TABLE B

Alginate (LVM, MVM, M = G, MVG and LVG)

| Alginate Type | Guluronic Acid %/Mannuronic acid (%) | Defintion |
|---|---|---|
| LVM | 30-35/65-70 | Low visocosity alginate gel with high mannuronic acid content. |
| MVM | 35-45/55-65 | Medium viscosity alginate gel with high mannuronic acid content. |
| M = G | 45-55/45-55 | High viscosity alginate gel similar in mannuronic and guluronic acid contents. |
| MVG | 65-75/25-35 | Low viscosity alginate gel that is cold soluble and has a high guluronic acid content. |
| LVG | 65-75/25-35 | Very low viscosity alginate gel with high guluronic acid content. |

M087052: was composed of 30% Media, 40 mg/ml to 100 mg/ml alginate: 7.5 mg/ml to 12.5 mg/ml, 25 mM PBS, and 1.5% glycerin.

The following Alginate/CMC gel formulations (mg/mL) were prepared using the process detailed below:

The Alginate/CMC, buffer, glycerin were added together and mixed for 20 min to 3 hours. Particles were then added in 30% by volume and mixed for 20 min to 3 hours. Materials were filled into 1 cc syringes, pouched in aluminum foil and terminally steam sterilized @121° C. for 15 min to 30 mins.

Figure 29:
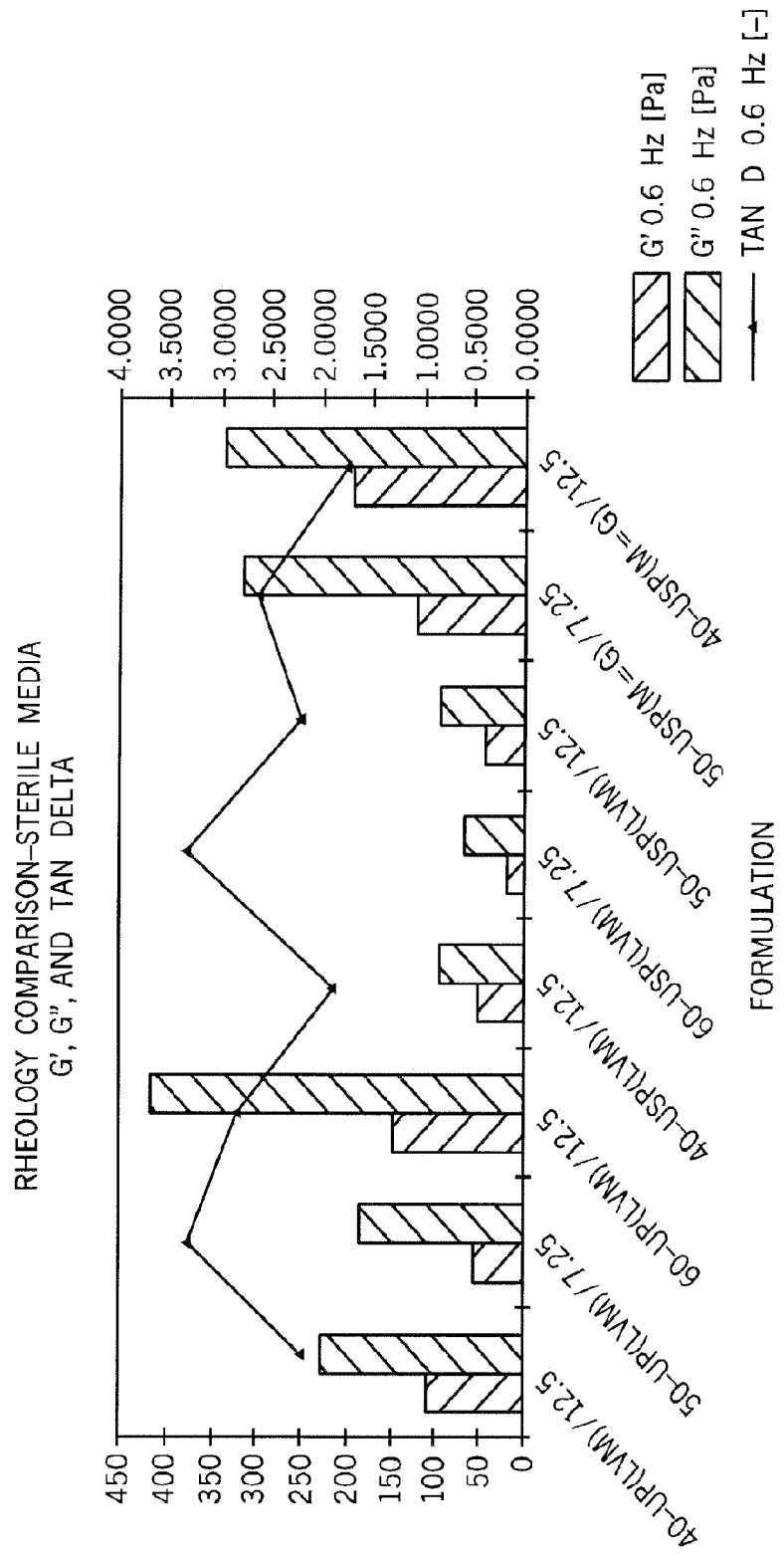
FIG. 29 illustrates the loss modulus G', the elastic modulus G" and tan $\delta$ (GIG") for compositions of Example 16.
Figure 30:
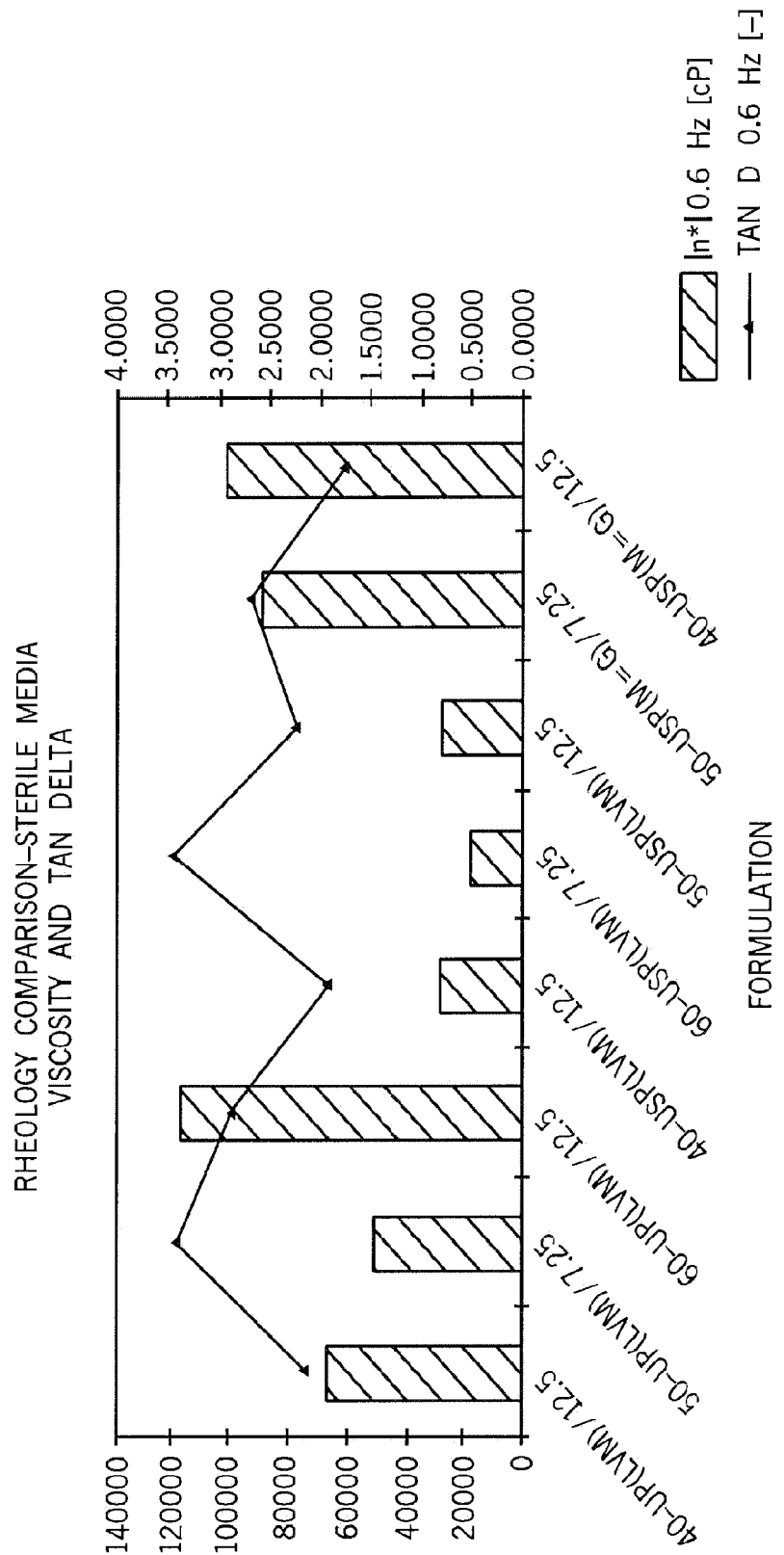
FIG. 30 illustrates viscosity and tan $\delta$ properties for compositions of Example 16.
Figure 31A:
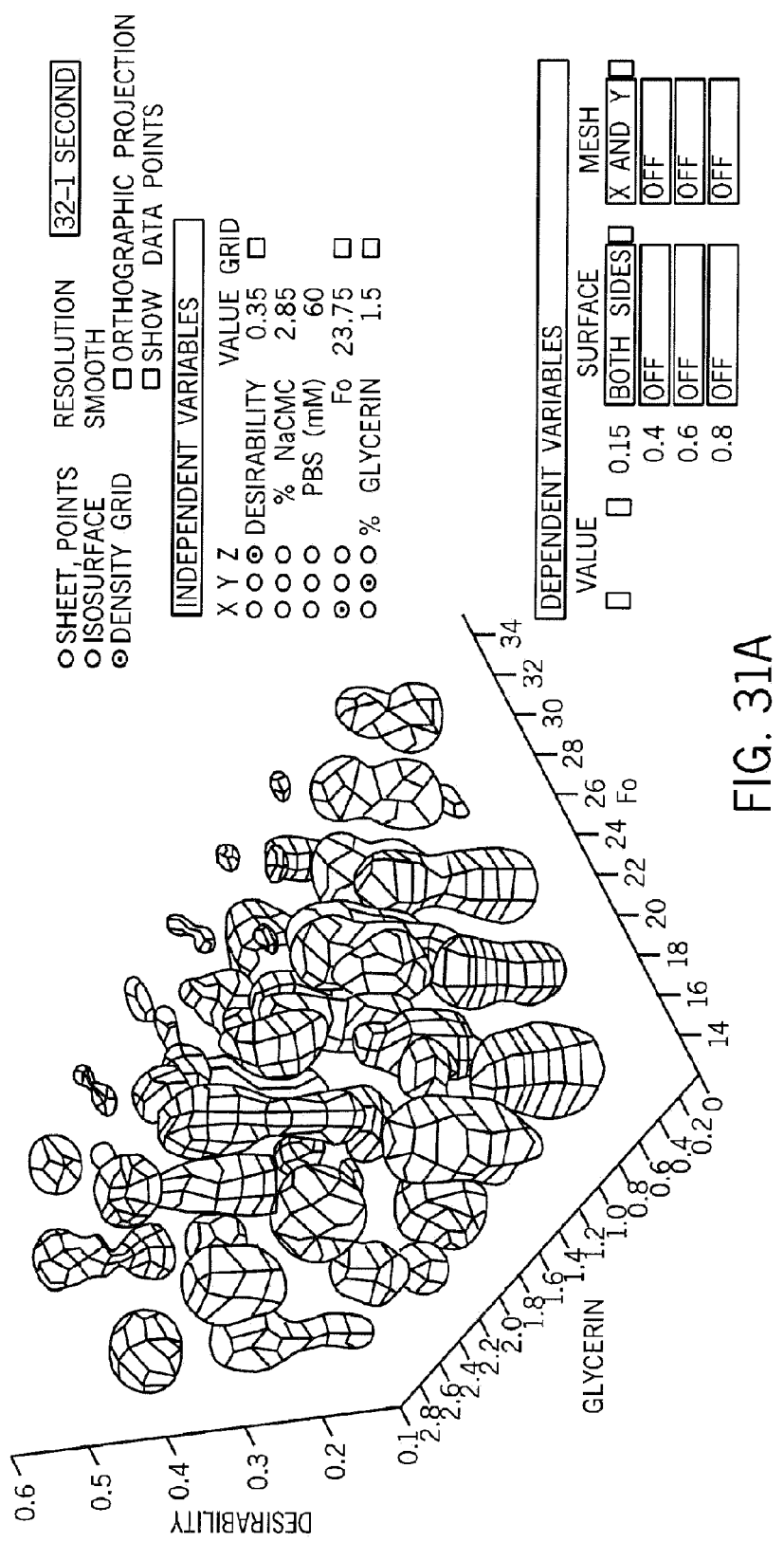
FIG. 31A shows a 3D desirability plot of glycerin versus Fo holding CMC and PBS constant.
Figure 31B:
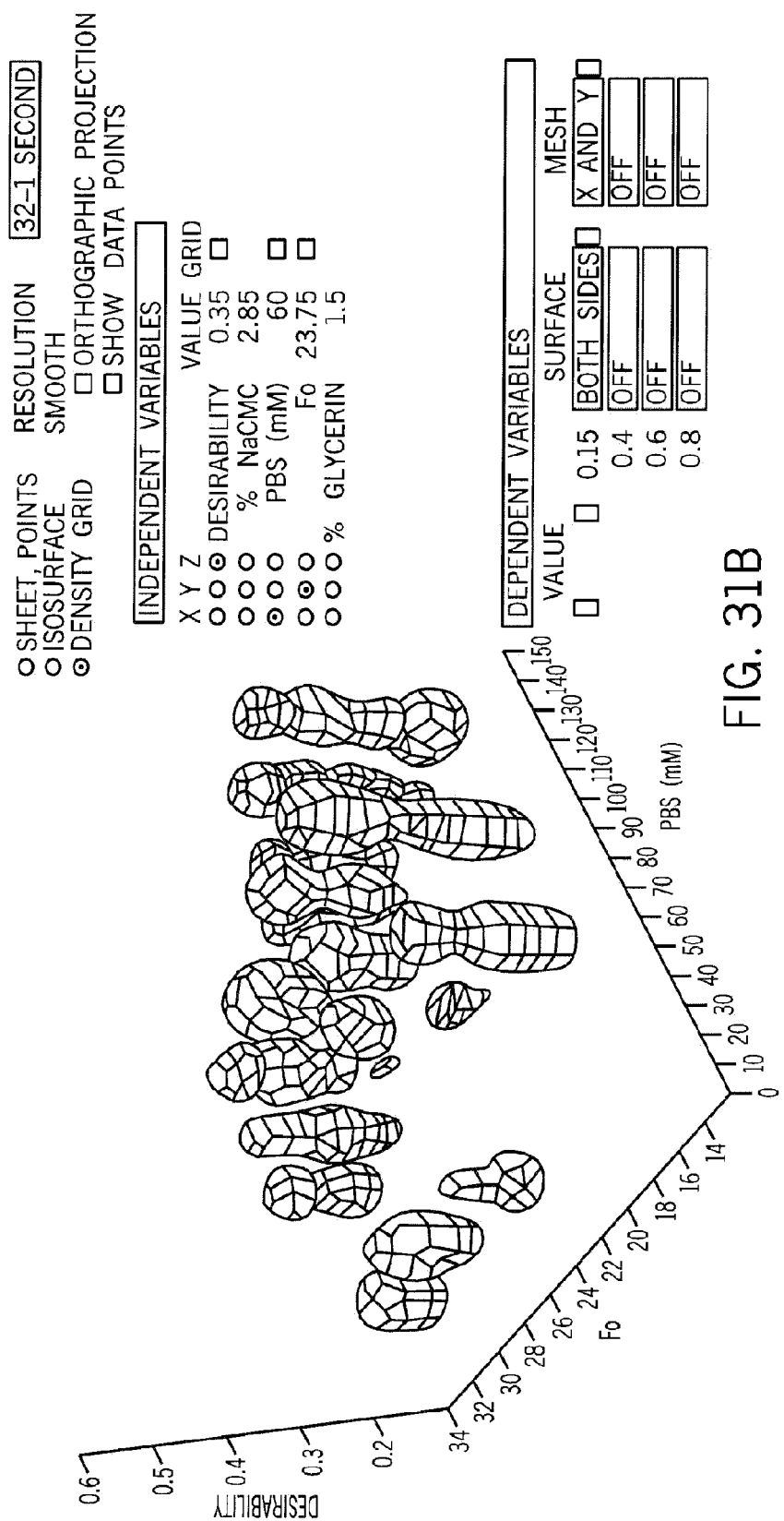
FIG. 31B shows Fo versus PBS holding CMC and glycerin constant.
Figure 31C:
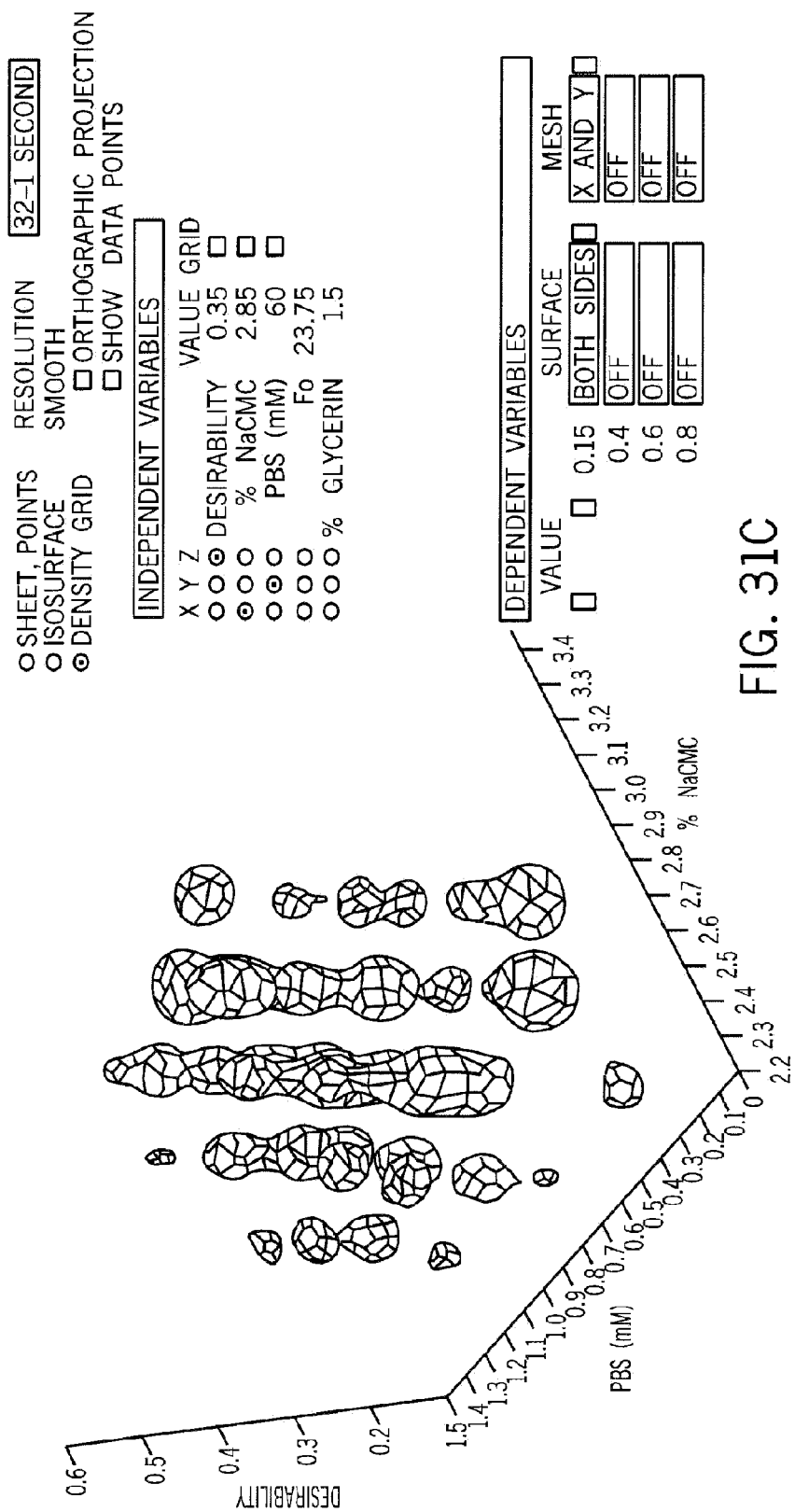
FIG. 31C shows PBS versus CMC holding glycerin and Fo constant.
Figure 31D:
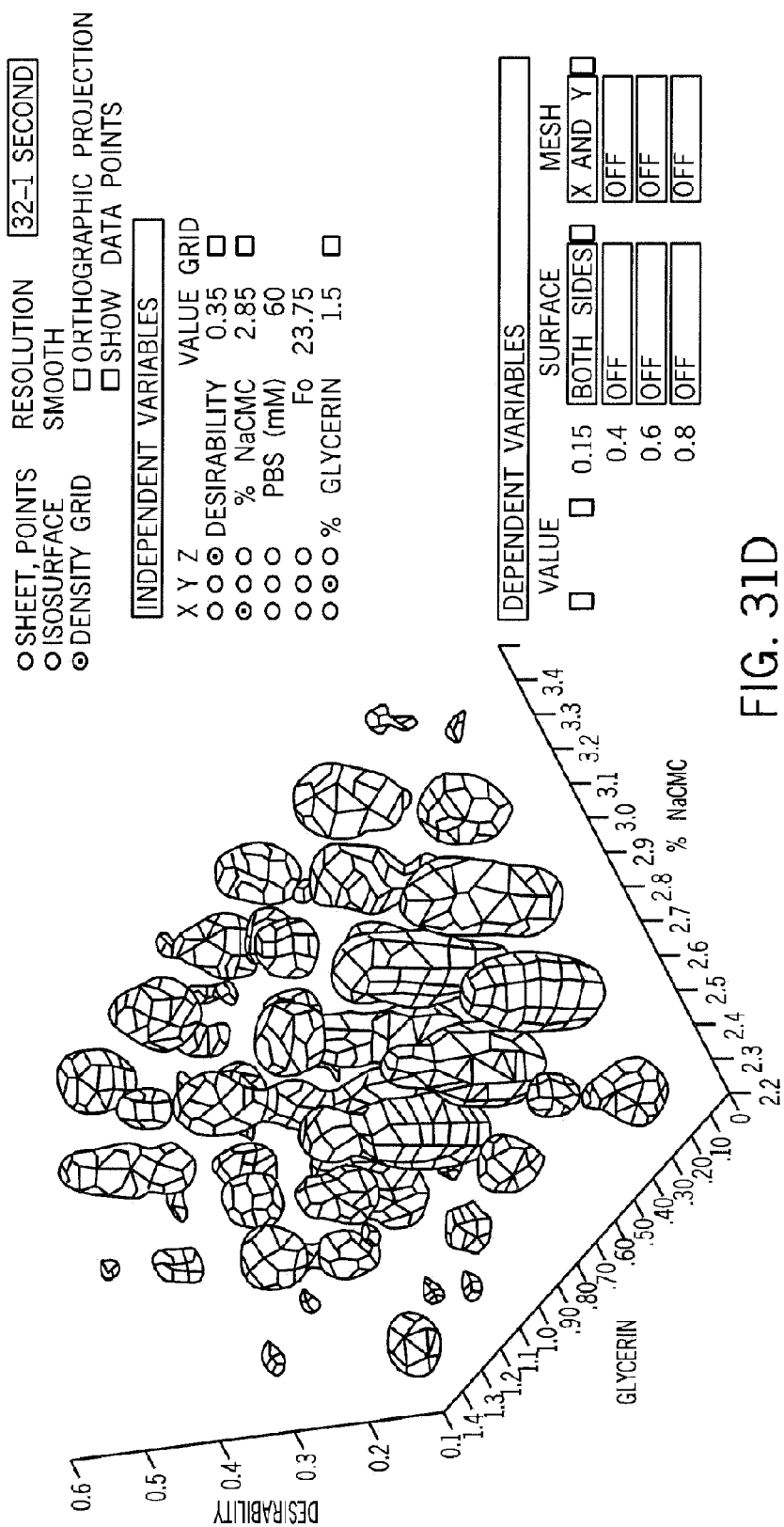
FIG. 31D shows glycerin versus CMC holding PBS and Fo constant.
Figure 31E:
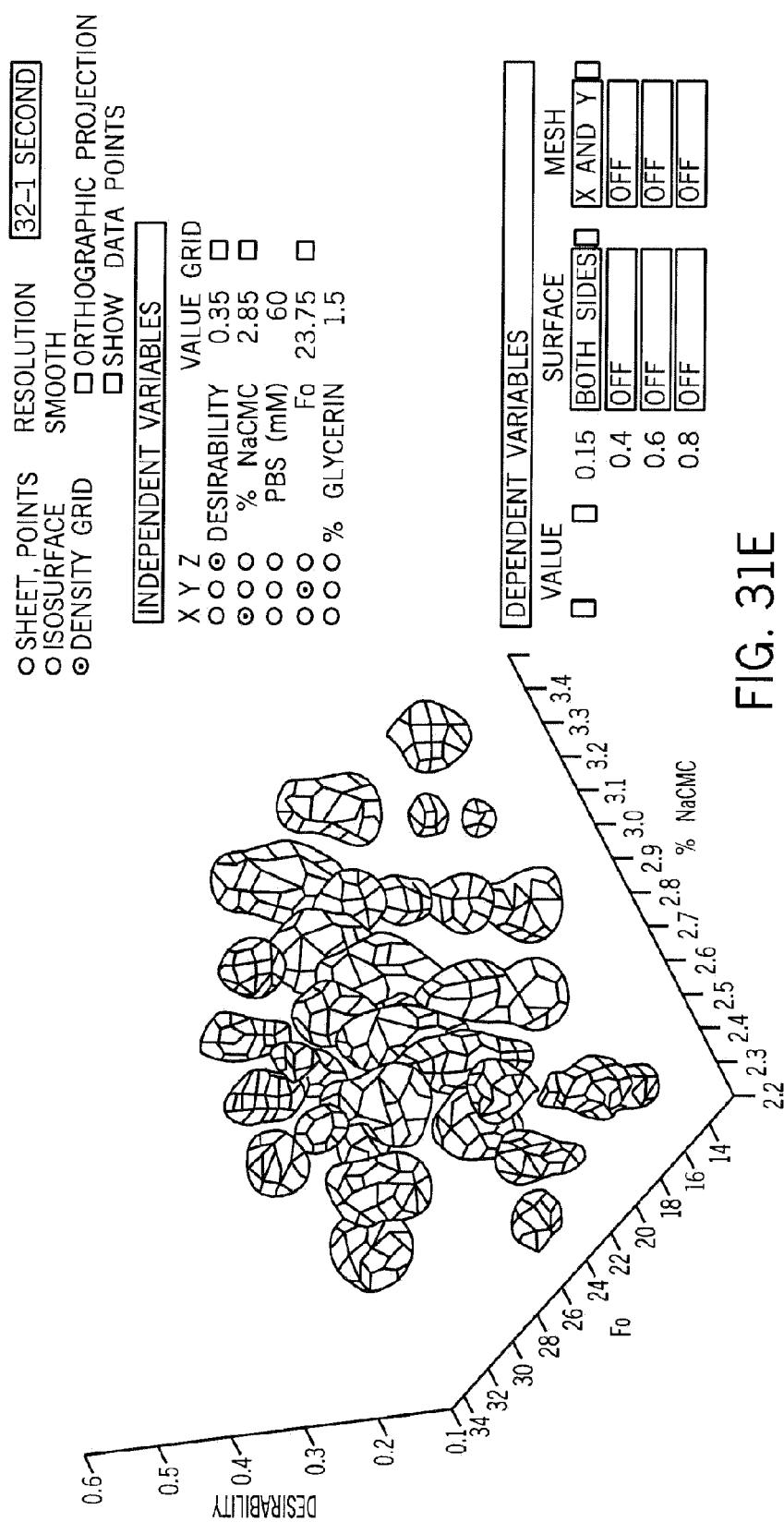
FIG. 31E shows Fo versus CMC holding PBS and glycerin constant.
Figure 31F:
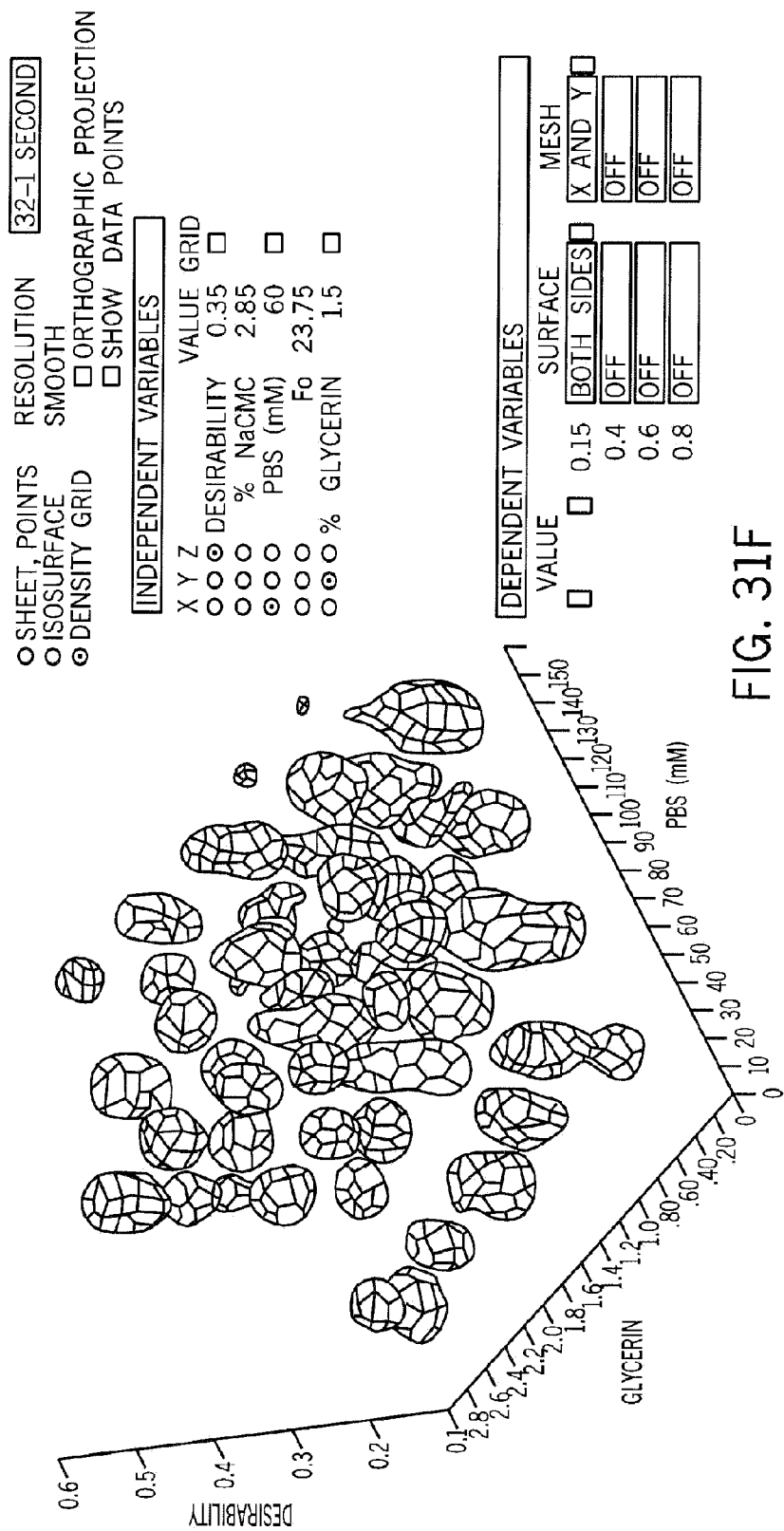
FIG. 31F shows glycerin versus PBS holding CMC and Fo constant.

Rheological evaluation for these materials are illustrated in the FIGS. 29 and 30. FIG. 29 illustrates the loss modulus G', the elastic modulus G" and tan δ (G'/G"). FIG. 30 illustrates viscosity and tan δ properties.

Example 17

Alginate (MVM, M=G or LVM—Various alginates/CMC gels were prepared and include the following constituents and processes:

G094035: 5 mg/ml to 100 mg/ml alginate (MVM, M=G or LVM (see Table B)): 2.5 mg/ml to 50 mg/ml CMC, 25 mM PBS, 1.5% glycerin. The following Alginate/CMC gel formulations (mg/mL) were prepared using the process detailed below:

The Alginate/CMC, buffer, glycerin were added together and mixed for 20 min to 3 hours with either an orbital rotary mixer or direct propeller mixer. Materials were filled into 1 cc syringes, pouched in aluminum foil and terminally steam sterilized @121°C for 15 min to 30 mins.

Example 18

In one embodiment, the implant may be designed for application in the laryngeal tissue. Table C lists the parameters for such an implant.

TABLE C

| Specification | Laryngeal Implant |
|---|---|
| Viscosity | 107,620-517,590 cps. |
| Osmolarity | 255 mas to 327 mOs |
| pH | 7.0 ± 1.0 |
| Loss on Drying | −29.7% to −43.1%. |
| Percent Solids | 54.3 to 70.5% |
| Extrusion Force | 3.60-7.20 lbsf |

Example 19

The prediction model was developed using the SAS JMP ver 7.0 statistical software. The prediction model data used the screening model's graphing scripts, which are mathematical equations of the surface contours of the models. These can be obtained by highlighting the model output and saving the response prediction formula to a data spreadsheet. Values populated the screening model with model outputs for the screening model inputs tested. The prediction model formulae were then exported to a separate spreadsheet, where a full factorial model design was developed. In one case, for example, the following optimized parameters based on the screening model were used: Sterilization (121°C) FO 22, 25, 28, and 33 respectively. The CMC concentration (% CMC) was varied between 2.3% w/v and 2.9% w/v in 0.1% w/v increments. The glycerin concentration (% gly) was held to 0% w/v, 1.0% w/v and 1.5% w/v. The buffer concentration (mM) was varied from 0.25 mM, 50 mM and 100 mM concentration. The model was populated with the screening model prediction formula outputs representing 625 individual runs. This then represents the whole prediction model using optimized sterilization inputs based on the same inputs for the screening model previously conducted. The model was then re-evaluated over the same output parameters using the Simulator function with 10000 runs.

Simulation allows the determination of the distribution of model outputs as a function of the random variation in the factors and model noise. The simulation facility in the profilers provides a way to set up the random inputs and run the simulations, producing an output table of simulated values. In this application the boundary conditions are estimated by the defect rate of a process that has been fit to specific rheological parameters to determine if it is robust with respect to variation in the factors. If specifications have been set in the response, they are carried over into the simulation output, allowing a prospective boundary analysis of the simulated model variable using new factors settings. In the Profiler function, the Simulator function is integrated into the graphical layout. Factor specifications are aligned below each factor's profile. A simulation histogram is shown in FIG. 9B on the right for each response.

Factors (inputs) and response (outputs) are already given roles by being in the Profiler. Additional specifications for the simulator are including assigning random values to the factors and adding random noise to the responses.

For each factor, the assignment of values is important. The Random program assigns the factor a random value with the specified distribution and distributional parameters.

Normal truncated is a normal distribution limited by lower and upper limits. Any random realization that exceeds these limits is discarded and the next variate within the limits is chosen. This is used to simulate an inspection system where inputs that do not satisfy specification limits are discarded or sent back.

The Add Random Noise function obtains the response by adding a normal random number with the specified standard to the evaluated model.

The Defect Profiler function shows the defect rate as an isolated function of each factor. This command is enabled when specification limits are available, as described below.

The Profiler function displays profile traces. A profile trace is the predicted response as one variable is changed while the others are held constant at the current values. The Profiler re-computes the profiles and provides predicted responses (in real time) as the value of an X variable is varied. The vertical dotted line for each X variable shows its current value or current setting.

For each X variable, the value above the factor name is its current value.

The horizontal dotted line shows the current predicted value of each Y variable for the current values of the X variables.

Figure 9B:
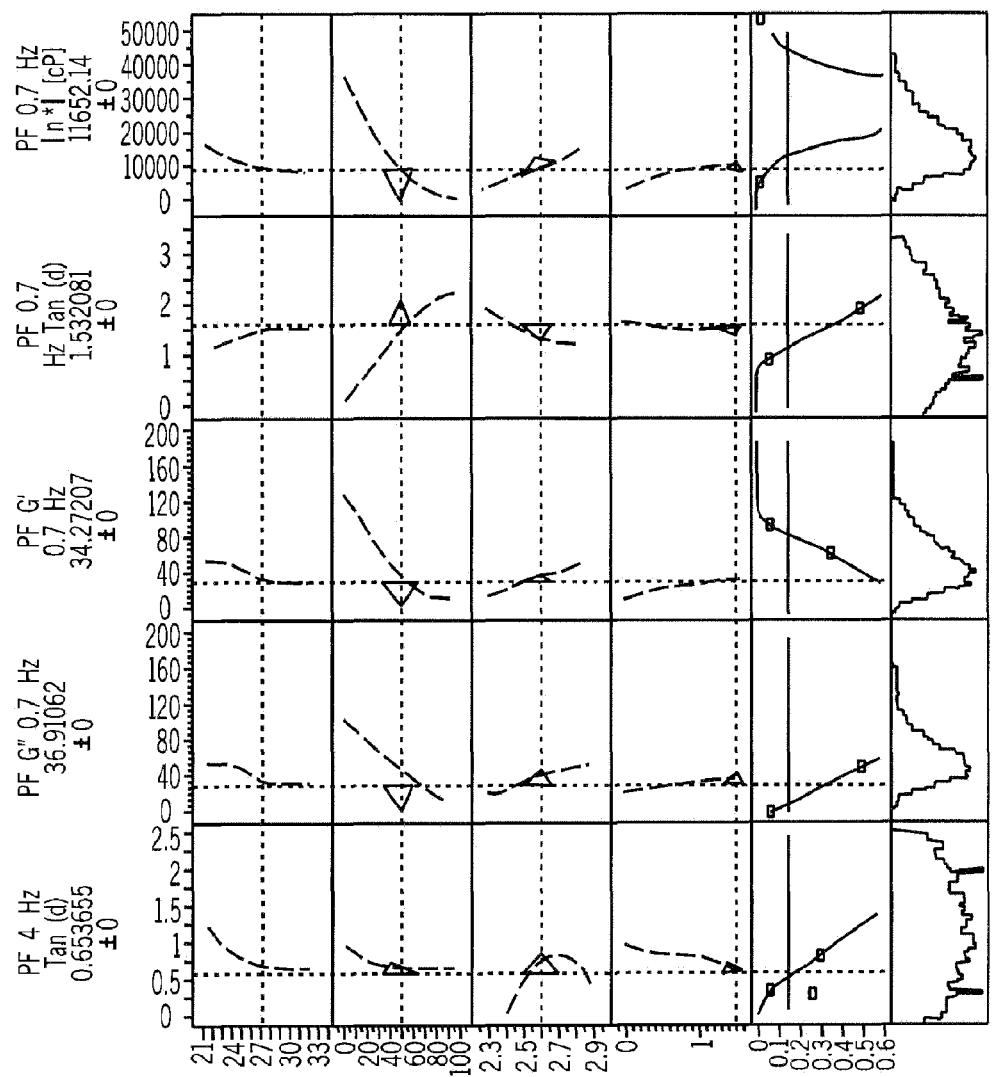
FIG. 9B is a prediction profile set and shows columns of rheological behavior for various chemical variables, each taken from a cross-section from the contours of FIGS. 9A(i)-9A(ix)

The black lines within the plots of FIG. 9B show how the predicted value changes when the current value of an individual X variable is changed. In fitting platforms, the 95% confidence interval for the predicted values is shown by a dotted blue curve surrounding the prediction trace (for continuous variables) or the context of an error bar (for categorical variables).

The Profiler is then a way of changing one variable at a time and looking at the effect on the predicted response.

There are several important points to note when interpreting a prediction profile:

1. The importance of a factor can be assessed to some extent by the steepness of the prediction trace. If the model has curvature terms (such as squared terms), then the traces may be curved.

2. If you change a factor's value, then its prediction trace is not affected, but the prediction traces of all the other factors can change. The Y response line must cross the intersection points of the prediction traces with their current value lines.

3. Note: If there are interaction effects or cross-product effects in the model, the prediction traces can shift their slope and curvature as you change current values of other terms. That is what interaction is all about. If there are no interaction effects, the traces only change in height, not slope or shape.

Prediction profiles are especially useful in multiple-response models to help judge which factor values can optimize a complex set of criteria.

The Profiler shows the confidence bars on the prediction traces of continuous factors, along with the sensitivity Indicator displayed in triangles, whose height and direction correspond to the value of the derivative of the profile function at its current value. This is useful in large profiles to be able to quickly spot the sensitive cells.

The prime reason to make random factor tables is to explore the factor space in a multivariate way using graphical queries. This technique is called Filtered Monte Carlo. This allows visualization of the locus of all factor settings that produce a given range to desirable response settings. By selecting and hiding the points that do not qualify (using graphical brushing or the Data Filter), the remaining opportunity space yields the result desired.

The Simulator enables the creation of Monte Carlo simulations using random noise added to factors and predictions for the model. Fixed factors were set over a range of settings and allowed for 1 s·d of model noise to random values to determine the rate that the responses are outside the specification limits.

Often there are multiple responses measured for each set of experimental conditions, and the desirability of the outcome involves several or all of these responses. For example, one response can be maximized while another is minimized, and a third response kept close to some target value. In desirability profiling, a desirability function is specified for each response. The overall desirability can be defined as the geometric mean of the desirability for each response.

The Desirability Profiler function components and examples of desirability functions settings are discussed next. The desirability functions are smooth piecewise functions that are crafted to fit the control points.

The minimize and maximize functions are three-part piecewise smooth functions that have exponential tails and a cubic middle.

The target function is a piecewise function that is a scale multiple of a normal density on either side of the target (with different curves on each side), which is also piecewise smooth and fit to the control points.

These choices give the functions good behavior as the desirability values switch between the maximize, target, and minimize values.

The control points are not allowed to reach all the way to zero or one at the tail control points.

Maximize Function

The default desirability function setting is maximize ("higher is better"). The top function handle is positioned at the maximum Y value and aligned at the high desirability, close to 1. The bottom function handle is positioned at the minimum Y value and aligned at a low desirability, close to 0.

Target Function

A target value can be designated as "best." In this example, the middle function handle is positioned at Y=55 and aligned with the maximum desirability of 1. Y becomes less desirable as its value approaches either 70 or 42. The top and bottom function handles at Y=70 and Y=42 are positioned at the minimum desirability close to 0.

Minimize Function

The minimize ("smaller is better") desirability function associates high response values with low desirability and low response values with high desirability. The curve is the maximization curve flipped around a horizontal line at the center of plot.

The Desirability Profile

The last row of plots in FIG. 9B shows the desirability trace for each response. The numerical value beside the word Desirability on the vertical axis is the geometric mean of the desirability measures. This row of plots shows both the current desirability and the trace of desirabilities that result from changing one factor at a time.

Desirability Profiling for Multiple Responses

A desirability index becomes especially useful when there are multiple responses.

Defect Rate Function

The defect rate shows the probability of an out-of-specification output defect as a function of each factor, while the other factors vary randomly. This is used to help visualize which factor's distributional changes the process is most sensitive to, in the quest to improve the description of the boundary functions.

Specification limits define what is a defect, and random factors provide the variation to produce defects in the simulation. Both need to be present for a Defect Profile to be meaningful.

The institution of a lower limit acceptable desirability is appropriate since analysis is based on finite data sampling and the lower limit was instituted to be values greater than 0.15. Based on those limitations, the whole simulation model has the following limiting parameters as follows.

FO=24 to 35
PBS=22 mM to 140 mM
% CMC=2.3% w/v to 3.3% w/v
% Glycerin=0.3% w/v to 2.5 w/v However, individual experimentation has identified limiting parameters that are most favorable for producing the outputs within the specification range, while maintaining a sterile product. Their conditions are as follows:

FO=22 to 30
PBS=25 mM to 100 mM
% CMC=2.3% w/v to 2.9% w/v
% Glycerin=0% w/v to 1.5% w/v An example of the 2D and 3D plots which result are shown in FIGS. 31A-31F. These figures show the evaluation of the desirability function expressed as a function two of the following design inputs: % CMC, Fo; % glycerin and PBS. The boundary limiting condition for the percent CMC vs. Fo is defined by the 0.7 Hz tan δ contour trace from 2.3 to 2.7. The 2D plot shows a white region within which the rheological parameter is met and is consistent with the desirability function shown in FIG. 9B.

The model trace formulae for the whole model are as follows for the following outputs.

Prediction Formula Viscosity 0.7 Hz:
(−0.0662001910451557)+0.051920253378124*:Fo+0.0146791342721163*:Name("PBS (mM)")+−0.218700904653452*:Name("% NaCMC")+−0.0202956176083598*:Name(% Glycerin")+(:Fo−22.0003631356491)*((:Fo−22.0003631356491)*−0.00371533851417633)+(:Fo−22.0003631356491)*((:Name("PBS (mM)")−63.5057099845838)*0.000185185074554069)+(:Name("PBS (mM)")−63.5057099845838)*((:Name("PBS (mM)")−63.5057099845838)*−0.0000863865657255508)+(:Fo−22.0003631356491)*((:Name("% NaCMC")−2.85245995014651)*−0.0322726861725922)+(:Name("PBS (mM)")−63.5057099845838)*((:Name("% NaCMC")−2.85245995014651)*−0.0152609626718641)+(:Name("% NaCMC")−2.85245995014651)*((:Name("% NaCMC")−2.85245995014651)*0.942295293128045)+(:Fo−22.0003631356491)*((:Name("% Glycerin")−1.49703269551474)*0.0048399350260245)+(:Name("PBS (mM)")−63.5057099845838)*((:Name("% Glycerin")−1.49703269551474)*0.00387275533427914)+(:Name("% NaCMC")−2.85245995014651)*((:Name("% Glycerin")−1.49703269551474)*−0.213067717437202)+(:Name("% Glycerin")−1.49703269551474)*((:Name("% Glycerin")−1.49703269551474)*0.052309021299775)

Prediction Formula Tan δ0.7 Hz:
(−0.0662001910451557)+0.051920253378124*:Fo+0.0146791342721163*:Name("PBS (mM)")+−0.218700904653452*:Name("% NaCMC")+−0.0202956176083598*:Name("% Glycerin")+(:Fo−22.0003631356491)*((:Fo−22.0003631356491)*−0.00371533851417633)+(:Fo−22.0003631356491)*((:Name("PBS (mM)")−63.5057099845838)*0.000185185074554069)+(:Name("PBS (mM)")−63.5057099845838)*((:Name("PBS (mM)")−63.5057099845838)*−0.0000863865657255508)+(:Fo−22.0003631356491)*((:Name("% NaCMC")−2.85245995014651)*−0.0322726861725922)+(:Name("PBS (mM)")−63.5057099845838)*((:Name("% NaCMC")−2.85245995014651)*−0.0152609626718641)+(:Name("% NaCMC")−2.85245995014651)*((:Name("% NaCMC")−2.85245995014651)*0.942295293128045)+(:Fo−22.0003631356491)*((:Name("% Glycerin")−1.49703269551474)*0.0048399350260245)+(:Name("PBS (mM)")−63.5057099845838)*((:Name("% Glycerin")−1.49703269551474)*0.00387275533427914)+(:Name("% NaCMC")−2.85245995014651)*((:Name("% Glycerin")−1.49703269551474)*−0.213067717437202)+(:Name("% Glycerin")−1.49703269551474)*((:Name("% Glycerin")−1.49703269551474)*0.052309021299775)

Prediction Formula G' 0.7 Hz: 65.1530428282072+−4.56421653385048*:Fo+−1.24220316891102*:Name("PBS (mM)")+53.0767618580076*:Name("% NaCMC")+9.296089270897*:Name("% Glycerin")+(:Fo−22.0003631356491)*((:Fo−22.0003631356491)*0.185460632264244)+(:Fo−22.0003631356491)*((:Name("PBS (mM)")−63.5057099845838)*0.0152064998484757)+(:Name("PBS (mM)")−63.5057099845838)*((:Name("PBS (mM)")−63.5057099845838)*0.0121675367725622)+(:Fo−22.0003631356491)*((:Name("% NaCMC")−2.85245995014651)*−1.59402906490529)+(:Name("PBS (mM)")−63.5057099845838)*((:Name("% NaCMC")−2.85245995014651)*−0.82120066059178)+(:Name("% NaCMC")−2.85245995014651)*((:Name("% NaCMC")−2.85245995014651)*−3.41806241403989)+(:Fo−22.0003631356491)*((:Name("% Glycerin")−1.49703269551474)*−0.194222622094197)+(:Name("PBS (mM)")−63.5057099845838)*((:Name("% Glycerin")−1.49703269551474)*−0.237225958870055)+(:Name("% NaCMC")−2.85245995014651)*((:Name("% Glycerin")−1.49703269551474)*−0.363919647719381)+(:Name("% Glycerin")−1.49703269551474)*((:Name("% Glycerin")−1.49703269551474)*−0.960279042125364)

Prediction Formula G" 0.7 Hz: 42.340284211014+−4.44571705075887*:Fo+−0.951595662768327*:Name("PBS (mM)")+57.6631139101727*:Name("% NaCMC")+4.93958206506618*:Name("% Glycerin")+(:Fo−22.0003631356491)*((:Fo−22.0003631356491)*0.1897777224472)+(:Fo−22.0003631356491)*((:Name("PBS (mM)")−63.5057099845838)*0.00526490794925264)+(:Name("PBS (mM)")−63.5057099845838)*((:Name("PBS (mM)")−63.5057099845838)*0.0075094419087303)+(:Fo−22.0003631356491)*((:Name("% NaCMC")−2.85245995014651)*−1.59674778661272)+(:Name("PBS (mM)")−63.5057099845838)*((:Name("% NaCMC")−2.85245995014651)*−0.55449874562251)+(:Name("% NaCMC")−2.85245995014651)*((:Name("% NaCMC")−2.85245995014651)*17.0085346258082)+(:Fo−22.0003631356491)*((:Name("% Glycerin")−1.49703269551474)*−0.0425836269658459)+(:Name("PBS (mM)")−63.5057099845838)*((:Name("% Glycerin")−1.49703269551474)*−0.187414471985777)+(:Name("% NaCMC")−2.85245995014651)*((:Name("% Glycerin")−1.49703269551474)*−2.3241038908658)+(:Name("% Glycerin")−1.49703269551474)*((:Name("% Glycerin")−1.49703269551474)*−0.73370622281908)

Prediction Formula Tan δ 4 Hz 9.45512533634532+−0.126696086121843*:Fo+−0.00117658850182967*:Name("PBS (mM)")+−2.00308587650446*:Name("% NaCMC")+0.165674034118311*:Name("% Glycerin")+(:Fo−22.0003631356491)*((:Fo−22.0003631356491)*0.00365527346963407)+(:Fo−22.0003631356491)*((:Name("PBS (mM)")−63.5057099845838)*0.000511204818741645)+(:Name("PBS (mM)")−63.5057099845838)*((:Name("PBS (mM)")−63.5057099845838)*0.0000499689391927876)+(:Fo−22.0003631356491)*((:Name("% NaCMC")−2.85245995014651)*−0.0624166549775326)+(:Name("PBS (mM)")−63.5057099845838)*((:Name("% NaCMC")−

2.85245995014651)*0.0199800709717944)+(:
Name("% NaCMC")−2.85245995014651)*((:
Name("% NaCMC")−2.85245995014651)*−
8.94890476212236)+(:Fo−22.0003631356491)*
((:Name("% Glycerin")−1.49703269551474)*−
0.0266258304941918)+(:Name("PBS (mM)")−
63.5057099845838)*((:Name("% Glycerin")−
1.49703269551474)*−0.0159932411399036)+(:
Name("% NaCMC")−2.85245995014651)*((:
Name("% Glycerin")−1.49703269551474)
*1.21969695165947)+(:Name("% Glycerin")−
1.49703269551474)*((:Name("% Glycerin")−
1.49703269551474)*0.00451334325524632)

Prediction Formula G' 4.0 Hz 119.421921614245+−
12.2323465265668*:Fo+−2.68101314812006*:
Name("PBS (mM)")+146.999647742916*:Name
("% NaCMC")+27.8854022682617*:Name("%
Glycerin")+(:Fo−22.0003631356491)*((:Fo−
22.0003631356491)*0.519903664055683)+(:
Fo−22.0003631356491)*((:Name("PBS (mM)
")−63.5057099845838)*0.0209551675180216)+
(:Name("PBS (mM)")−63.5057099845838)*((:
Name("PBS (mM)")−63.5057099845838)
*0.0233180450227683)+(:Fo−
22.0003631356491)*((:Name("% NaCMC")−
2.85245995014651)*−3.12498688301935)+(:
Name("PBS (mM)")−63.5057099845838)*((:
Name("% NaCMC")−2.85245995014651)*−
1.68010649138557)+(:Name("% NaCMC")−
2.85245995014651)*((:Name("% NaCMC")−
2.85245995014651)*47.7871554829216)+(:Fo−
22.0003631356491)*((:Name("% Glycerin")−
1.49703269551474)*−0.520125030291254)+(:
Name("PBS (mM)")−63.5057099845838)*((:
Name("% Glycerin")−1.49703269551474)*−
0.516575698317358)+(:Name("% NaCMC")−
2.85245995014651)*((:Name("% Glycerin")−
1.49703269551474)*7.81902442047261)+(:
Name("% Glycerin")−1.49703269551474)*((:
Name("% Glycerin")−1.49703269551474)*−
2.08529318048302)

Prediction Formula G" 4.0 Hz 9.16270416349258+−
6.65052721006341*:Fo+−1.30157689213324*:
Name("PBS (mM)")+113.264274857613*:Name
("% NaCMC")+12.6630272567578*:Name("%
Glycerin")+(:Fo−22.0003631356491)*((:Fo−
22.0003631356491)*0.278888472140156)+(:
Fo−22.0003631356491)*((:Name("PBS (mM)
")−63.5057099845838)*−
0.0031022350498589)+(:Name("PBS (mM)")−
63.5057099845838)*((:Name("PBS (mM)")−
63.5057099845838)*0.00757715798304363)+(:
Fo−22.0003631356491)*((:Name("%
NaCMC")−2.85245995014651)*−
1.30849884761416)+(:Name("PBS (mM)")−
63.5057099845838)*((:Name("% NaCMC")−
2.85245995014651)*−0.702979541219968)+(:
Name("% NaCMC")−2.85245995014651)*((:
Name("% NaCMC")−2.85245995014651)
*57.4260758452326)+(:Fo−22.0003631356491)
*((:Name("% Glycerin")−1.49703269551474)*−
0.140690664543388)+(:Name("PBS (mM)")−
63.5057099845838)*((:Name("% Glycerin")−
1.49703269551474)*−0.221880322555676)+(:
Name("% NaCMC")−2.85245995014651)*((:
Name("% Glycerin")−1.49703269551474)
*3.07273854570663)+(:Name("% Glycerin")−
1.49703269551474)*((:Name("% Glycerin")−
1.49703269551474)*−1.0565937205507)

Prediction Formula PF d-R 0.7 Hz
78.8594056631251+−0.391595419225251*:Fo+
0.194490163649969*: Name("PBS (mM)")+−
9.00551677919371*:Name("% NaCMC")+−
1.31216569248401*:Name("% Glycerin")+(:Fo
22.0003631356491)*((:Fo−22.0003631356491)
*0.0397402622686809)+(:Fo−
22.0003631356491)*((:Name("PBS (mM)")−
63.5057099845838)*0.00616186280104159)+(:
Name("PBS (mM)")−63.5057099845838)*((:
Name("PBS (mM)")−63.5057099845838)*−
0.00101989657856309)+(:Fo−
22.0003631356491)*((:Name("% NaCMC")−
2.85245995014651)*−0.843405024379471)+(:
Name("PBS (mM)")−63.5057099845838)*((:
Name("% NaCMC")−2.85245995014651)*−
0.103279939139173)+(:Name("% NaCMC")−
2.85245995014651)*((:Name("% NaCMC")−
2.85245995014651)*−22.9264118725924)+(:
Fo−22.0003631356491)*((:Name("%
Glycerin")−1.49703269551474)*−
0.0439660358574415)+(:Name("PBS (mM)")−
63.5057099845838)*((:Name("% Glycerin")−
1.49703269551474)*−0.0619122070598477)+(:
Name("% NaCMC")−2.85245995014651)*((:
Name("% Glycerin")−1.49703269551474)
*10.1261963249863)+(:Name("% Glycerin")−
1.49703269551474)*((:Name("% Glycerin")−
1.49703269551474)*0.34697984176467)

Prediction Formula PF d-R 0.7 Hz
78.8594056631251+−0.391595419225251*:Fo+
0.194490163649969*:Name("PBS (mM)")+−
9.00551677919371*:Name("% NaCMC")+−
1.31216569248401*:Name("% Glycerin")+(:Fo
22.0003631356491)*((:Fo−22.0003631356491)
*0.0397402622686809)+(:Fo−
22.0003631356491)*((:Name("PBS (mM)")−
63.5057099845838)*0.00616186280104159)+(:
Name("PBS (mM)")−63.5057099845838)*((:
Name("PBS (mM)")−63.5057099845838)*−
0.00101989657856309)+(:Fo−
22.0003631356491)*((:Name("% NaCMC")−
2.85245995014651)−0.843405024379471)+(:
Name("PBS (mM)")−63.5057099845838)*((:
Name("% NaCMC")−2.85245995014651)*−
0.103279939139173)+(:Name("% NaCMC")−
2.85245995014651)*((:Name("% NaCMC")−
2.85245995014651)*−22.9264118725924)+(:
Fo−22.0003631356491)*((:Name("%
Glycerin")−1.49703269551474)*−
0.0439660358574415)+(:Name("PBS (mM)")−
63.5057099845838)*((:Name("% Glycerin")−
1.49703269551474)*−0.0619122070598477)+(:
Name("% NaCMC")−2.85245995014651)*((:
Name("% Glycerin")−1.49703269551474)
*10.1261963249863)+(:Name("% Glycerin")−
1.49703269551474)*((:Name("% Glycerin")−
1.49703269551474)*0.34697984176467)

Example 20

This example consists of the screening model's 59 independent runs of conditions with rheological outputs registered and see following data Tables D and E:

TABLE D

| Output | Min | Max |
| --- | --- | --- |
| Viscosity η * (0.7 Hz, 30τ,30° C. | 7200 | 53000 |
| Tan δ (0.7 Hz, 30τ, 30° C.) | .6 | 1.5 |
| G' elastic modulus, G" viscosity Modulus (0.7 Hz, 30τ, 30° C.) | | 100 |
| Tan δ (4 Hz, 30τ, 30° C.) | 0.3 | 2 |
| G' elastic modulus, G" viscosity Modulus (4 Hz, 30τ, 30° C.) | | 300 |
| Phase Angle δ-R (0.7 Hz, 30τ, 30° C.) | | 60 |
| Phase Angle δ-R (0.7 Hz, 30τ, 30° C.) | | 110 |

Example 20

TABLE E

Screening Data

| | Lot # & Exposure Time | Autoclave time | PBS Conc. (mM) | % Control MinCMC | Glycerin contant | pH | Osmo. [mOsm] | % LOD | Exlos 30GA | Crossover | Crossover (w) | Crossover (G' = G") |
|---|---|---|---|---|---|---|---|---|---|---|---|---|
| 1 | G068060-12 min | 12 | 0 | 2.3 | 0 | 7.211 | 43 | 97.65 | 3.5333 | | 3.11 | 53.6 |
| 2 | G068061-12 min | 12 | 0 | 2.4 | 0 | 7.163 | 56 | 97.75 | 3.4981 | | 1.884 | 50.96 |
| 3 | G068062-12 min | 12 | 0 | 2.5 | 0 | 7.132 | 29 | 97.83 | 3.8121 | | 0.9877 | 48.58 |
| 4 | G068063-12 min | 12 | 0 | 2.6 | 0 | 7.158 | 39 | 97.54 | 4.4364 | | 1.029 | 48.39 |
| 5 | G068060-30 min | 30 | 0 | 2.3 | 0 | 7.164 | 39 | 97.86 | 4.0641 | | 5.799 | 73.04 |
| 6 | G068061-30 min | 30 | 0 | 2.4 | 0 | 7.256 | 53 | 97.75 | 4.2788 | | 7.805 | 69.32 |
| 7 | G068062-30 min | 30 | 0 | 2.5 | 0 | 7.15 | 41 | 97.55 | 3.7253 | | 3.805 | 68.82 |
| 8 | G068063-30 min | 30 | 0 | 2.6 | 0 | 7.151 | 42 | 97.57 | 4.3923 | | 4.393 | 79.81 |
| 9 | G046086-12 min | 12 | 50 | 2.3 | 0 | 7.305 | 153 | 96.81 | 3.9737 | does not cross over G' dominant | | . |
| 10 | G068058-12 min | 12 | 50 | 2.4 | 0 | 7.3 | 161 | 96.9 | 4.0515 | does not cross over G' dominant | | . |
| 11 | G046087-12 min | 12 | 50 | 2.5 | 0 | 7.296 | 151 | 96.84 | 4.1824 | | 28.52 | 99.32 |
| 12 | G068059-12 min | 12 | 50 | 2.6 | 0 | 7.266 | 161 | 96.83 | 4.4981 | | 22.7 | 94.16 |
| 13 | G046086-30 min | 30 | 50 | 2.3 | 0 | 7.328 | 155 | 96.9 | 3.8136 | does not cross over G' dominant | | . |
| 14 | G068058-30 min | 30 | 50 | 2.4 | 0 | 7.315 | 160 | 96.79 | 3.8564 | does not cross over G' dominant | | . |
| 15 | G046087-30 min | 30 | 50 | 2.5 | 0 | 7.312 | 155 | 96.86 | 3.7105 | does not cross over G' dominant | | . |
| 16 | G068059-30 min | 30 | 50 | 2.6 | 0 | 7.308 | 165 | 95.59 | 4.0617 | does not cross over G' dominant | | . |
| 17 | G046088-12 min | 12 | 100 | 2.3 | 0 | 7.286 | 277 | 96.89 | 3.6691 | does not cross over G' dominant | | . |
| 18 | G068056-12 min | 12 | 100 | 2.4 | 0 | 7.286 | 274 | 96.74 | 3.8172 | does not cross over G' dominant | | . |
| 19 | G046088-30 min | 30 | 100 | 2.5 | 0 | 7.288 | 281 | 96.79 | 3.7802 | does not cross over G' dominant | | . |
| 20 | G068057-12 min | 12 | 100 | 2.6 | 0 | 7.289 | 280 | 95.48 | 3.6764 | does not cross over G' dominant | | . |
| 21 | G046089-12 min | 12 | 100 | 2.3 | 0 | 7.3 | 279 | 95.5 | 3.967 | does not cross over G' dominant | | . |
| 22 | G068056-30 min | 30 | 100 | 2.4 | 0 | 7.305 | 271 | 95.82 | 3.5869 | does not cross over G' dominant | | . |
| 23 | G068057-30 min | 30 | 100 | 2.5 | 0 | 7.305 | 277 | 95.65 | 3.2488 | does not cross over G' dominant | | . |
| 24 | G046089-30 min | 30 | 100 | 2.6 | 0 | 7.302 | 277 | 95.53 | 3.6055 | does not cross over G' dominant | | . |
| 25 | G068058-12 min | 12 | 50 | 2.6 | 0 | 7.29 | 157 | 96.59 | 4.0668 | does not cross over G' dominant | | . |
| 26 | G068059-30 min | 30 | 50 | 2.6 | 0 | 7.274 | 156 | 96.53 | 3.8079 | does not cross over G' dominant | | . |
| 27 | G045093-12 min | 12 | 50 | 2.7 | 0 | 7.309 | 172 | 96.41 | 4.1535 | | 21.96 | 103.3 |
| 28 | G045093-30 min | 30 | 50 | 2.7 | 0 | 7.298 | 171 | 96.13 | 3.8003 | | 174.5 | 296.4 |
| 29 | G068071-12 min | 12 | 50 | 2.8 | 0 | 7.3 | 174 | 96.38 | 4.3474 | | 274.6 | 9896 |
| 30 | G068071-30 min | 30 | 50 | 2.8 | 0 | 7.286 | 173 | 96.39 | 3.4174 | | | . |
| 31 | G068094-12 min | 12 | 50 | 2.9 | 0 | 7.304 | 177 | 96.2 | 4.2343 | | 10.53 | 100.8 |
| 32 | G046094-30 min | 30 | 50 | 2.9 | 0 | 7.289 | 177 | 96.14 | 4.4947 | does not cross over G' dominant | | . |
| 33 | G068089-12 min | 12 | 100 | 2.6 | 0 | 7.292 | 285 | 95.4 | 3.958 | does not cross over G' dominant | | . |
| 34 | G046089-30 min | 30 | 100 | 2.6 | 0 | 7.28 | 284 | 95.58 | 3.8755 | does not cross over G' dominant | | . |
| 35 | G068072-12 min | 12 | 100 | 2.7 | 0 | 7.33 | 282 | 95.58 | 4.1847 | | 276.6 | 1163 |
| 36 | G068072-30 min | 30 | 100 | 2.7 | 0 | 7.316 | 283 | 95.49 | 3.6843 | | 247.5 | 1589 |
| 37 | G046096-12 min | 12 | 100 | 2.8 | 0 | 7.326 | 284 | 95.48 | 3.9906 | | 280.9 | 1911 |
| 38 | G046096-30 min | 30 | 100 | 2.8 | 0 | 7.31 | 283 | 95.47 | 4.081 | does not cross over G' dominant | | . |
| 39 | G068073-12 min | 12 | 100 | 2.9 | 0 | 7.35 | 281 | 95.44 | 4.2364 | | 264.7 | 1273 |
| 40 | G068073-30 min | 30 | 100 | 2.9 | 0 | 7.314 | 281 | 95.36 | 3.6419 | does not cross over G' dominant | | . |
| 41 | G046096-12 min | 12 | 50 | 2.6 | 1 | 7.288 | 288 | 95.32 | 4.1196 | | 7.875 | 78.7 |
| 42 | G046096-30 min | 30 | 50 | 2.6 | 1 | 7.268 | 286 | 95.58 | 3.7719 | | 272.5 | 1927 |
| 43 | G068074-12 min | 12 | 50 | 2.7 | 1 | 7.285 | 274 | 95.53 | 4.2729 | | 7.274 | 52.73 |
| 44 | G068074-30 min | 30 | 50 | 2.7 | 1 | 7.26 | 285 | 96.48 | 4.4181 | does not cross over G' dominant | | . |
| 45 | G046097-12 min | 12 | 50 | 2.8 | 1 | 7.299 | 288 | 95.34 | 3.8536 | | 5.744 | 86.50 |
| 46 | G046097-30 min | 30 | 50 | 2.8 | 1 | 7.251 | 286 | 95.42 | 3.9405 | | 265 | 8992 |

TABLE E-continued

Screening Data

| | | | | | | | | | | | |
|---|---|---|---|---|---|---|---|---|---|---|---|
| 47 | G068075-12 min | 12 | 50 | 2.9 | 1 | 7.288 | 293 | 95.23 | 4.4409 | 6.689 | 89.61 |
| 48 | G068075-30 min | 30 | 50 | 2.9 | 1 | 7.262 | 290 | 96.25 | 3.9804 | 273 | 2540 |
| 49 | G068076-12 min | 12 | 100 | 2.6 | 1 | 7.304 | 399 | 94.86 | 3.6623 | does not cross over G' dominant | . |
| 50 | G068076-30 min | 30 | 100 | 2.6 | 1 | 7.29 | 397 | 94.5 | 3.942 | does not cross over G' dominant | |
| 51 | G046098-12 min | 12 | 100 | 2.7 | 1 | 7.302 | 416 | 94.4 | 3.9568 | does not cross over G' dominant | |
| 52 | G046098-30 min | 30 | 100 | 2.7 | 1 | 7.277 | 404 | 94.35 | 4.0682 | 172.8 | 331.1 |
| 53 | G068077-12 min | 12 | 100 | 2.8 | 1 | 7.311 | 403 | 94.46 | 4.062 | does not cross over G' dominant | . |
| 54 | G068077-30 min | 30 | 100 | 2.8 | 1 | 7.296 | 411 | 94.31 | 3.8651 | does not cross over G' dominant | . |
| 55 | G046099-12 min | 12 | 100 | 2.9 | 1 | 7.306 | 407 | 94.27 | 3.6058 | does not cross over G' dominant | . |
| 56 | G046099-30 min | 30 | 100 | 2.9 | 1 | 7.27 | 413 | 94.22 | 4.6409 | does not cross over G' dominant | . |
| 57 | G065074-Fo26 | 15 | 25 | 2.6 | 1.5 | 7.299 | 268 | 96.6 | . | 2.831 | 50.82 |
| 58 | G065023-Fo26 | 15 | 25 | 2.6 | 1.5 | . | . | . | . | 10.37 | 73.41 |
| 59 | G065063-Fo26 | 15 | 25 | 2.6 | 1.5 | 7.345 | 288 | 95.54 | . | 0.9147 | 43.56 |

| | Crossover (Hz) | 0.7 Hz [n*][cP] | 0.7 Hz Tan(d) | G' 0.7 Hz | G" 0.7 Hz | 4 Hz \|n*\| [cP] | 4 Hz Tan(d) | G' 4 Hz | G" 4 Hz | 11 Hz \|n*\| [cP] | 11 Hz Tan(d) | G' 11 Hz | G" 11 Hz | defraction angle 0.7 Hz | defraction angle 4 Hz |
|---|---|---|---|---|---|---|---|---|---|---|---|---|---|---|---|
| 1 | 0.4951 | 20895 | 0.92614 | 68.585 | 61.969 | 7576.3 | 0.69279 | 159.29 | 110.52 | 3846.8 | 0.58949 | 225.99 | 144.01 | 44.363 | 52.352 |
| 2 | 0.2939 | 24549 | 0.84694 | 83.86 | 71.137 | 8867.3 | 0.64379 | 186.34 | 121.4 | 4347.9 | 0.6049 | 258.37 | 156.48 | 41.55 | 47.033 |
| 3 | 0.1572 | 31118 | 0.77476 | 106.73 | 84.385 | 10679 | 0.59886 | 231.52 | 136.76 | 5128.2 | 0.54829 | 312.49 | 171.31 | 38.877 | 42 |
| 4 | 0.1637 | 31734 | 0.75432 | 110.36 | 86.713 | 10881 | 0.60675 | 237.36 | 143.92 | 5313.1 | 0.54453 | 324.49 | 177.26 | 39.212 | 42.029 |
| 5 | 1.399 | 16156 | 1.1305 | 47.189 | 53.598 | 5618.6 | 0.80646 | 129.87 | 105.01 | 3499.9 | 0.74706 | 194.44 | 146.63 | 50.366 | 61.49 |
| 6 | 1.21 | 19263 | 1.0603 | 57.743 | 62.524 | 7787.63 | 0.77636 | 154.66 | 120.5 | 4086.2 | 0.70196 | 229.67 | 164.86 | 48.849 | 56.221 |
| 7 | 0.5737 | 24471 | 0.96272 | 77.801 | 75.03 | 9280.6 | 0.71134 | 190.69 | 136 | 4739 | 0.54427 | 276.69 | 176.33 | 45.264 | 49.643 |
| 8 | 0.6992 | 25863 | 0.99592 | 80.11 | 80.046 | 10028 | 0.73299 | 204.15 | 149.86 | 6207.3 | 0.86411 | 302.51 | 197.97 | 46.228 | 49.469 |
| 9 | . | 7998.4 | 1.5653 | 18.92 | 29.725 | 3905.9 | 1.1306 | 85.208 | 73.83 | 2289.2 | 1.162 | 103.7 | 120.36 | 60.983 | 94.174 |
| 10 | . | 8494.8 | 1.5341 | 20.408 | 31.415 | 4235.8 | 1.1206 | 71.02 | 79.77 | 2500.6 | 0.87066 | 116.65 | 129.51 | 60.258 | 89.874 |
| 11 | 4.54 | 11295 | 1.3912 | 28.976 | 40.483 | 5266.1 | 1.0151 | 93.045 | 94.709 | 2991.1 | 0.8926 | 149.3 | 148.26 | 56.899 | 77.326 |
| 12 | 3.612 | 12366 | 1.3227 | 32.857 | 43.583 | 5541 | 0.98375 | 99.537 | 95.141 | 3103.8 | 0.93515 | 157.3 | 146.89 | 55.292 | 74.277 |
| 13 | . | 2953 | 2.7729 | 3.0743 | 6.5321 | 1384.6 | 2.2124 | 14.262 | 31.563 | 1087 | 7.2509 | 13.946 | 72.054 | 83.997 | 151.26 |
| 14 | . | 3408 | 2.488 | 5.5854 | 13.945 | 2201.6 | 1.7583 | 27.274 | 48.08 | 1516.5 | 2.5019 | 40.766 | 94.947 | 76.434 | 131.69 |
| 15 | . | 3506.7 | 2.4284 | 5.8735 | 14.299 | 2208.6 | 1.7882 | 27.262 | 48.865 | 1551.9 | 2.6943 | 41.933 | 97.573 | 76.69 | 131.28 |
| 16 | | 4232.1 | 2.3014 | 7.4148 | 17.099 | 2597.4 | 1.7028 | 33.05 | 56.361 | 1811.3 | 1.9732 | 57.348 | 110.15 | 73.241 | 123.37 |
| 17 | . | 4324.5 | 1.9384 | 8.7203 | 16.947 | 2438.4 | 1.513 | 33.825 | 51.208 | 1614.2 | 1.7602 | 51.717 | 95.98 | 69.152 | 128.13 |
| 18 | . | 4679.6 | 1.9602 | 9.1613 | 18.012 | 2578.2 | 1.633 | 35.919 | 54.048 | 1688.7 | 1.9208 | 54.609 | 102.23 | 59.074 | 122.09 |
| 19 | . | 5236.2 | 1.9248 | 10.836 | 20.602 | 3040.2 | 1.4876 | 43.08 | 63.28 | 2002.3 | 1.622 | 72.880 | 117.76 | 67.91 | 113.15 |
| 20 | . | 5885.1 | 1.889 | 11.87 | 22.101 | 3161 | 1.4554 | 44.896 | 65.453 | 2047.5 | 1.5363 | 76.614 | 118.97 | 67.087 | 111.15 |
| 21 | | 918.86 | 3.8507 | 0.99050 | 3.9142 | 605.21 | 1.3619 | 15.376 | 15.655 | 711.98 | 7.3698 | 10.726 | 48.646 | 106.17 | 169.5 |
| 22 | . | 1124.1 | 3.3350 | 1.3953 | 4.7414 | 891.51 | 3.5541 | 5.9828 | 16.958 | 772.54 | 25.067 | 6.066 | 52.929 | 98.788 | 167.19 |
| 23 | . | 1185.8 | 3.2898 | 1.4992 | 4.9953 | 794.52 | 3.658 | 5.7229 | 19.685 | 821.27 | 137.65 | 4.9109 | 56.799 | 97.23 | 165.13 |
| 24 | . | 1140.7 | 3.4858 | 1.3502 | 4.9178 | 788.79 | 6.3557 | 3.3461 | 19.596 | 837.43 | 559.34 | 5.3149 | 57.935 | 97.299 | 155.27 |
| 25 | . | 10067 | 1.4726 | 24.9 | 36.777 | 4839.9 | 1.0983 | 82.151 | 90.26 | 2822 | 1.0808 | 132.91 | 143.57 | 58.7 | 83.164 |
| 26 | . | 4196.9 | 2.2246 | 7.6651 | 16.87 | 2522 | 1.64 | 33.014 | 54.181 | 1704.1 | 2.0719 | 52.101 | 104.51 | 72.537 | 124.34 |
| 27 | 3.494 | 13782 | 1.3235 | 36.556 | 48.543 | 6181.2 | 0.97838 | 111.34 | 109.13 | 3477.3 | 0.90647 | 178.63 | 162.07 | 55.128 | 70.395 |
| 28 | . | 4668 | 2.2379 | 9.1696 | 18.325 | 2818.5 | 1.6551 | 36.642 | 60.707 | 1942.1 | 1.6432 | 84.312 | 117.66 | 55.128 | 70.395 |
| 29 | 27.77 | 13100 | 1.3663 | 34.041 | 46.655 | 3361.8 | 1.4068 | 49.038 | 69.048 | 3436.8 | 0.96974 | 171.03 | 165.83 | 65.794 | 107.09 |
| 30 | 43.71 | 4350.7 | 2.1766 | 7.991 | 17.446 | 2644.3 | 1.6791 | 33.974 | 57.153 | 1792.6 | 2.0595 | 55.19 | 109.46 | 71.619 | 122.26 |
| 31 | 1.891 | 20573 | 1.114 | 60.567 | 87.655 | 8323.8 | 0.95491 | 159.61 | 136.65 | 4488.1 | 0.78016 | 245.34 | 192.46 | 49.682 | 57.966 |
| 32 | . | 6794 | 1.9523 | 13.582 | 26.701 | 3991.0 | 1.4757 | 56.29 | 83.27 | 2655.8 | 1.4154 | 105.82 | 151.06 | 67.259 | 99.875 |
| 33 | . | 4721.6 | 2.012 | 9.2534 | 18.686 | 2726.3 | 1.5747 | 36.712 | 57.925 | 1824.6 | 1.9612 | 56.164 | 110.83 | 69.518 | 119.83 |

TABLE E-continued

Screening Data

| | | | | | | | | | | |
|---|---|---|---|---|---|---|---|---|---|---|
| 34 | | 955.37 | 1.1275 | 4.2449 | 8.8203 | 855.72 | 4.8975 | 4.5073 | 21.041 | 842.97 | 5.5757 | 17.24 | 58.186 | 118.4 | 163.8 |
| 35 | 44.03 | 6176.4 | 1.8296 | 13.081 | 23.396 | 923.67 | 3.746 | 6.0635 | 22.352 | 2136.9 | 1.5265 | 80.833 | 123.73 | 91.583 | 162.12 |
| 36 | 39.4 | 1416.2 | 1.9808 | 5.9109 | 2.9582 | 1009.3 | 2.9981 | 7.9991 | 23.947 | 935.42 | 3.9211 | 19.875 | 64.732 | 83.705 | 160 |
| 37 | 41.62 | 8012.3 | 1.6038 | 17.898 | 30.376 | 4131.6 | 1.3076 | 63.207 | 82.782 | 2579.7 | 1.2844 | 109.88 | 141.26 | 62.877 | 95.24 |
| 38 | | 1778.7 | 2.7815 | 2.6484 | 7.3762 | 1087.6 | 2.8857 | 8.9391 | 25.801 | 1074.9 | 6.1524 | 13.657 | 73.718 | 83.932 | 158.34 |
| 39 | 45.32 | 9469.7 | 1.5982 | 22.106 | 35.409 | 4824.1 | 1.2352 | 78.373 | 94.609 | 2970.2 | 1.1624 | 132.91 | 157.01 | 61.042 | 86.958 |
| 40 | | 2492.2 | 2.3775 | 4.2501 | 10.132 | 1647.7 | 2.4594 | 15.589 | 38.317 | 1380.7 | 1.108 | 20.703 | 90.83 | 78.48 | 145.54 |
| 41 | 1.254 | 18653 | 1.9799 | 55.871 | 60.485 | 7485.5 | 0.81893 | 146.09 | 119.83 | 3986 | 0.7472 | 220.71 | 157.51 | 48.686 | 58.787 |
| 42 | 43.37 | 4149.7 | 2.2634 | 7.3196 | 16.747 | 2669.4 | 1.7161 | 32.516 | 55.846 | 1778.1 | 2.0984 | 53.497 | 110.42 | 73.19 | 123.99 |
| 43 | 1.158 | 20380 | 1.068 | 61.456 | 65.69 | 8208.7 | 0.80481 | 161.32 | 130.04 | 4335.8 | 0.74647 | 240.77 | 180.27 | 48.403 | 56.196 |
| 44 | | 4032.0 | 2.2291 | 7.2821 | 16.216 | 2495.7 | 1.7172 | 31.513 | 54.219 | 1750.1 | 2.0830 | 108.13 | 72.839 | 125.4 |
| 45 | 0.9142 | 23803 | 1.0282 | 73.296 | 75.506 | 9636 | 0.78768 | 181 | 150.64 | 5100.9 | 0.70813 | 852.744 | 204.83 | 47.189 | 52.616 |
| 46 | 42.17 | 4461.4 | 2.3141 | 7.7804 | 18.042 | 2842.2 | 1.7394 | 35.564 | 51.966 | 1978.4 | 1.7562 | 288.86 | 121.02 | 73.025 | 119.24 |
| 47 | 1.065 | 23060 | 1.0466 | 70.303 | 73.7 | 9275.2 | 0.79754 | 182.97 | 145.1 | 4901.2 | 0.72917 | 62.154 | 200.34 | 47.741 | 53.548 |
| 48 | 43.4 | 5027.2 | 2.1063 | 9.4906 | 20.039 | 3037.4 | 1.873 | 39.146 | 65.626 | 2089.6 | 1.8494 | 274.72 | 126.72 | 70.243 | 115.34 |
| 49 | | 2981.6 | 2.187 | 5.4524 | 11.955 | 1693.5 | 1.8859 | 22.277 | 42.012 | 1380 | 3.5247 | 68.932 | 88.973 | 74.834 | 139.09 |
| 50 | | 1802.1 | 2.8477 | 2.609 | 7.4909 | 1192.3 | 2.519 | 11.002 | 27.814 | 1006.7 | 9.8164 | 29.571 | 88.989 | 86.516 | 155.78 |
| 51 | | 4670.9 | 2.0083 | 9.1617 | 18.436 | 2841.3 | 1.6598 | 36.879 | 61.238 | 1958 | 1.9395 | 8.3877 | 120.25 | 89.535 | 118.63 |
| 52 | 27.51 | 2322.9 | 2.7028 | 3.5405 | 9.6543 | 1535.3 | 2.0229 | 17.063 | 34.53 | 1274.3 | 4.9474 | 81.942 | 85.278 | 77.327 | 147.49 |
| 53 | | 4485.5 | 2.0047 | 8.8106 | 17.899 | 2695.7 | 1.6875 | 34.556 | 58.368 | 1864.3 | 1.9902 | 19.88 | 114.73 | 69.731 | 121.37 |
| 54 | | 3019.2 | 2.4273 | 5.0433 | 12.316 | 1955.8 | 1.9714 | 22.134 | 43.804 | 1496.5 | 3.0783 | 57.773 | 97.613 | 76.999 | 137.76 |
| 55 | | 7279.3 | 1.6546 | 16.584 | 27.515 | 3848.7 | 1.3379 | 57.994 | 77.732 | 2437.6 | 1.1554 | 33.231 | 136.94 | 62.731 | 99.174 |
| 56 | | 3273.5 | 2.4413 | 5.4408 | 13.365 | 2119.5 | 1.905 | 24.676 | 47.113 | 1545 | 2.7106 | 99.422 | 96.799 | 76.428 | 134.19 |
| 57 | 0.4506 | 20623 | 0.93274 | 66.555 | 62.197 | 7990.6 | 0.7477 | 161.44 | 120.86 | 4123.7 | 0.71373 | 38.506 | 166.25 | 44.491 | 54.137 |
| 58 | 1.65 | 14778 | 1.1257 | 43.201 | 48.853 | 6200.3 | 0.87145 | 117.89 | 102.9 | 3339.5 | 0.83468 | 232.69 | 148.83 | 50.389 | 66.226 |
| 59 | 0.1456 | 30703 | 0.79724 | 105.26 | 84.507 | 10825 | 0.83141 | 231.28 | 146.22 | 5306 | 0.58547 | 177.54 | 188.12 | 39.688 | 43.542 |
| | | | | | | | | | | | | 317.72 | | | |

Although the present invention has been described with reference to preferred embodiments, one skilled in the art can easily ascertain its essential characteristics and without departing from the spirit and scope thereof, can make various changes and modifications of the invention to adapt it to various usages and conditions. Those skilled in the art will recognize or be able to ascertain using no more than routine experimentation, various reasonable equivalents to the specific embodiments of the invention herein. Such equivalents are to be encompassed in the scope of the present invention. For example, the plasticizer utilized in the examples of the present invention is primarily glycerin. However, one of ordinary skill in the art would appreciate that other plasticizers may be used without departing from the spirit and scope of the invention.

The invention claimed is:

1. A method of preparing a tissue implant comprising: (i) preparing an aqueous composition comprising between 2.6 wt. % and 3.2 wt. % carboxymethylcellulose and 15 wt. % glycerin; (ii) adding between 0.2 wt. % and 0.5 wt % lidocaine; and (iii) sterilizing the composition by autoclaving for about 3 minutes to about 12 minutes to prepare the tissue implant, wherein the tissue implant is suitable for augmentation of a tissue selected from nasal furrows, frown lines, midfacial tissue, jaw-line, chin, and cheeks.

2. The method of claim 1, wherein the aqueous composition is in 25 mM to 100 mM phosphate buffer.

3. The method of claim 2, wherein the phosphate buffer has a pH from 7.2 to 8.0.

4. The method of claim 1, wherein the tissue implant is a midfacial tissue implant.

5. The method of claim 1, wherein the tissue implant is a jaw-line implant.

6. A method of preparing a tissue implant comprising: (i) preparing an aqueous composition comprising between 2.6 wt. % and 3.2 wt. % carboxymethylcellulose and 15 wt. % glycerin; (ii) adding between 5 wt. % and 65 wt. % calcium hydroxyapatite; (iii) adding between 0.2 wt. % and 0.5 wt % lidocaine; and (iv) sterilizing the composition by autoclaving for about 3 minutes to about 12 minutes to prepare the tissue implant, wherein the tissue implant is suitable for augmentation of a tissue selected from nasal furrows, frown lines, midfacial tissue, jaw-line, chin, and cheeks.

7. The method of claim 6, wherein the aqueous composition is in 25 mM to 100 mM phosphate buffer.

8. The method of claim 7, wherein the phosphate buffer has a pH from 7.2 to 8.0.

9. The method of claim 6, wherein the tissue implant is a midfacial tissue implant.

10. The method of claim 6, wherein the tissue implant is a jaw-line implant.

11. The method of claim 6, wherein the calcium hydroxyapatite is added between 10 wt. % and 50 wt. %.

12. The method of claim 6, wherein the calcium hydroxyapatite is added between 30 wt. % and 45 wt. %.

* * * * *